United States Patent
Wolff et al.

(10) Patent No.: US 7,138,382 B2
(45) Date of Patent: *Nov. 21, 2006

(54) COMPOSITIONS AND METHODS FOR DRUG DELIVERY USING PH SENSITIVE MOLECULES

(75) Inventors: Jon A. Wolff, Madison, WI (US); James E. Hagstrom, Middleton, WI (US); David B. Rozema, Madison, WI (US); Sean D. Monahan, Madison, WI (US); Vladimir G. Budker, Middleton, WI (US)

(73) Assignee: Mirus Bio Corporation, Madison, WI (US)

( * ) Notice: Subject to any disclaimer, the term of this patent is extended or adjusted under 35 U.S.C. 154(b) by 553 days.

This patent is subject to a terminal disclaimer.

(21) Appl. No.: 10/619,778

(22) Filed: Jul. 15, 2003

(65) Prior Publication Data

US 2004/0058446 A1    Mar. 25, 2004

Related U.S. Application Data

(62) Division of application No. 09/589,978, filed on Jun. 7, 2000, now Pat. No. 6,630,351.

(60) Provisional application No. 60/172,809, filed on Dec. 21, 1999, provisional application No. 60/167,836, filed on Nov. 29, 1999, provisional application No. 60/137,859, filed on Jun. 7, 1999.

(51) Int. Cl.
*A61K 48/00*    (2006.01)
*A61K 31/711*   (2006.01)
*A61K 31/7105*  (2006.01)
*A61K 38/04*    (2006.01)
*C12N 15/87*    (2006.01)
*A61K 9/127*    (2006.01)

(52) U.S. Cl. .......................... 514/44; 435/455; 530/300

(58) Field of Classification Search ..................... None
See application file for complete search history.

(56) References Cited

U.S. PATENT DOCUMENTS 6,630,351 B1 * 10/2003 Monahan et al. ........... 435/455

* cited by examiner

*Primary Examiner*—David Guzo
(74) *Attorney, Agent, or Firm*—Mark K. Johnson; Kirk Ekena

(57) ABSTRACT

A system relating to the delivery of desired compounds (e.g., drugs and nucleic acids) into cells using pH-sensitive delivery systems. The system provides compositions and methods for the delivery and release of a compound to a cell.

12 Claims, No Drawings

SEQUENCE LISTING

```
<160> NUMBER OF SEQ ID NOS: 11

<210> SEQ ID NO 1
<211> LENGTH: 14
<212> TYPE: PRT
<213> ORGANISM: SV40

<400> SEQUENCE: 1

Cys Gly Tyr Gly Pro Lys Lys Lys Arg Lys Val Gly Gly Cys
1               5                   10

<210> SEQ ID NO 2
<211> LENGTH: 13
<212> TYPE: PRT
<213> ORGANISM: SV40

<400> SEQUENCE: 2

Cys Gly Tyr Gly Pro Lys Lys Lys Arg Lys Val Gly Gly
1               5                   10

<210> SEQ ID NO 3
<211> LENGTH: 39
<212> TYPE: PRT
<213> ORGANISM: SV40

<400> SEQUENCE: 3

Cys Lys Lys Lys Ser Ser Ser Asp Asp Glu Ala Thr Ala Asp Ser Gln
1               5                   10                  15

His Ser Thr Pro Pro Lys Lys Lys Arg Lys Val Glu Asp Pro Lys Asp
                20                  25                  30

Phe Pro Ser Glu Leu Leu Ser
            35

<210> SEQ ID NO 4
<211> LENGTH: 37
<212> TYPE: PRT
<213> ORGANISM: SV40

<400> SEQUENCE: 4

Cys Lys Lys Lys Trp Asp Asp Glu Ala Thr Ala Asp Ser Gln His Ser
1               5                   10                  15

Thr Pro Pro Lys Lys Lys Arg Lys Val Glu Asp Pro Lys Asp Phe Pro
                20                  25                  30

Ser Glu Leu Leu Ser
            35
```

-continued

<210> SEQ ID NO 5
<211> LENGTH: 31
<212> TYPE: PRT
<213> ORGANISM: SV40

<400> SEQUENCE: 5

Cys Tyr Asn Asp Phe Gly Asn Tyr Asn Gln Ser Ser Asn Phe Gly
1               5                   10                  15

Pro Met Lys Gln Gly Asn Phe Gly Gly Arg Ser Ser Gly Pro Tyr
            20                  25                  30

<210> SEQ ID NO 6
<211> LENGTH: 10
<212> TYPE: PRT
<213> ORGANISM: SV40

<400> SEQUENCE: 6

Cys Lys Arg Gly Pro Lys Arg Pro Arg Pro
1               5                   10

<210> SEQ ID NO 7
<211> LENGTH: 22
<212> TYPE: PRT
<213> ORGANISM: SV40

<400> SEQUENCE: 7

Cys Lys Lys Ala Val Lys Arg Pro Ala Ala Thr Lys Lys Ala Gly Gln
1               5                   10                  15

Ala Lys Lys Lys Lys Leu
            20

<210> SEQ ID NO 8
<211> LENGTH: 14
<212> TYPE: PRT
<213> ORGANISM: SV40

<400> SEQUENCE: 8

Cys Lys Lys Lys Gly Pro Ala Ala Lys Arg Val Lys Leu Asp
1               5                   10

<210> SEQ ID NO 9
<211> LENGTH: 4
<212> TYPE: PRT
<213> ORGANISM: ER retaining signal

<400> SEQUENCE: 9

Lys Asp Glu Leu
1

<210> SEQ ID NO 10
<211> LENGTH: 21
<212> TYPE: PRT
<213> ORGANISM: KL3

<400> SEQUENCE: 10

Lys Leu Leu Lys Leu Leu Lys Leu Trp Leu Lys Leu Leu Lys Leu
1               5                   10                  15

Leu Leu Lys Leu Leu
            20

<210> SEQ ID NO 11
<211> LENGTH: 8

```
<212> TYPE: PRT
<213> ORGANISM: MC151

<400> SEQUENCE: 11

Glu Glu Glu Glu Glu Glu Glu Glu
1               5
```

COMPOSITIONS AND METHODS FOR DRUG DELIVERY USING PH SENSITIVE MOLECULES

CROSS-REFERENCE TO RELATED APPLICATIONS

This application claims the benefit of prior provisional applications 60/137,859 filed on Jun. 7, 1999, 60/167,836 filed on Nov. 29, 1999 and 60/172,809 filed on Dec. 21, 1999 and is a divisional application of Ser. No. 09/589,978 filed on Jun. 7, 2000 now U.S. Pat. No. 6,630,351.

FIELD OF THE INVENTION

The present invention relates to the delivery of desired compounds (e.g., drugs and nucleic acids) into cells using pH-sensitive delivery systems. The present invention provides compositions and methods for the delivery and release of a compound of interest to a cell.

BACKGROUND OF THE INVENTION

Drug Delivery

A variety of methods and routes of administration have been developed to deliver pharmaceuticals that include small molecular drugs and biologically active compounds such as peptides, hormones, proteins, and enzymes to their site of action. Parenteral routes of administration include intravascular (intravenous, intraarterial), intramuscular, intraparenchymal, intradermal, subdermal, subcutaneous, intratumor, intraperitoneal, and intralymphatic injections that use a syringe and a needle or catheter. The blood circulatory system provides systemic spread of the pharmaceutical. Polyethylene glycol and other hydrophilic polymers have provided protection of the pharmaceutical in the blood stream by preventing its interaction with blood components and to increase the circulatory time of the pharmaceutical by preventing opsonization, phagocytosis and uptake by the reticuloendothelial system. For example, the enzyme adenosine deaminase has been covalently modified with polyethylene glycol to increase the circulatory time and persistence of this enzyme in the treatment of patients with adenosine deaminase deficiency.

The controlled release of pharmaceuticals after their administration is under intensive development. Pharmaceuticals have also been complexed with a variety of biologically-labile polymers to delay their release from depots. These polymers have included copolymers of poly(lactic/glycolic acid) (PLGA) (Jain, R. et al. Drug Dev. Ind. Pharm. 24, 703–727 (1998), ethylvinyl acetate/polyvinyl alcohol (Metrikin, D C and Anand, R, Curr Opin Ophthalmol 5, 21–29, 1994) as typical examples of biodegradable and non-degradable sustained release systems respectively.

Transdermal routes of administration have been effected by patches and ionotophoresis. Other epithelial routes include oral, nasal, respiratory, and vaginal routes of administration. These routes have attracted particular interest for the delivery of peptides, proteins, hormones, and cytokines, which are typically administered by parenteral routes using needles. For example, the delivery of insulin via respiratory, oral, or nasal routes would be very attractive for patients with diabetes mellitus. For oral routes, the acidity of the stomach (pH less than 2) is avoided for pH-sensitive compounds by concealing peptidase-sensitive polypaptides inside pH-sensitive hydrogel matrix (copolymers of poly-ethyleneglycol and polyacrylic acid). After passing low pH compartments of gastrointestinal tract such structures swells at higher pH releasing thus a bioactive compound (Lowman A M et al. J. Pharm. Sci. 88, 933–937 (1999). Capsules have also been developed that release their contents within the small intestine based upon pH-dependent solubility of a polymer. Copolymers of polymethacrylic acid (Eudragit S, Rohm America) are known as polymers which are insoluble at lower pH but readily solubilized at higher pH, so they are used as enteric coatings (Z Hu et al. J. Drug Target., 7, 223, 1999).

Biologically active molecules may be assisted by a reversible formation of covalent bonds. Quite often, it is found that the drug administered to a patient is not the active form of the drug, but is what is a called a prodrug that changes into the actual biologically active compound upon interactions with specific enzymes inside the body. In particular, anti-cancer drugs are quite toxic and are administered as prodrugs which do not become active until they come in contact with the cancerous cell (Sezaki, I I., Takakura, Y., Hashida, M. Adv. Drug. Delivery Reviews 3, 193, 1989).

Recent studies have found that pH in solid tumors is 0.5 to 1 units lower than in normal tissue (Gerweck L E et al. Cancer Res. 56, 1194 (1996). Hence, the use of pH-sensitive polymers for tumor targeting is justified. However, this approach was demonstrated only in vitro (Berton, M, Eur. J. Pharm. Biopharm. 47, 119–23, 1999).

Liposomes were also used as drug delivery vehicles for low molecular weight drugs and macromolecules such as amphotericin B for systemic fungal infections and candidiasis. Inclusion of anti-cancer drugs such as adriamycin have been developed to increase their delivery to tumors and reduce it to other tissue sites (e.g. heart) thereby decreasing their toxicity. pH-sensitive polymers have been used in conjunction with liposomes for the triggered release of an encapsulated drug. For example, hydrophobically-modified N-isopropylacrylamide-methacrylic acid copolymer can render regular egg phosphatidyl chloline liposomes pH-sensitive by pH-dependent interaction of grafted aliphatic chains with lipid bilayer (O Meyer et al., FEBS Lett., 421, 61, 1998).

Gene and Nucleic Acid-Based Delivery

Gene or polynucleotide transfer is the cardinal process of gene therapy. The gene needs to be transferred across the cell membrane and enter the nucleus where the gene can be expressed. Gene transfer methods currently being explored included viral vectors and physical-chemical methods.

Viruses have evolved over millions of year to transfer their genes into mammalian cells. Viruses can be modified to carry a desired gene and become a "vector" for gene therapy. Using standard recombinant techniques, the harmful or superfluous viral genes can be removed and replaced with the desired normal gene. This was first accomplished with mouse retroviruses. The development of retroviral vectors were the catalyst that promoted current gene therapy efforts. However, they cannot infect all cell types very efficiently, especially in vivo. Other viral vectors based on Herpes virus are being developed to enable more efficient gene transfer into brain cells. Adenoviral and adenoassociated vectors are being developed to infect lung and other cells.

Besides using viral vectors, it is possible to directly transfer genes into mammalian cells. Usually, the desired gene is placed within bacterial plasmid DNA along with a mammalian promoter, enhancer, and other sequences that enable the gene to be expressed in mammalian cells. Several milligrams of the plasmid DNA containing all these sequences can be prepared and purified from the bacterial cultures. The plasmid DNA containing the desired gene can be incorporated into lipid vesicles (liposomes including cationic lipids such as Lipofectin) that then transfer the plasmid DNA into the target cell. Plasmid DNA can also be complexed with proteins that target the plasmid DNA to specific tissues just as certain proteins are taken up (endocytosed) by specific cells. Also, plasmid DNA can be complexed with polymers such as polylysine and polyethylenimine. Another plasmid-based technique involves "shooting" the plasmid DNA on small gold beads into the cell using a "gun". Finally, muscle cells in vivo have the unusual ability to take up and express plasmid DNA.

Gene therapy approaches can be classified into direct and indirect methods. Some of these gene transfer methods are most effective when directly injected into a tissue space. Direct methods using many of the above gene transfer techniques are being used to target tumors, muscle, liver, lung, and brain. Other methods are most effective when applied to cells or tissues that have been removed from the body and the genetically-modified cells are then transplanted back into the body. Indirect approaches in conjunction with retroviral vectors are being developed to transfer genes into bone marrow cells, lymphocytes, hepatocytes, myoblasts and skin cells.

Gene Therapy and Nucleic Acid-Based Therapies

Gene therapy promises to be a revolutionary advance in the treatment of disease. It is a fundamentally new approach for treating disease that is different from the conventional surgical and pharmaceutical therapies. Conceptually, gene therapy is a relatively simple approach. If someone has a defective gene, then gene therapy would fix the defective gene. The disease state would be modified by manipulating genes instead of their products, i.e. proteins, enzymes, enzyme substrates and enzyme products. Although, the initial motivation for gene therapy was the treatment of genetic disorders, it is becoming increasingly apparent that gene therapy will be useful for the treatment of a broad range of acquired diseases such as cancer, infectious disorders (AIDS), heart disease, arthritis, and neurodegenerative disorders (Parkinson's and Alzheimer's).

Gene therapy promises to take full-advantage of the major advances brought about by molecular biology. While, biochemistry is mainly concerned with how the cell obtains the energy and matter that is required for normal function, molecular biology is mainly concerned with how the cell gets the information to perform its functions. Molecular biology wants to discover the flow of information in the cell. Using the metaphor of computers, the cell is the hardware while the genes are the software. In this sense, the purpose of gene therapy is to provide the cell with a new program (genetic information) so as to reprogram a dysfunctional cell to perform a normal function. The addition of a new cellular function is provided by the insertion of a foreign gene that expresses a foreign protein or a native protein at amounts that are not present in the patient.

The inhibition of a cellular function is provided by anti-sense approaches (that is acting against messenger RNA) and that includes oligonucleotides complementary to the messenger RNA sequence and ribozymes. Messenger RNA (mRNA) is an intermediate in the expression of the DNA gene. The mRNA is translated into a protein. "Antisense" methods use a RNA sequence or an oligonucleotide that is made complementary to the target mRNA sequence and therefore binds specifically to the target messenger RNA. When this anti-sense sequence binds to the target mRNA, the mRNA is somehow destroyed or blocked from being translated. Ribozymes destroy a specific mRNA by a different mechanism. Ribozymes are RNA's that contain sequence complementary to the target messenger RNA plus a RNA sequence that acts as an enzyme to cleave the messenger RNA, thus destroying it and preventing it from being translated. When these anti-sense or ribozyme sequences are introduced into a cell, they would inactivate their specific target mRNA and reduce their disease-causing properties.

Several recessive genetic disorders are being considered for gene therapy. One of the first uses of gene therapy in humans has been used for the genetic deficiency of the adenosine deaminase (ADA) gene. Other clinical gene therapy trials have been conducted for cystic fibrosis, familial hypercholesteremia caused by a defective LDL-receptor gene and partial ornithine transcarbomylase deficiency. Both indirect and direct gene therapy approaches are being developed for Duchenne muscular dystrophy. Patients with this type of muscular dystrophy eventually die from loss of their respiratory muscles. Direct approaches include the intramuscular injection of naked plasmid DNA or adenoviral vectors.

A wide variety of gene therapy approaches for cancer are under investigation in animals and in human clinical trials. One approach is to express in lymphocytes and in the tumor cells, cytokine genes that stimulate the immune system to destroy the cancer cells. The cytokine genes would be transferred into the lymphocytes by removing the lymphocytes from the body and infecting them with a retroviral vector carrying the cytokine gene. The tumor cells would be similarly genetically modified by this indirect approach to express cytokines within the tumor. Direct approaches involving the expression of cytokines in tumor cells in situ are also being considered. Other genes besides cytokines may be able to induce an immune response against the cancer. One approach that has entered clinical trials is the direct injection of HLA-B7 gene (which encodes a potent immunogen) within lipid vesicles into malignant melanomas in order to induce a more effective immune response against the cancer.

"Suicide" genes are genes that kill cells that express the gene. For example, the diphtheria toxin gene directly kills cells. The Herpes thymidine kinase (TK) gene kills cells in conjunction with acyclovir (a drug used to treat Herpes viral infections). Other gene therapy approaches take advantage of our knowledge of oncogenes and suppressor tumor genes—also known as anti-oncogenes. The loss of a functioning anti-oncogene plays a decisive role in childhood tumors such as retinoblastoma, osteosarcoma and Wilms tumor and may play an important role in more common tumors such as lung, colon and breast cancer. Introduction of the normal anti-oncogene back into these tumor cells may convert them back to normal cells. The activation of oncogenes also plays an important role in the development of cancers. Since these oncogenes operate in a "dominant" fashion, treatment will require inactivation of the abnormal oncogene. This can be done using either "anti-sense" or ribozyme methods that selectively inactivate a specific messenger RNA in a cell.

Gene therapy can be used as a type of vaccination to prevent infectious diseases and cancer. When a foreign gene is transferred into a cell and the protein is made, the foreign protein is presented to the immune system differently from simply injecting the foreign protein into the body. This different presentation is more likely to cause a cell-mediated immune response which is important for fighting latent viral infections such as human immunodeficiency virus (HIV causes AIDS), Herpes and cytomegalovirus. Expression of the viral gene within a cell simulates a viral infection and induces a more effective immune response by fooling the body that the cell is actually infected by the virus, without the danger of an actual viral infection.

One direct approach uses the direct intramuscular injection of naked plasmid DNA to express a viral gene in muscle cells. The "gun" has also been shown to be effective at inducing an immune response by expressing foreign genes in the skin. Other direct approaches involving the use of retroviral, vaccinia or adenoviral vectors are also being developed. An indirect approach has been developed to remove fibroblasts from the skin, infect them with a retroviral vector carrying a viral gene and transplant the cells back into the body. The envelope gene from the AIDS virus (HIV) is often used for these purposes. Many cancer cells express specific genes that normal cells do not. Therefore, these genes specifically expressed in cancer cells can be used for immunization against cancer.

Besides the above immunization approaches, several other gene therapies are being developed for treating infectious disease. Most of these new approaches are being developed for HIV infection and AIDS. Many of them will involve the delivery of anti-sense or ribozyme sequences directed against the particular viral messenger RNA. These anti-sense or ribozyme sequences will block the expression of specific viral genes and abort the viral infection without damaging the infected cell. Another approach somewhat similar to the ant-sense approaches is to overexpress the target sequences for these regulatory HIV sequences.

Gene therapy efforts would be directed at lowering the risk factors associated with atherosclerosis. Overexpression of the LDL receptor gene would lower blood cholesterol in patients not only with familial hypercholesteremia but with other causes of high cholesterol levels. The genes encoding the proteins for HDL ("the good cholesterol") could be expressed also in various tissues. This would raise HDL levels and prevent atherosclerosis and heart attacks. Tissue plasminogen activator (tPA) protein is being given to patients immediately after their myocardial infarction to digest the blood clots and open up the blocked coronary blood vessels. The gene for tPA could be expressed in the endothelial cells lining the coronary blood vessels and thereby deliver the tPA locally without providing tPA throughout the body. Another approach for coronary vessel disease is to express a gene in the heart that produces a protein that causes new blood vessels to grow. This would increase collateral blood flow and prevent a myocardial infarction from occurring.

Neurodegenerative disorders such as Parkinson's and Alzheimer's diseases are good candidates for early attempts at gene therapy. Arthritis could also be treated by gene therapy. Several proteins and their genes (such as the IL-1 receptor antagonist protein) have recently been discovered to be anti-inflammatory. Expression of these genes in joint (synovial) fluid would decrease the joint inflammation and treat the arthritis.

In addition, methods are being developed to directly modify the sequence of target genes and chromosomal DNA. The delivery of a nucleic acid or other compound that modifies the genetic instruction (e.g., by homologous recombination) can correct a mutated gene or mutate a functioning gene.

Polymers for Drug and Nucleic Acid Delivery

Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to the cells is the use of DNA-polycation complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective. The following are some important principles involving the mechanism by which polycations facilitate uptake of DNA:

Polycations provide attachment of DNA to the cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a convenient linker for attaching specific ligands to DNA and as result, DNA-polycation complexes can be targeted to specific cell types.

Polycations protect DNA in complexes against nuclease degradation. This is important for both extra—and intracellular preservation of DNA. Gene expression is also enabled or increased by preventing endosome acidification with $NH_4Cl$ or chloroquine. Polyethylenimine, which facilitates gene expression without additional treatments, probably disrupts endosomal function itself. Disruption of endosomal function has also been accomplished by linking to the polycation endosomal-disruptive agents such as fusion peptides or adenoviruses.

Polycations can also facilitate DNA condensation. The volume which one DNA molecule occupies in a complex with polycations is drastically lower than the volume of a free DNA molecule. The size of a DNA/polymer complex is probably critical for gene delivery in vivo. In terms of intravenous injection, DNA needs to cross the endothelial barrier and reach the parenchymal cells of interest. The largest endothelia fenestrae (holes in the endothelial barrier) occur in the liver and have an average diameter of 100 nm. The trans-epithelial pores in other organs are much smaller, for example, muscle endothelium can be described as a structure which has a large number of small pores with a radius of 4 nm, and a very low number of large pores with a radius of 20–30 nm. The size of the DNA complexes is also important for the cellular uptake process. After binding to the cells the DNA-polycation complex should be taken up by endocytosis. Since the endocytic vesicles have a homogenous internal diameter of about 100 nm in hepatocytes and are of similar size in other cell types, DNA complexes smaller than 100 nm are preferred.

Condensation of DNA

A significant number of multivalent cations with widely different molecular structures have been shown to induce condensation of DNA.

Two approaches for compacting (used herein as an equivalent to the term condensing) DNA:

1. Multivalent cations with a charge of three or higher have been shown to condense DNA. These include spermidine, spermine, $Co(NH_3)_6^{3+}$, $Fe^{3+}$, and natural or synthetic polymers such as histone H1, protamine, polylysine, and polyethylenimine. Analysis has shown DNA condensation to be favored when 90% or more of the charges along the sugar-phosphate backbone are neutralized.

2. Polymers (neutral or anionic) which can increase repulsion between DNA and its surroundings have been shown to compact DNA. Most significantly, spontaneous DNA self-assembly and aggregation process have been shown to result from the confinement of large amounts of DNA, due to excluded volume effect.

Depending upon the concentration of DNA, condensation leads to three main types of structures:

1) In extremely dilute solution (about 1 μg/mL or below), long DNA molecules can undergo a monomolecular collapse and form structures described as toroid.

2) In very dilute solution (about 10 μg/mL) microaggregates form with short or long molecules and remain in suspension. Toroids, rods and small aggregates can be seen in such solution.

3) In dilute solution (about 1 mg/mL) large aggregates are formed that sediment readily.

Toroids have been considered an attractive form for gene delivery because they have the smallest size. While the size of DNA toroids produced within single preparations has been shown to vary considerably, toroid size is unaffected by the length of DNA being condensed. DNA molecules from 400 bp to genomic length produce toroids similar in size. Therefore one toroid can include from one to several DNA molecules. The kinetics of DNA collapse by polycations that resulted in toroids is very slow. For example DNA condensation by $Co(NH_3)_6Cl_3$ needs 2 hours at room temperature.

The mechanism of DNA condensation is not clear. The electrostatic force between unperturbed helices arises primarily from a counterion fluctuation mechanism requiring multivalent cations and plays a major role in DNA condensation. The hydration forces predominate over electrostatic forces when the DNA helices approach closer then a few water diameters. In a case of DNA-polymeric polycation interactions, DNA condensation is a more complicated process than the case of low molecular weight polycations. Different polycationic proteins can generate toroid and rod formation with different size DNA at a ratio of positive to negative charge of two to five. T4 DNA complexes with polyarginine or histone can form two types of structures; an elongated structure with a long axis length of about 350 nm (like free DNA) and dense spherical particles. Both forms exist simultaneously in the same solution. The reason for the co-existence of the two forms can be explained as an uneven distribution of the polycation chains among the DNA molecules. The uneven distribution generates two thermodynamically favorable conformations.

The electrophoretic mobility of DNA-polycation complexes can change from negative to positive in excess of polycation. It is likely that large polycations don't completely align along DNA but form polymer loops that interact with other DNA molecules. The rapid aggregation and strong intermolecular forces between different DNA molecules may prevent the slow adjustment between helices needed to form tightly packed orderly particles.

As previously stated, preparation of polycation-condensed DNA particles is of particular importance for gene therapy, more specifically, particle delivery such as the design of non-viral gene transfer vectors. Optimal transfection activity in vitro and in vivo can require an excess of polycation molecules. However, the presence of a large excess of polycations may be toxic to cells and tissues. Moreover, the non-specific binding of cationic particles to all cells forestalls cellular targeting. Positive charge also has an adverse influence on biodistribution of the complexes in vivo.

Several modifications of DNA-cation particles have been created to circumvent the nonspecific interactions of the DNA-cation particle and the toxicity of cationic particles. Examples of these modifications include attachment of steric stabilizers, e.g. polyethylene glycol, which inhibit nonspecific interactions between the cation and biological polyanions. Another example is recharging the DNA particle by the additions of polyanions which interact with the cationic particle, thereby lowering its surface charge, i.e. recharging of the DNA particle U.S. Ser. No. 09/328,975. Another example is cross-linking the polymers and thereby caging the complex U.S. Ser. No. 08/778,657, now U.S. Pat. No. 6,126,964, U.S. Ser. No. 09/000,692, now U.S. Pat. No. 6,339,067, U.S. Ser. No. 97/24089, U.S. Ser. No. 09/070299, abandoned, and U.S. Ser. No. 09/464,871. Nucleic acid particles can be formed by the formation of chemical bonds and template polymerization U.S. Ser. No. 08/778,657, now U.S. Pat. No. 6,126,964, U.S. Ser. No. 09/000,692, now U.S. Pat. No. 6,339,067, U.S. Ser. No. 97/24089, U.S. Ser. No. 09/070299, abandoned, and U.S. Ser. No. 09/464,871, abandoned.

A problem with these modifications is that they are most likely irreversible rendering the particle unable to interact with the cell to be transfected, and/or incapable of escaping from the lysosome once taken into a cell, and/or incapable of entering the nucleus once inside the cell. A method for formation of DNA particles that is reversible under conditions found in the cell may allow for effective delivery of DNA. The conditions that cause the reversal of particle formation may be, but not limited to, the pH, ionic strength, oxidative or reductive conditions or agents, or enzymatic activity.

DNA Template Polymerization

Low molecular weight cations with valency, i.e. charge, <+3 fail to condense DNA in aqueous solutions under normal conditions. However, cationic molecules with the charge <+3 can be polymerized in the presence of DNA and the resulting polymers can cause DNA to condense into compact structures. Such an approach is known in synthetic polymer chemistry as template polymerization. During this process, monomers (which are initially weakly associated with the template) are positioned along template's backbone, thereby promoting their polymerization. Weak electrostatic association of the nascent polymer and the template becomes stronger with chain growth of the polymer. Trubetskoy et al used two types of polymerization reactions to achieve DNA condensation: step polymerization and chain polymerization (V S Trubetskoy, V G Budker, L J Hanson, P M Slattum, J A Wolff, L E Hagstrom. Nucleic Acids Res. 26:4178–4185, 1998) U.S. Ser. No. 08/778,657, now U.S. Pat. No. 6,126,964, U.S. Ser. No. 09/000,692, now U.S. Pat. No. 6,339,067, U.S. Ser. No. 97/24089, U.S. Ser. No. 09/070299, abandoned, and U.S. Ser. No. 09/464,871, abandoned. Bis(2-aminoethyl)-1,3-propanediamine (AEPD), a tetramine with 2.5 positive charges per molecule at pH 8 was polymerized in the presence of plasmid DNA using cleavable disulfide amino-reactive cross-linkers dithiobis (succinimidyl propionate) and dimethyl-3,3'-dithiobispropionimidate. Both reactions yielded DNA/polymer complexes with significant retardation in agarose electrophoresis gels demonstrating significant binding and DNA condensation. Treatment of the polymerized complexes with 100 mM dithiothreitol (DTT) resulted in the pDNA returning to its normal supercoiled position following electrophoresis proving thus cleavage the backbone of the. The template dependent polymerization process was also tested using a 14 mer peptide encoding the nuclear localizing signal (NLS) of SV40 T antigen (SEQ ID NO: 1) as a cationic "macromonomer". Other studies included pegylated comonomer (PEG-AEPD) into the reaction mixture and resulted in "worm"-like structures (as judged by transmission electron microscopy) that have previously been observed with DNA complexes formed from block co-polymers of polylysine and PEG (M A Wolfert, E H Schacht, V Toncheva, K Ulbrich, O Nazarova, L W Seymour. Human Gene Ther. 7:2123–2133, 1996). Blessing et al used bisthiol derivative of spermine and reaction of thiol-disulfide exchange to promote chain growth. The presence of DNA accelerated the polymerization reaction as measured the rate of disappearance of free thiols in the reaction mixture (T Blessing, J S Remy, J P Behr. J. Am. Chem. Soc. 120:8519–8520, 1998).

"Caging" of Polycation-Condensed DNA Particles.

The stability of DNA nanoassemblies based on DNA condensation is generally low in vivo because they easily engage in polyion exchange reactions with strong polyanions. The process of exchange consists of two stages: 1) rapid formation of a triple DNA-polycation-polyanion complex, 2) slow substitution of one same-charge polyion with another. At equilibrium conditions, the whole process eventually results in formation of a new binary complex and an excess of a third polyion. The presence of low molecular weight salt can greatly accelerate such exchange reactions, which often result in complete disassembly of condensed DNA particles. Hence, it is desirable to obtain more colloidally stable structures where DNA would stay in its condensed form in complex with corresponding polycation independently of environment conditions.

The complete DNA condensation upon neutralization of only 90% of the polymer's phosphates results in the presence of unpaired positive charges in the DNA particles. If the polycation contains such reactive groups, such as primary amines, these unpaired positive charges may be modified. This modification allows practically limitless possibilities of modulating colloidal properties of DNA particles via chemical modifications of the complex. We have demonstrated the utility of such reactions using traditional DNA-poly-L-lysine (DNA/PLL) system reacted with the cleavable crosslinking reagent dimethyl-3,3'-dithiobispropionimidate (DTBP) which reacts with primary amino groups with formation of amidines (V S Trubetskoy, A Loomis, P M Slattum, J E Hagstrom, V G Budker, J A Wolff. Bioconjugate Chem. 10:624–628, 1999) U.S. Ser. No. 08/778,657, now U.S. Pat. No. 6,126,964, U.S. Ser. No. 09/000,692, now U.S. Pat. No. 6,339,067, U.S. Ser. No. 97/24089, U.S. Ser. No. 09/070299, abandoned, and U.S. Ser. No. 09/464,871, abandoned. Similar results were achieved with other polycations including poly(allylamine) and histone H1. The use of another bifucntional reagent, glutaraldehyde, has been described for stabilization of DNA complexes with cationic peptide CWK18 (R C Adam, K G Rice. J. Pharm. Sci. 739–746, 1999).

Recharging.

The caging approach described above could lead to more colloidally stable DNA assemblies. However, this approach may not change the particle surface charge. Caging with bifunctional reagents, which preserve positive charge of amino group, keeps the particle positive. However, negative surface charge would be more desirable for many practical applications, i.e. in vivo delivery. The phenomenon of surface recharging is well known in colloid chemistry and is described in great detail for lyophobic/lyophilic systems (for example, silver halide hydrosols). Addition of polyion to a suspension of latex particles with oppositely-charged surface leads to the permanent absorption of this polyion on the surface and, upon reaching appropriate stoichiometry, changing the surface charge to opposite one. This whole process is salt dependent with flocculation to occur upon reaching the neutralization point.

We have demonstrated that similar layering of polyelectrolytes can be achieved on the surface of DNA/polycation particles (V S Trubetskoy, A Loomis, J E Hagstrom, V G Budker, J A Wolff. Nucleic Acids Res. 27:3090–3095, 1999). The principal DNA-polycation (DNA/pC) complex used in this study was DNA/PLL (1:3 charge ratio) formed in low salt 25 mM HEPES buffer and recharged with increasing amounts of various polyanions. The DNA particles were characterized after addition of a third polyion component to a DNA/polycation complex using a new DNA condensation assay (V S Trubetskoy, P M Slattum, J E Hagstrom, J A Wolff, V G Budker. Anal. Biochem. 267:309–313, 1999) and static light scattering. It has been found that certain polyanions such as poly(methacrylic acid) and poly(aspartic acid) decondensed DNA in DNA/PLL complexes. Surprisingly, polyanions of lower charge density such as succinylated PLL and poly(glutamic acid), even when added in 20-fold charge excess to condensing polycation (PLL) did not decondense DNA in DNA/PLL (1:3) complexes. Further studies have found that displacement effects are salt-dependent. In addition, poly-L-glutamic acid but not the relatively weaker polyanion succinylated poly-L-lysine (SPLL) displaces DNA at higher sodium chloride concentrations. Measurement of $\zeta$-potential of DNA/PLL particles during titration with SPLL revealed the change of particle surface charge at approximately the charge equivalency point. Thus, it can be concluded that addition of low charge density polyanion to the cationic DNA/PLL particles results in particle surface charge reversal while maintaining condensed DNA core intact. Finally, DNA/polycation complexes can be both recharged and crosslinked or caged U.S. Ser. No. 08/778,657, U.S. Ser. No. 09/000,692, U.S. Ser. No. 97/24089, U.S. Ser. No. 09/070299, and U.S. Ser. No. 09/464,871.

The Use of pH-Sensitive Lipids, Amphipathic Compounds, and Liposomes for Drug and Nucleic Acid Delivery After the landmark description of DOTMA (N-[1-(2,3-dioleyloxy)propyl]-N,N,N-trimethylammonium chloride) [Felgner, P L, Gadek, T R, Holm, M, et al. Lipofection: a highly efficient, lipid-mediated DNA-transfection procedure. Proc. Natl. Acad. Sci. USA. 1987;84:7413–7417], a plethora of cationic lipids have been synthesized. Basically, all the cationic lipids are amphipathic compounds that contain a hydrophobic domain, a spacer, and positively-charged amine. The hydrophobic domains are typically hydrocarbon chains such as fatty acids derived from oleic or myristic acid. The hydrocarbon chains are often joined either by ether or ester bonds to a spacer such as glycerol. Quaternary amines often compose the cationic groups. Usually, the cationic lipids are mixed with a fusogenic lipid such as DOPE (dioleoyl phosphatidyl ethanolamine) to form liposomes. The mixtures are mixed in chloroform that is then dried. Water is added to the dried lipid film and unilamellar liposomes form during sonication. Multilamellar cationic liposomes and cationic liposomes/DNA complexes prepared by the reverse-phase evaporation method have also been used for transfection. Cationic liposomes have also been prepared by an ethanol injection technique.

Several cationic lipids contain a spermine group for binding to DNA. DOSPA, the cationic lipid within the LipofectAMINE formulation (Life Technologies) contains a spermine linked via a amide bond and ethyl group to a trimethyl, quaternary amine [Hawley-Nelson, P, Ciccarone, V and Jessee, J. Lipofectamine reagent: A new, higher efficiency polycationic liposome transfection reagent. *Focus* 1993;15:73–79]. A French group has synthesized a series of cationic lipids such as DOGS (dioctadecylglycinespermine) that contain spermine [Remy, J-S, Sirlin, C, Vierling, P, et al. Gene transfer with a series of lipophilic DNA-binding molecules. *Bioconjugate Chem.* 1994;5:647–654]. DNA has also been transfected by lipophilic polylysines which contain dipalmotoylsuccinylglycerol chemically-bonded to low molecular weight (~3000 MW) polylysine [Zhou, X, Kilbanov, A and Huang, L. Lipophilic polylysines mediate efficient DNA transfection in mammalian cells. *Biochim. Biophys. Acta* 1991;1065:8–14. Zhou, X and Huang, L. DNA transfection mediated by cationic liposomes containing lipopolylysine: Characterization and mechanism of action. *Biochim. Biophys. Acta* 1994; 1195–203].

Other studies have used adjuvants with the cationic liposomes. Transfection efficiency into Cos cells was increased when amphiphilic peptides derived from influenza virus hemagglutinin were added to DOTMA/DOPE liposomes [Kamata, H, Yagisawa, H, Takahashi, S, et al. Amphiphilic peptides enhance the efficiency of liposome-mediated DNA transfection. *Nucleic Acids Res.* 1994;22:536–537]. Cationic lipids have been combined with galactose ligands for targeting to the hepatocyte asialoglycoprotein receptor [Remy, J-S, Kichler, A, Mordvinov, V, et al. Targeted gene transfer into hepatoma cells with lipopolyamine-condensed DNA particles presenting galactose ligands: A stage toward artificial viruses. *Proc. Natl. Acad. Sci. USA* 1995;92:1744–1748]. Thiol-reactive phospholipids have also been incorporated into cationic lipid/pDNA complexes to enable cellular binding even when the net charge of the complex is not positive [Kichler, A, Remy, J-S, Boussif, O, et al. Efficient gene delivery with neutral complexes of lipospermine and thiol-reactive phospholipids. *Biochem. Biophys. Res. Comm.* 1995;209:444–450]. DNA-dependent template process converted thiol-containing detergent possessing high critical micelle concentration into dimeric lipid-like molecule with apparently low water solubility.

Cationic liposomes may deliver DNA either directly across the plasma membrane or via the endosome compartment. Regardless of its exact entry point, much of the DNA within cationic liposomes does accumulate in the endosome compartment. Several approaches have been investigated to prevent loss of the foreign DNA in the endosomal compartment by protecting it from hydrolytic digestion within the endosomes or enabling its escape from endosomes into the cytoplasm. They include the use of acidotropic (lysomotrophic), weak amines such as chloroquine that presumably prevent DNA degradation by inhibiting endosomal acidification [Legendre, J. & Szoka, F. Delivery of plasmid DNA into mammalian cell lines using pH-sensitive liposomes: Comparison with cationic liposomes. *Pharmaceut. Res.* 9, 1235–1242 (1992)]. Viral fusion peptides or whole virus have been included to disrupt endosomes or promote fusion of liposomes with endosomes, and facilitate release of DNA into the cytoplasm [Kamata, H., Yagisawa, H., Takahashi, S. & Hirata, H. Amphiphilic peptides enhance the efficiency of liposome-mediated DNA transfection. *Nucleic Acids Res.* 22, 536–537 (1994). Wagner, E., Curiel, D. & Cotten, M. Delivery of drugs, proteins and genes into cells using transferrin as a ligand for receptor-mediated endocytosis. *Advanced Drug Delivery Reviews* 14,113–135 (1994)].

Knowledge of lipid phases and membrane fusion has been used to design potentially more versatile liposomes that exploit the endosomal acidification to promote fusion with endosomal membranes. Such an approach is best exemplified by anionic, pH-sensitive liposomes that have been designed to destabilize or fuse with the endosome membrane at acidic pH [Duzgunes, N., Straubinger, R. M., Baldwin, P. A. & Papahadjopoulos, D. *PH-sensitive liposomes.* (eds Wilschub, J. & Hoekstra, D.) p. 713–730 (Marcel Deker INC, 1991)]. All of the anionic, pH-sensitive liposomes have utilized phosphatidylethanolamine (PE) bilayers that are stabilized at non-acidic pH by the addition of lipids that contain a carboxylic acid group. Liposomes containing only PE are prone to the inverted hexagonal phase ($H_{II}$). In pH-sensitive, anionic liposomes, the carboxylic acid's negative charge increases the size of the lipid head group at pH greater than the carboxylic acid's $pK_a$ and thereby stabilizes the phosphatidylethanolamine bilayer. At acidic pH conditions found within endosomes, the uncharged or reduced charge species is unable to stabilize the phosphatidylethanolamine-rich bilayer. Anionic, pH-sensitive liposomes have delivered a variety of membrane-impermeable compounds including DNA. However, the negative charge of these pH-sensitive liposomes prevents them from efficiently taking up DNA and interacting with cells; thus decreasing their utility for transfection. We have described the use of cationic, pH-sensitive liposomes to mediate the efficient transfer of DNA into a variety of cells in culture U.S. Ser. No. 08/530,598, now U.S. Pat. No. 5,744,335, and U.S. Ser. No. 09/020,566, now U.S. Pat. No. 6,180,784.

The Use of pH-Sensitive Polymers for Drug and Nucleic Acid Delivery

Polymers that pH-sensitive are have found broad application in the area of drug delivery exploiting various physiological and intracellular pH gradients for the purpose of controlled release of drugs (both low molecular weight and polymeric). pH sensitivity can be broadly defined as any change in polymer's physico-chemical properties over certain range of pH. More narrow definition demands significant changes in the polymer's ability to retain (release) a bioactive substance (drug) in a physiologically tolerated pH range (usually pH 5.5–8). pH-sensitivity presumes the presence of ionizable groups in the polymer (polyion). All polyions can be divided into three categories based on their ability to donate or accept protons in aqueous solutions: polyacids, polybases and polyampholytes. Use of pH-sensitive polyacids in drug delivery applications usually relies on their ability to become soluble with the pH increase (acid/salt conversion), to form complex with other polymers over change of pH or undergo significant change in hydrophobicity/hydrophilicity balance. Combinations of all three above factors are also possible.

Copolymers of polymethacrylic acid (Eudragit S, Rohm America) are known as polymers which are insoluble at lower pH but readily solubilized at higher pH, so they are used as enteric coatings designed to dissolve at higher intestinal pH (Z Hu et al. J. Drug Target., 7, 223, 1999). A typical example of pH-dependent complexation is copolymers of polyacrylate(graft)ethyleneglycol which can be formulated into various pH-sensitive hydrogels which exhibit pH-dependent swelling and drug release (F Madsen et al., Biomaterials, 20, 1701, 1999). Hydrophobically-modified N-isopropylacrylamide-methacrylic acid copolymer can render regular egg PC liposomes pH-sensitive by pH-dependent interaction of grafted aliphatic chains with lipid bilayer (O Meyer et al., FEBS Lett., 421, 61, 1998). Polymers with pH-mediated hydrophobicity (like polyethylacrylic acid) can be used as endosomal disrupters for cytoplasmic drug delivery (Murthy, N., Robichaud, J. R., Tirrell, D. A., Stayton, P. S., Hoffman, A. S. J. Controlled Release 61, 137, 1999).

Polybases have found broad applications as agents for nucleic acid delivery in transfection/gene therapy applications due to the fact they are readily interact with polyacids. A typical example is polyethyleneimine (PEI). This polymer secures nucleic acid electrostatic adsorption on the cell surface followed by endocytosis of the whole complex. Cytoplasmic release of the nucleic acid occurs presumably via the so called "proton sponge" effect according to which pH-sensitivity of PEI is responsible for endosome rupture due to osmotic swelling during its acidification (O Boussif et al. Proc. Natl. Acad. Sci. USA 92, 7297, 1995). Cationic acrylates possess the similar activity (for example, poly-((2-dimethylamino)ethyl methacrylate) (P van de Wetering et al. J. Controlled Release 64, 193, 2000). However, polybases due to their polycationic nature pH-sensitive polybases have not found broad in vivo application so far, due to their acute systemic toxicity in vivo (J H Senior, Biochim. Biophys. Acta, 1070, 173, 1991). Milder polybases (for example, linear PEI) are better tolerated and can be used systemically for in vivo gene transfer (D Goula et al. Gene Therapy 5, 712, 1998).

Membrane Active Compounds

Many biologically active compounds, in particular large and/or charged compounds, are incapable of crossing biological membranes. In order for these compounds to enter cells, the cells must either take them up by endocytosis, into endosomes, or there must be a disruption of the cellular membrane to allow the compound to cross. In the case of endosomal entry, the endosomal membrane must be disrupted to allow for the entrance of the compound in the interior of the cell. Therefore, either entry pathway into the cell requires a disruption of the cellular membrane. There exist compounds termed membrane active compounds that disrupt membranes. One can imagine that if the membrane active agent were operative in a certain time and place it would facilitate the transport of the biologically active compound across the biological membrane. The control of when and where the membrane active compound is active is crucial to effective transport. If the membrane active compound is too active or active at the wrong time, then no transport occurs or transport is associated with cell rupture and thereby cell death. Nature has evolved various strategies to allow for membrane transport of biologically active compounds including membrane fusion and the use membrane active compounds whose activity is modulated such that activity assists transport without toxicity. Many lipid-based transport formulations rely on membrane fusion and some membrane active peptides' activities are modulated by pH. In particular, viral coat proteins are often pH-sensitive, inactive at neutral or basic pH and active under the acidic conditions found in the endosome.

Small Molecular Endosomolytic Agents

A cellular transport step that has attracted attention for gene transfer is that of DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. A number of chemicals such as chloroquine, bafilomycin or Brefeldin A1 have been used to disrupt or modify the trafficking of molecules through intracellular pathways. Chloroquine decreases the acidification of the endosomal and lysosomal compartments but also affects other cellular functions. Brefeldin A, an isoprenoid fungal metabolite, collapses reversibly the Golgi apparatus into the endoplasmic reticulum and the early endosomal compartment into the trans-Golgi network (TGN) to form tubules. Bafilomycin $A_1$, a macrolide antibiotic is a more specific inhibitor of endosomal acidification and vacuolar type $H^+$-ATPase than chloroquine.

Viruses, Proteins and Peptides for Disruption of Endosomes and Endosomal Function Viruses such as adenovirus have been used to induce gene release from endosomes or other intracellular compartments (D. Curiel, Agarwal, S., Wagner, E., and Cotten, M. PNAS 88:8850, 1991). Rhinovirus has also been used for this purpose (W. Zauner et al. J. Virology 69:1085–92, 1995). Viral components such as influenza virus hemagglutinin subunit HA-2 analogs has also been used to induce endosomal release (E. Wagner et al. PNAS 89:7934, 1992). Amphipathic peptides resembling the N-terminal HA-2 sequence has been studied (K. Mechtler and E. Wagner, New J. Chem. 21:105–111, 1997). Parts of the pseudonmonas exotoxin and diptheria toxin have also been used for drug delivery (I. Pastan and D. FitzGerald. J. Biol. Chem. 264: 15157, 1989).

A variety of synthetic amphipathic peptides have been used to enhance transfection of genes (N. Ohmori et al. Biochem. Biophys. Res. Commun. 235:726, 1997). The ER-retaining signal (KDEL sequence) has been proposed to enhance delivery to the endoplasmic reticulum and prevent delivery to lysosomes (S. Seetharam et al. J. Biol. Chem. 266:17376, 1991).

The present invention provides for a new group of membrane active compounds that can enhance the delivery of nucleic acids.

Other Cellular and Intracellular Gradients Useful for Delivery

Nucleic acid and gene delivery may involve the biological pH gradient that is active within organisms as a factor in delivering a polynucleotide to a cell. Different pathways that may be affected by the pH gradient include cellular transport mechanisms, endosomal disruption/breakdown, and particle disassembly (release of the DNA). Other gradients that can be useful in gene therapy research involve ionic gradients that are related to cells. For example, both $Na^+$ and $K^+$ have large concentration gradients that exist across the cell membrane. Systems containing metal-binding groups can utilize such gradients to influence delivery of a polynucleotide to a cell. Changes in the osmotic pressure in the endosome also have been used to disrupt membranes and allow for transport across membrane layer. Buffering of the endosome pH may cause these changes in osmotic pressure. For example, the "proton sponge" effect of PEI (O Boussif et al. Proc. Natl. Acad. Sci. USA 92, 7297, 1995) and certain polyanions (Murthy, N., Robichaud, J. R., Tirrell, D. A., Stayton, P. S., Hoffman, A. S. Journal of Controlled Release 1999, 61, 137) are postulated to cause an increase in the ionic strength inside of the endosome, which causes a increase in osmotic pressure. This pressure increase results in membrane disruption and release of the contents of the endosome.

In addition to pH and other ionic gradients, there exist other difference in the chemical environment associated with cellular activities that may be used in gene delivery. In particular enzymatic activity both extra and intracellularly may be used to deliver the gene of interest either by aiding in the delivery to the cell or escape from intracellular compartments. Proteases, found in serum, lysosome and cytoplasm, may be used to disrupt the particle and allow its interaction with the cell surface or cause it fracture the intracellular compartment, e.g. endosome or lysosome, allowing the gene to be released intracellularly.

SUMMARY

Compounds and methods are described for enhancing the delivery of biologically active compounds including peptides, small molecular drugs and nucleic acids. Novel pH-labile and membrane active compounds are described. Some of these compounds are cleaved at acidic pH; thereby increasing their membrane activity. Some of these novel compounds also have use as detergents.

DETAILED DESCRIPTION

The present invention relates to the delivery of desired compounds (e.g., drugs and nucleic acids) into cells using pH-labile polymers and membrane active compounds coupled with labile compounds. The present invention provides compositions and methods for delivery and release of a compound of interest to a cell.

Noncovalent molecule-molecule interactions, which are the basis of DNA-polycation particle formation, rely on discreet interactions between the functional groups on the interacting molecules. It is quite apparent that if one modifies the interacting functional groups, one changes the whole molecule-molecule interaction. This is true for small molecules and large macromolecules. For example methyl alcohol is a liquid capable of hydrogen bonding with water, which confers the compound with water solubility. In contrast, conversion of the alcohol functional group to a methyl ether to form dimethyl ether renders the molecule in to a water insoluble gas. Many other examples may be observed in small molecular weight drug-receptor interactions. DNA interacts with the polycation poly-L-lysine to form condensed DNA particles. If the amino groups of poly-L-lysine are converted to carboxylate groups as in succinylated poly-L-lysine there is no interaction with the polyanion DNA. The identities of the functional groups on a molecule dictate its interactions with other molecules. Therefore, the ability to control the identity of the function groups on a molecule allows one to control its interactions. As a consequence, controlled and reversible functional group modification is important if one want to modulate a molecule's interactions. This control is of particular importance when the molecule in question is biologically active. For example, one may not want to administer cytotoxic drugs directly. In this case, one may administer a prodrug that is itself inactive, but becomes active by change(s) in functional group(s) after delivery.

Prior to the present invention, delivery systems suffered from slow reversibility—or irreversibility—and/or high toxicity. For example, many cationic polymers such as poly-L-lysine (PLL) and polyethylenimine (PEI) form positively charged condensed particles with DNA. In vitro, these particles are relatively good reagents, compared to DNA alone, for the transfer of DNA into cells. However, these particles are poor transfer reagents in vivo due to their toxicity and relatively stable interaction with DNA, which renders their complexation irreversible under physiological conditions. There are several barriers that these complexes must overcome for them to be efficient gene transfer reagents: stable enough to protect the DNA from nucleases and aid in delivery to the cell, yet the DNA polycation complex must be disrupted—thereby allowing transcription to occur. Additionally, if the complex is taken into the cell through the process of endocytosis, the complex must escape the endosome before being taken into the lysosome and being digested.

To increase the stability of DNA particles in serum, certain embodiments of the present invention provide polyanions that form a third layer in the DNA-polycation complex and it is negatively charged. To assist in the disruption of the DNA complexes, certain embodiments of the present invention provide synthesized polymers that are cleaved in the acid conditions found in the endosome (i.e., pH 5–7). For example, the present invention provides for the cleavage or alteration of a labile chemical group once the complex is in the desired environment: cleavage of the polymer backbone resulting in smaller polyions or cleavage of the link between the polymer backbone and the ion resulting in an ion and an polymer. In either case, the number of molecules in the endosome increases. This alteration may facilitate the release of the delivered compound into the cytoplasm. Although it is not necessary to understand the mechanism in order to use the present invention, and it is not intended that the present invention be so limited, one can contemplate a number of mechanisms by which the delivery is enhanced by the present invention. In some instances cleavage of the labile polymer leads to release and enhanced delivery of the therapeutic agent (biologically active compound). Cleavage can also lead to enhanced membrane activity so that the pharmaceutical (biologically active compound) is more effectively delivered to the cell. This can occur in the environs of a tumor or inflamed tissue or within an acidic sub-cellular compartment. Cleavage can also cause an osmotic shock to the endosomes and disrupts the endosomes. If the polymer backbone is hydrophobic it may interact with the membrane of the endosome. Either effect disrupts the endosome and thereby assists in release of delivered compound.

In some embodiments of the present invention, membrane active agents are complexed with the delivery system such that they are inactive and not membrane active within the complex but become active when released, following the chemical conversion of the labile group. The membrane active agents may be used to assist in the disruption of the endosome or other cellular compartment. They can also be used to enable selective delivery or toxicity to tumors or tissues that are acidic. Many membrane active agents such as the peptides melittin and pardaxin and various viral proteins and peptides are effective in allowing a disruption of cellular compartments such as endosomes to effect a release of its contents into a cell. However, these agents are toxic to cells both in vitro and in vivo due to the inherent nature of their membrane activity. To decrease the toxicity of these agents, the present invention provides techniques to complex or modify the agent in a way which blocks or inhibits the membrane activity of the agent but is reversible in nature so activity can be recovered when membrane activity is needed for transport of biologically active compound. The activities of these membrane active agents can be controlled in a number of different ways. For example, a modification of the agent may be made that can be cleaved off of the agent allowing the activity to return. The cleavage can occur during a natural process, such as the pH drop seen in endosomes or cleaved in the cytoplasm of cells where amounts of reducing agents become available. Cleavage of a blocking agent can occur by delivery of a cleaving agent to the blocked complex at a time when it would be most beneficial. Another exemplary method of blocking membrane active agents is to reversibly modify the agents' functional group with an activity blocking addition (defined as "Compounds or Chemical Moieties that Inhibit or Block the Membrane Activity of Another Compound or Chemical Moiety". When the blocking addition reaches an environment or an adjunct is added the reversible modification is reversed and the membrane active agent will regain activity.

In some embodiments the biologically active compound is reversibly modified, or complexed with, an interaction modifier such that the interactions between the biologically active molecule and its environs, that is its interactions with itself and other molecules, is altered when the interaction modifier is released. For example attachment of such nonionic hydrophilic groups such as polyethylene glycol and polysaccharides (e.g. starch) may decrease self-association and interactions with other molecules such as serum compounds and cellular membranes, which may be necessary for transport of the biologically active molecule to the cell. However these molecules may inhibit cellular uptake and therefore, must be lost before cellular uptake can occur. Likewise, cell targeting ligands aid in transport to a cell but may not be necessary, and may inhibit, transport into a cell. In all of these cases, the reversible attachment of the interaction modifier, through a labile bond, would be beneficial.

The present invention provides for the transfer of polynucleotides, and other biologically active compounds into cells in culture (also known as "in vitro"). Compounds or kits for the transfection of cells in culture is commonly sold as "transfection reagents" or "transfection kits". The present invention also provides for the transfer of polynucleotides, and biologically active compounds into cells within tissues in situ and in vivo, and delivered intravasculary (U.S. patent application Ser. No. 08/571,536, abandoned), intrarterially, intravenous, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thryoid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. Compounds for the transfection of cells in vivo in a whole organism can be sold as "in vivo transfection reagents" or "in vivo transfection kits" or as a pharmaceutical for gene therapy.

Polymers with pH-Labile Bonds

The present invention provides a wide variety of polymers with labile groups that find use in the delivery systems of the present invention. The labile groups are selected such that they undergo a chemical transformation (e.g., cleavage) when present in physiological conditions. The chemical transformation may be initiated by the addition of a compound to the cell or may occur spontaneously when introduced into intra-and/or extra-cellular environments (e.g., the lower pH conditions of an endosome or the extracellular space surrounding tumors). The conditions under which a labile group will undergo transformation can be controlled by altering the chemical constituents of the molecule containing the labile group. For example, addition of particular chemical moieties (e.g., electron acceptors or donors) near the labile group can effect the particular conditions (e.g., pH) under which chemical transformation will occur.

In certain embodiments, the present invention provides compound delivery systems composed of polymers (e.g., cationic polymers, anionic polymers, zwitterionic and nonionic polymers) that contain pH-labile groups. The systems are relatively chemically stable until they are introduced into acidic conditions that render them unstable (labile). An aqueous solution is acidic when the concentration of protons ($H^+$) exceed the concentration of hydroxide ($OH^-$). Upon delivery to the desired location, the labile group undergoes an acid-catalyzed chemical transformation resulting in release of the delivered compound or a complex of the delivered compound. The pH-labile bond may either be in the main-chain or in the side chain. If the pH-labile bond occurs in the main chain, then cleavage of the labile bond results in a decrease in polymer length. If the pH-labile bond occurs in the side chain, then cleavage of the labile bond results in loss of side chain atoms from the polymer.

In some preferred embodiments of the present invention, nucleic acids are delivered to cells by a polymer complex containing a labile group, or groups, that undergoes chemical transformation when exposed to the low pH environment of an endosome. Such complexes provide improved nucleic acid delivery systems, as they provide for efficient delivery and low toxicity.

Polymers Containing Several Membrane Active Compounds

The present invention specifies polymers containing more than two membrane active compounds. In one embodiment, the membrane active compounds are grafted onto a preformed polymer to form a comb-type polymer, i.e. a polymer containing side chain groups. In another embodiment, the membrane active compounds are incorporated into the polymer by chain or step polymerization processes. To aid in complexation between DNA and membrane active compounds and/or to augment the membrane activity of membrane active agents, certain embodiments of the present invention have polymers composed of monomers that are themselves membrane active. These polymers are formed by attaching a membrane active compound to a preformed polymer or by polymerization of membrane active monomers.

Membrane Active Compounds Containing Labile Bonds

The inclusion of labile bonds into membrane active compounds increases their versatility in a number of ways. It can reduce their toxicity by enabling their membrane activity to be expressed in specific tissues such as tumors and inflamed joints, specific sub-cellular locations such as endosomes and lysosomes, or under specific conditions such as a reducing environment. In one embodiment of the invention, the labile bonds are pH-sensitive in that the bonds break or are cleaved when pH of their microenvironment drops below physiologic pH of 7.4 or below pH of 6.5 or below pH of 5.5. In another embodiment the labile bonds are very pH-sensitive. In yet another embodiment, the labile bonds are disulfides that are labile under physiologic conditions or that are cleaved by the addition of an exogenous reducing agent. In other embodiments, the labile bonds are acetals, ketals, enol ethers, enol esters, amides of 2,3-disubstituted maleamic acid, imines, imminiums, enamines, silyl ethers, and silyl enol ethers.

The invention also includes compounds that are of the general structure: A-B-C wherein A is a membrane active compound, B is a labile linkage, and C is a compound that inhibits the membrane activity of compound A. Upon cleavage of B, membrane activity is restored to compound A. This cleavage occurs in certain tissue, organ, and sub-cellular locations that are controlled by the microenvironment of the location and also by the addition of exogenous agents. In another embodiment, the invention includes compositions containing biologically active compounds and compounds of the general structure: A-B-C wherein A is a membrane active compound, B is a labile linkage, and C is a compound that inhibits the membrane activity of compound A. The biologically-active compounds include pharmaceutical drugs, nucleic acids and genes. In yet another embodiment, these compounds that are of the general structure—A-B-C wherein A is a membrane active compound, B is a labile linkage, and C is a compound that inhibits the membrane activity of compound A- .are used to deliver biologically active compounds that include pharmaceutical drugs, nucleic acids and genes. In one specific embodiment, these A-B-C compounds are used to deliver nucleic acids and genes to muscle (skeletal, heart, respiratory, striated, and non-striated), liver (hepatocytes), spleen, immune cells, gastrointestinal cells, cells of the nervous system (neurons, glial, and microglial), skin cells (dermis and epidermis), joint and synovial cells, tumor cells, kidney, cells of the immune system (dendiritic, T cells, B cells, antigen-presenting cells, macrophages), exocrine cells (pancreas, salivary glands), prostate, adrenal gland, thyroid gland, eye structures (retinal cells), and respiratory cells (cells of the lung, nose, respiratory tract)

Mixtures of Membrane Active Compounds and Labile Compounds

In addition, the invention is a composition of matter that includes a membrane active compound and a labile compound. In one embodiment, the labile compound inhibits the membrane activity of the membrane active compound. Upon chemical modification of the labile compound, membrane activity is restored to the membrane active compound. This chemical modification occurs in certain tissue, organ, and sub-cellular locations that are controlled by the microenvironment of the location and also by the addition of exogenous agents. In one embodiment the chemical modification involves the cleavage of the polymer. In one embodiment, the membrane active compound and the inhibitory labile compound are polyions and are of opposite charge. For example, the membrane active compound is a polycation and the inhibitory labile compound is a polyanion.

In another embodiment, the invention includes compositions containing biologically active compounds, a membrane active compound and a labile compound. Upon chemical modification of the labile compound, membrane activity is restored to the membrane active compound. This chemical modification occurs in certain tissue, organ, and sub-cellular locations that are controlled by the microenvironment of the location and also by the addition of exogenous agents. In one embodiment the chemical modification involves the cleavage of the polymer. In one specific embodiment, these compositions containing biologically active compounds, a membrane active compound and a labile compound are used to deliver nucleic acids and genes to muscle (skeletal, heart, respiratory, striated, and non-striated), liver (hepatocytes), spleen, immune cells, gastrointestinal cells, cells of the nervous system (neurons, glial, and microglial), skin cells (dermis and epidermis), joint and synovial cells, tumor cells, kidney, cells of the immune system (dendiritic, T cells, B cells, antigen-presenting cells, macrophages), exocrine cells (pancreas, salivary glands), prostate, adrenal gland, thyroid gland, eye structures (retinal cells), respiratory cells (cells of the lung, nose, respiratory tract), and endothelial cells.

Biologically Active Compounds Containing pH-Labile and/or Extremely and/or Very pH-Labile Bonds The invention specifies compounds of the following general structure: A-B-C wherein A is a biologically active compound such as pharmaceuticals, drugs, proteins, peptides, hormones, cytokines, enzymes and nucleic acids such as anti-sense, ribozyme, recombining nucleic acids, and expressed genes; B is a labile linkage that contains a pH-labile bond such as acetals, ketals, enol ethers, enol esters, amides of 2,3-disubstituted maleamic acids, imines, imminiums, enamines, silyl ethers, and silyl enol ethers; and C is a compound. In one embodiment C is a compound that modifies the activity, function, delivery, transport, shelf-life, pharmacokinetics, blood circulation time in vivo, tissue and organ targetting, and sub-cellular targeting of the biologically active compound A. For example, C can be a hydrophilic compound such as polyethylene glycol to increase the water solubility of relatively hydrophobic drugs (e.g. amphotericin B) to improve their formulation and delivery properties. In other embodiments, B is a labile linkage that contains pH-labile bond such as acetals, ketals, enol ethers, enol esters, amides, imines, imminiums, enamines, silyl ethers, and silyl enol ethers.

The invention also specifies that the labile linkage B is attached to reactive functional groups on the biologically active compound A. In yet another embodiment, reactive functional groups are attached to nucleic acids via alkylation. Specifically, nitrogen and sulfur mustards may be used for modify nucleic acids with reactive functional groups.

pH-Labile Amphipathic Compounds

In one specification of the invention, the pH-labile and very pH-labile linkages and bonds are used within amphipathic compounds and detergents. The pH-labile amphipathic compounds can be incorporated into liposomes for delivery of biologically active compounds and nucleic acids to cells. The detergents can be used for cleaning purposes and for modifying the solubility of biologically active compounds such as proteins. The detergents can be in the form of micelles or reverse micelles. Often detergents are used to extract biologically active compounds from natural mixtures. After the extraction procedure is completed, a labile detergent would aid in the separation of the detergent and the biologically active compound. If the detergent is labile under conditions that do not harm the biologically active compound (e.g. destroying or denaturing a protein), then removal of the detergent would be much easier that currently-used methods.

Definitions

To facilitate an understanding of the present invention, a number of terms and phrases are defined below:

Biologically Active Compound

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, enzyme inhibitors, hormones, cytokines, antigens, viruses, oligonucleotides, enzymes and nucleic acids are examples of biologically active compounds.

Peptide and polypeptide refer to a series of amino acid residues, more than two, connected to one another by amide bonds between the beta or alpha-amino group and carboxyl group of contiguous amino acid residues. The amino acids may be naturally occurring or synthetic. Polypeptide includes proteins and peptides, modified proteins and peptides, and non-natural proteins and peptides. Enzymes are proteins evolved by the cells of living organisms for the specific function of catalyzing chemical reactions. A chemical reaction is defined as the formation or cleavage of covalent or ionic bonds. Bioactive compounds may be used interchangeably with biologically active compound for purposes of this application.

Delivery of Biologically Active Compound

The delivery of a biologically active compound is commonly known as "drug delivery". "Delivered" means that the biologically active compound becomes associated with the cell or organism. The compound can be in the circulatory system, intravessel, extracellular, on the membrane of the cell or inside the cytoplasm, nucleus, or other organelle of the cell.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, and bile ducts. The intravascular route includes delivery through the blood vessels such as an artery or a vein. An administration route involving the mucosal membranes is meant to include nasal, bronchial, inhalation into the lungs, or via the eyes. Other routes of administration include intraparenchymal into tissues such as muscle (intramuscular), liver, brain, and kidney. Transdermal routes of administration have been effected by patches and ionotophoresis. Other epithelial routes include oral, nasal, respiratory, and vaginal routes of administration.

Delivery System

Delivery system is the means by which a biologically active compound becomes delivered. That is all compounds, including the biologically active compound itself, that are required for delivery and all procedures required for delivery including the form (such volume and phase (solid, liquid, or gas)) and method of administration (such as but not limited to oral or subcutaneous methods of delivery).

Nucleic Acid

The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nuclei acid includes deoxyribonucleic acid (DNA) and ribonucleic acid (RNA). The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

DNA may be in the form of anti-sense, plasmid DNA, parts of a plasmid DNA, product of a polymerase chain reaction (PCR), vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups.

"Anti-sense" is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothionates, and other variants of the phosphate backbone of native nucleic acids. In addition, DNA and RNA may be single, double, triple, or quadruple stranded.

The term "recombinant DNA molecule" as used herein refers to a DNA molecule that is comprised of segments of DNA joined together by means of molecular biological techniques. "Expression cassette" refers to a natural or recombinantly produced polynucleotide molecule that is capable of expressing protein(s). A DNA expression cassette typically includes a promoter (allowing transcription initiation), and a sequence encoding one or more proteins. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

A nucleic acid can be used to modify the genomic or extrachromosomal DNA sequences. This can be achieved by delivering a nucleic acid that is expressed. Alternatively, the nucleic acid can effect a change in the DNA or RNA sequence of the target cell. This can be achieved by homologous recombination, gene conversion, or other yet to be described mechanisms.

Gene

The term "gene" refers to a nucleic acid (e.g., DNA) sequence that comprises coding sequences necessary for the production of a polypeptide or precursor (e.g., -myosin heavy chain). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form.

Gene Expression

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decreases production. Molecules (e.g., transcription factors) that are involved in up-regulation or down-regulation are often called "activators" and "repressors," respectively.

Delivery of Nucleic Acids

The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The delivery of nucleic acid can lead to modification of the DNA sequence of the target cell.

The polynucleotides or genetic material being delivered are generally mixed with transfection reagents prior to delivery. The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has irreversibly integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA. The term "naked polynucleotides" indicates that the polynucleotides are not associated with a transfection reagent or other delivery vehicle that is required for the polynucleotide to be delivered to a cell.

A "transfection reagent" or "delivery vehicle" is a compound or compounds that bind(s) to or complex(es) with oligonucleotides, polynucleotides, or other desired compounds and mediates their entry into cells. Examples of transfection reagents include, but are not limited to, cationic liposomes and lipids, polyamines, calcium phosphate precipitates, histone proteins, polyethylenimine, and polylysine complexes (polyethylenimine and polylysine are both toxic). Typically, when used for the delivery of nucleic acids, the transfection reagent has a net positive charge that binds to the polynucleotide's negative charge. For example, cationic liposomes or polylysine complexes have net positive charges that enable them to bind to DNA or RNA.

Enzyme

Enzyme is a protein that acts as a catalyst. That is a protein that increases the rate of a chemical reaction without itself undergoing any permanent chemical change. The chemical reactions that are catalyzed by an enzyme are termed enzymatic reactions and chemical reactions that are not are termed nonenzymatic reactions.

Half-Life

The half-life of a chemical reaction is the time required for one half of a given material to undergo a chemical reaction.

Complex

Two molecules are combined, to form a complex through a process called complexation or complex formation, if the are in contact with one another through noncovalent interactions such as electrostatic interactions, hydrogen bonding interactions, and hydrophobic interactions.

Modification

A molecule is modified, to form a modification through a process called modification, by a second molecule if the two become bonded through a covalent bond. That is, the two molecules form a covalent bond between an atom form one molecule and an atom from the second molecule resulting in the formation of a new single molecule. A chemical covalent bond is an interaction, bond, between two atoms in which there is a sharing of electron density.

Osmosis

Osmosis is the passage of a solvent through a semipermeable membrane, a membrane through which solvent can pass but not all solutes, separating two solutions of different concentrations. There is a tendency for the separated solutions to become the same concentration as the solvent passes from low concentration to high concentration. Osmosis will stop when the two solutions become equal in concentration or when pressure is applied to the solution containing higher concentration. When the higher concentrated solution is in a closed system, that is when system is of constant volume, there is a build up of pressure as the solvent passes from low to high concentration. This build up of pressure is called osmotic pressure.

Salt

A salt is any compound containing ionic bonds, that is bonds in which one or more electrons are transferred completely from one atom to another.

Interpolyelectrolyte Complexes

An interpolyelectrolyte complex is a noncovalent interaction between polyelectrolytes of opposite charge.

Charge, Polarity, and Sign

The charge, polarity, or sign of a compound refers to whether or not a compound has lost one or more electrons (positive charge, polarity, or sign) or gained one or more electrons (negative charge, polarity, or sign).

Cell Targeting Signals

Cell targeting signal (or abbreviated as the Signal) is defined in this specification as a molecule that modifies a biologically active compounds such as drug or nucleic acid and can direct it to a cell location (such as tissue) or location in a cell (such as the nucleus) either in culture or in a whole organism. By modifying the cellular or tissue location of the foreign gene, the function of the biologically active compound can be enhanced.

The cell targeting signal can be a protein, peptide, lipid, steroid, sugar, carbohydrate, (non-expressing) polynucleic acid or synthetic compound. The cell targeting signal enhances cellular binding to receptors, cytoplasmic transport to the nucleus and nuclear entry or release from endosomes or other intracellular vesicles.

Nuclear localizing signals enhance the targeting of the pharmaceutical into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS (H-SEQ ID NO: 2-OH,) or long NLS's (H-SEQ ID NO: 3-OH,; and H-SEQ ID NO: 4-OH,). Other NLS peptides have been derived from M9 protein (SEQ ID NO: 5), E1A (H-SEQ ID NO: 6-OH,), nucleoplasmin (H-SEQ ID NO: 7-OH,), and c-myc (H-SEQ ID NO: 8-OH,).

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (SEQ ID NO: 9), viral components such as influenza virus hemagglutinin subunit HA-2 peptides and other types of amphipathic peptides.

Cellular receptor signals are any signal that enhances the association of the biologically active compound with a cell. This can be accomplished by either increasing the binding of the compound to the cell surface and/or its association with an intracellular compartment, for example: ligands that enhance endocytosis by enhancing binding the cell surface. This includes agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

Interaction Modifiers

An interaction modifier changes the way that a molecule interacts with itself or other molecules, relative to molecule containing no interaction modifier. The result of this modification is that self-interactions or interactions with other molecules are either increased or decreased. For example cell targeting signals are interaction modifiers with change the interaction between a molecule and a cell or cellular component. Polyethylene glycol is an interaction modifier that decreases interactions between molecules and themselves and with other molecules.

Reporter or Marker Molecules

Reporter or marker molecules are compounds that can be easily detected. Typically they are fluorescent compounds such as fluorescein, rhodamine, Texas red, cy 5, cy 3 or dansyl compounds. They can be molecules that can be detected by infrared, ultraviolet or visible spectroscopy or by antibody interactions or by electron spin resonance. Biotin is another reporter molecule that can be detected by labeled avidin. Biotin could also be used to attach targeting groups.

Linkages

An attachment that provides a covalent bond or spacer between two other groups (chemical moieties). The linkage may be electronically neutral, or may bear a positive or negative charge. The chemical moieties can be hydrophilic or hydrophobic. Preferred spacer groups include, but are not limited to C1–C12 alkyl, C1–C12 alkenyl, C1–C12 alkynyl, C6–C18 aralkyl, C6–C18 aralkenyl, C6–C18 aralkynyl, ester, ether, ketone, alcohol, polyol, amide, amine, polyglycol, polyether, polyamine, thiol, thio ether, thioester, phosphorous containing, and heterocyclic.

Bifunctional

Bifunctional molecules, commonly referred to as crosslinkers, are used to connect two molecules together, i.e. form a linkage between two molecules. Bifunctional molecules can contain homo or heterobifunctionality.

Crosslinking

Crosslinking refers to the chemical attachment of two or more molecules with a bifunctional reagent. A bifunctional reagent is a molecule with two reactive ends. The reactive ends can be identical as in a homobifunctional molecule, or different as in a heterobifunctional molecule.

Labile Bond

A labile bond is a covalent bond that is capable of being selectively broken. That is, the labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule.

Labile Linkage

A labile linkage is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

pH-Labile Linkages and Bonds pH-labile refers to the selective breakage of a covalent bond under acidic conditions (pH<7). That is, the pH-labile bond may be broken under acidic conditions in the presence of other covalent bonds without their breakage. The term pH-labile includes both linkages and bonds that are pH-labile, very pH-labile, and extremely pH-labile.

Very pH-Labile Linkages and Bonds

A subset of pH-labile bonds is very pH-labile. For the purposes of the present invention, a bond is considered very pH-labile if the half-life for cleavage at pH 5 is less than 45 minutes.

Extremely pH-Labile Linkages and Bonds

A subset of pH-labile bonds is extremely pH-labile. For the purposes of the present invention, a bond is considered extremely pH-labile if the half-life for cleavage at pH 5 is less than 15 minutes.

Amphiphilic and Amphipathic Compounds

Amphipathic, or amphiphilic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Detergent

Detergents or surfactants are water-soluble molecules containing a hydrophobic portion (tail) and a hydrophilic portion (head), which upon addition to water decrease water's surface tension. The hydrophobic portion can be alkyl, alkenyl, alkynyl or aromatic. The hydrophilic portion can be charged with either net positive (cationic detergents), negative (anionic detergents), uncharged (nonionic detergents), or charge neutral (zwitterionic detergent). Examples of anionic detergents are sodium dodecyl sulfate, glycolic acid ethoxylate(4 units) 4-tert-butylphenylether, palmitic acid, and oleic acid. Examples of cationic detergents are cetyltrimethylammonium bromide and oleylamine. Examples of nonionic detergents include, laurylmaltoside, Triton X-100, and Tween. Examples of zwitterionic detergents include 3-[(3-cholamidopropyl)dimthylammonio]1-propane-sulfonate (CHAPS), and N-tetradecyl-N,N-dimethyl-3-ammoniu-1-propanesulfonate.

Surface Tension

The surface tension of a liquid is the force acting over the surface of the liquid per unit length of surface that is perpendicular to the force that is acting of the surface. Surface charge has the units force per length, e.g. Newtons/meter.

Membrane Active Compound

Membrane active agents or compounds are compounds (typically a polymer, peptide or protein) that are able alter the membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. An example of a membrane active agent in our examples is the peptide melittin, whose membrane activity is demonstrated by its ability to release heme from red blood cells (hemolysis). In addition, dimethylmaleamic-modified melittin(DM-Mel) reverts to melittin in the acidic environment of the endosome causes endosomal release as seen by the diffuse staining of fluorescein-labeled dextran in our endosomal release assay.

More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane. In addition, transport between liposomes, or cell membranes, may be accomplished by the fusion of the two membranes and thereby the mixing of the contents of the two membranes.

Membrane Active Peptides.

Membrane active peptides are peptides that have membrane activity. There are many naturally occurring membrane active peptides such as cecropin (insects), magainin, CPF 1, PGLa, Bombinin BLP-1 (all three from amphibians), melittin (bees), seminalplasmin (bovine), indolicidin, bactenecin (both from bovine neutrophils), tachyplesin 1 (crabs), protegrin (porcine leukocytes), and defensins (from human, rabbit, bovine, fungi, and plants). Gramicidin A and gramicidin S (bacillus brevis), the lantibiotics such as nisin (lactococcus lactis), androctonin (scorpion), cardiotoxin I (cobra), caerin (frog litoria splendida), dermaseptin (frog). Viral peptides have also been shown to have membrane activity, examples include hemagglutinin subunit HA-2 (influenza virus), E1 (Semliki forest virus), F1 (Sendai and measles viruses), gp41 (HIV), gp32 (SIV), and vp1 (Rhino, polio, and coxsackie viruses). In addition synthetic peptides have also been shown to have membrane activity. Synthetic peptides that are rich in leucines and lysines (KL or $KL_n$ motif) have been shown to have membrane activity. In particular, the peptide $H_2N$-SEQ ID NO: 10-$CO_2$, termed $KL_3$, is membrane active.

Compounds or Chemical Groups (Moieties) that Inhibit or Block the Membrane Activity of another Compound or Chemical Moiety An interaction with a membrane active agent by modification or complexation (including covalent, ionic, hydrogen bonding, coordination, and van der Waals bonds) with another compound that causes a reduction, or cessation of the said agents membrane activity. Examples include the covalent modification of a membrane-active peptide by the covalent attachment of an inhibitory chemical group (moiety) to the membrane active peptide. Another example includes the interpolyelectrolyte complexation of a membrane active polyanion and inhibitory polycation.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

The main chain of a polymer is composed of the atoms whose bonds are required for propagation of polymer length. For example in poly-L-lysine, the carbonyl carbon, α-carbon, and α-amine groups are required for the length of the polymer and are therefore main chain atoms. The side chain of a polymer is composed of the atoms whose bonds are not required for propagation of polymer length. For example in poly-L-lysine, the β, γ, δ, and ε-carbons, and ε-nitrogen are not required for the propagation of the polymer and are therefore side chain atoms.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M. P. Stevens Polymer Chemistry: An Introduction New York Oxford University Press 1990). Template polymerization can be used to form polymers from daughter polymers. Step Polymerization:

In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed. Typically, step polymerization is done either of two different ways. One way, the monomer has both reactive functional groups (A and B) in the same molecule so that

Or the other approach is to have two difunctional monomers.

Generally, these reactions can involve acylation or alkylation. Acylation is defined as the introduction of an acyl group (—COR) onto a molecule. Alkylation is defined as the introduction of an alkyl group onto a molecule.

If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate, or alkylphosphate, arylhalides (difluoro-dinitrobenzene), anhydrides or acid halides, p-nitrophenyl esters, o-nitrophenyl pentachlorophenyl esters, or pentafluorophenyl esters. In other terms when function A is an amine then function B can be acylating or alkylating agent or amination.

If functional group A is a thiol, sulfhydryl, then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid {TNB} derivatives).

If functional group A is carboxylate then function B can be (but not restricted to) a diazoacetate or an amine in which a carbodiimide is used. Other additives may be utilized such as carbonyldiimidazole, dimethylaminopyridine, N-hydroxysuccinimide or alcohol using carbodiimide and dimethylaminopyridine.

If functional group A is a hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used.

If functional group A is an aldehyde or ketone then function B can be (but not restricted to) an hydrazine, hydrazide derivative, amine (to form a imine or iminium that may or may not be reduced by reducing agents such as $NaCNBH_3$) or hydroxyl compound to form a ketal or acetal.

Yet another approach is to have one difunctional monomer so that

A—A plus another agent yields-[A—A]-.

If function A is a thiol, sulfhydryl, group then it can be converted to disulfide bonds by oxidizing agents such as iodine ($I_2$) or $NaIO_4$ (sodium periodate), or oxygen ($O_2$). Function A can also be an amine that is converted to a thiol, sulfhydryl, group by reaction with 2-Iminothiolate (Traut's reagent) which then undergoes oxidation and disulfide formation. Disulfide derivatives (such as a pyridyl disulfide or 5-thio-2-nitrobenzoic acid {TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, thiol, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thio-ether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methacrylamide groups can undergo chain reaction, which can be radical, anionic, or cationic. Chain polymerization can also be accomplished by cycle or ring opening polymerization. Several different types of free radical initiatiors could be used that include peroxides, hydroxy peroxides, and azo compounds such as 2,2'-Azobis(-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrazine, heterocycles (like imidazole, pyridine, morpholine, pyrimidine, or pyrene. The amines could be pH-sensitive in that the $pK_a$ of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide.

Monomers can also be hydrophobic, hydrophilic or amphipathic. Monomers can also be intercalating agents such as acridine, thiazole organge, or ethidium bromide.

Other Components of the Monomers and Polymers: The polymers have other groups that increase their utility. These groups can be incorporated into monomers prior to polymer formation or attached to the polymer after its formation. These groups include: Targeting Groups—such groups are used for targeting the polymer-nucleic acid complexes to specific cells or tissues. Examples of such targeting agents include agents that target to the asialoglycoprotein receptor by using asioglycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Polyelectrolyte

A polyelectrolyte, or polyion, is a polymer possessing charge, i.e. the polymer contains a group (or groups) that has either gained or lost one or more electrons. A polycation is a polyelectrolyte possessing net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polyelectrolyte containing a net negative charge. The polyanion can contain monomer units that are charge negative, charge neutral, or charge positive, however, the net charge on the polymer must be negative. A polyanion can also mean a non-polymeric molecule that contains two or more negative charges. The term polyelectrolyte includes polycation, polyanion, zwitterionic polymers, and neutral polymers. The term zwitterionic refers to the product (salt) of the reaction between an acidic group and a basic group that are part of the same molecule.

Chelator

A chelator is a polydentate ligand, a molecule that can occupy more than one site in the coordination sphere of an ion, particularly a metal ion, primary amine, or single proton. Examples of chelators include crown ethers, cryptates, and non-cyclic polydentate molecules. A crown ether is a cyclic polyether containing (—X—(CR1–2)n)m units, where n=1–3 and m=3–8. The X and CR1–2 moieties can be substituted, or at a different oxidation states. X can be oxygen, nitrogen, or sulfur, carbon, phosphorous or any combination thereof. R can be H, C, O, S, N, P. A subset of crown ethers described as a cryptate contain a second (—X—(CR1–2)n)z strand where z=3–8. The beginning X atom of the strand is an X atom in the (—X—(CR1–2)n)m unit, and the terminal CH2 of the new strand is bonded to a second X atom in the (—X—(CR1–2)n)m unit. Non-cyclic polydentate molecules containing (—X—(CR1–2)n)m unit(s), where n=1–4 and m=1–8. The X and CR1–2 moieties can be substituted, or at a different oxidation states. X can be oxygen, nitrogen, or sulfur, carbon, phosphorous or any combination thereof.

Polychelator

A polychelator is a polymer associated with a plurality of chelators by an ionic or covalent bond and can include a spacer. The polymer can be cationic, anionic, zwitterionic, neutral, or contain any combination of cationic, anionic, zwitterionic, or neutral groups with a net charge being cationic, anionic or neutral, and may contain steric stabilizers, peptides, proteins, signals, or amphipathic compound for the formation of micellar, reverse micellar, or unilamellar structures. Preferably the amphipathic compound can have a hydrophilic segment that is cationic, anionic, or zwitterionic, and can contain polymerizable groups, and a hydrophobic segment that can contain a polymerizable group.

Steric Stabilizer

A steric stabilizer is a long chain hydrophilic group that prevents aggregation of final polymer by sterically hindering particle to particle electrostatic interactions. Examples include: alkyl groups, PEG chains, polysaccharides, hydrogen molecules, alkyl amines. Electrostatic interactions are the non-covalent association of two or more substances due to attractive forces between positive and negative charges.

Buffers

Buffers are made from a weak acid or weak base and their salts. Buffer solutions resist changes in pH when additional acid or base is added to the solution.

Biological, Chemical, or Biochemical Reactions

Biological, chemical, or biochemical reactions involve the formation or cleavage of ionic and/or covalent bonds.

Reactive

A compound is reactive if it is capable of forming either an ionic or a covalent bond with another compound. The portions of reactive compounds that are capable of forming covalent bonds are referred to as reactive functional groups.

Lipids

Lipids are compounds that are insoluble in water but soluble in organic solvent which have the general structure composed of two distinct hydrophobic sections, that is two separate sections of uninterrupted carbon-carbon bonds. The two hydrophobic sections are connected through a linkage that contains at least one heteroatom, that is an atom that is not carbon (e.g. nitrogen, oxygen, silicon, and sulfur). Examples include esters and amides of fatty acids and include the glycerides (1,2-dioleoylglycerol (DOG)), glycolipids, phospholipids (dioleoylphosphatidylethanolamine (DOPE)).

Hydrocarbon

Hydrocarbon means containing carbon and hydrogen atoms; and halohydrocarbon means containing carbon, halogen (F, Cl, Br, I), and hydrogen atoms.

Alkyl, Alkene, Alkyne, Aryl

Alkyl means any $sp^3$-hybridized carbon-containing group; alkenyl means containing two or more $sp^2$ hybridized carbon atoms; aklkynyl means containing two or more sp hybridized carbon atoms; aralkyl means containing one or more aromatic ring(s) in addition containing $sp^3$ hybridized carbon atoms; aralkenyl means containing one or more aromatic ring(s) in addition to containing two or more $sp^2$ hybridized carbon atoms; aralkynyl means containing one or more aromatic ring(s) in addition to containing two or more sp hybridized carbon atoms; steroid includes natural and unnatural steroids and steroid derivatives.

Steroid

A steroid derivative means a sterol, a sterol in which the hydroxyl moiety has been modified (for example, acylated), or a steroid hormone, or an analog thereof. The modification can include spacer groups, linkers, or reactive groups.

Carbohydrate

Carbohydrates include natural and unnatural sugars (for example glucose), and sugar derivatives (a sugar derivative means a system in which one or more of the hydroxyl groups on the sugar moiety has been modified (for example, but not limited to, acylated), or a system in which one or more of the hydroxyl groups is not present).

Polyoxyethylene

Polyoxyethylene means a polymer having ethylene oxide units (—$(CH_2CH_2O)_n$—, where n=2–3000).

Compound

A compound is a material made up of two or more elements.

Electron Withdrawing and Donating Groups

Electron withdrawing group is any chemical group or atom composed of electronegative atom(s), that is atoms that tend to attract electrons. Electron donating group is any chemical group or atom composed of electropositive atom(s), that is atoms that tend to attract electrons.

Resonance Stabilization

Resonance stabilization is the ability to distribute charge on multiple atoms through pi bonds. The inductive effective, in a molecule, is a shift of electron density due to the polarization of a bond by a nearby electronegative or electropositive atom.

Sterics

Steric hindrance, or sterics, is the prevention or retardation of a chemical reaction because of neighboring groups on the same molecule.

Activated Carboxylate

An activated carboxylate is a carboxylic acid derivative that reacts with nucleophiles to form a new covalent bond. Nucleophiles include nitrogen, oxygen and sulfur-containing compounds to produce ureas, amides, carbonates, carbamates, esters, and thioesters. The carboxylic acid may be activated by various agents including carbodiimides, carbonates, phosphoniums, and uroniums to produce activated carboxylates acyl ureas, acylphosphonates, acid anhydrides, and carbonates. Activation of carboxylic acid may be used in conjunction with hydroxy and amine-containing compounds to produce activated carboxylates N-hydroxysuccinimide esters, hydroxybenzotriazole esters, N-hydroxy-5-norbornene-endo-2,3-dicarboximide esters, p-nitrophenyl esters, pentafluorophenyl esters, 4-dimethylaminopyridinium amides, and acyl imidazoles.

Nucleophile

A nucleophile is a species possessing one or more electron-rich sites, such as an unshared pair of electrons, the negative end of a polar bond, or pi electrons.

Cleavage and Bond Breakage

Cleavage, or bond breakage is the loss of a covalent bond between two atoms. Cleavable means that a bond is capable of being cleaved.

Substituted Group or Substitution

A substituted group or a substitution refers to chemical group that is placed onto a parent system instead of a hydrogen atom. For the compound methylbenzene (toluene), the methyl group is a substituted group, or substitution on the parent system benzene. The methyl groups on 2,3- dimethylmaleic anhydride are substituted groups, or substitutions on the parent compound (or system) maleic anhydride.

Primary and Secondary Amine

A primary amine is a nitrogen-containing compound that is derived by monosubstitution of ammonia ($NH_3$) by a carbon-containing group. A primary amine is a nitrogen-containing compound that is derived by disubstitution of ammonia ($NH_3$) by a carbon-containing group.

Preferred Embodiments

The following description provides exemplary embodiments of the systems, compositions, and methods of the present invention. These embodiments include a variety of systems that have been demonstrated as effective delivery systems both in vitro and in vivo. The invention is not limited to these particular embodiments. The following topics are discussed in turn: I) Labile, pH-labile, Very pH-labile Bonds, and Extremely pH-Labile Bonds II) Polymers with pH-Labile Bonds, III) Polymers Containing Several Membrane Active Compounds, IV) Membrane Active Compounds Containing Labile Bonds, V) Mixtures of Membrane Active Compounds and Labile Compounds, VI) Biologically active compounds Containing Very pH-Labile Bonds, and VII) pH-Labile Amphipathic Compounds I. Labile, pH-Labile Bonds, Very pH-Labile, and Extremely pH-Labile Bonds A) Labile Bonds In one embodiment, disulfide bonds are used in a variety of molecules, and polymers that include peptides, lipids, liposomes.

B) pH-Labile

In one embodiment, ketals that are labile in acidic environments (pH less than 7, greater than 4) to form a diol and a ketone are used in a variety of molecules and polymers that include peptides, lipids, and liposomes.

In one embodiment, acetals that are labile in acidic environments (pH less than 7, greater than 4) to form a diol and an aldehyde are used in a variety of molecules and polymers that include peptides, lipids, and liposomes.

In one embodiment, imines or iminiums that are labile in acidic environments (pH less than 7, greater than 4) to form an amine and an aldehyde or a ketone are used in a variety of molecules and polymers that include peptides, lipids, and liposomes.

The present invention additionally provides for the use of polymers containing silicon-oxygen-carbon linkages (either in the main chain of the polymer or in a side chain of the polymer) that are labile under acidic conditions. Organosilanes have long been utilized as oxygen protecting groups in organic synthesis due to both the ease in preparation (of the silicon-oxygen-carbon linkage) and the facile removal of the protecting group under acidic conditions. For example, silyl ethers and silylenolethers, both posses such a linkage. Silicon-oxygen-carbon linkages are susceptible to hydrolysis under acidic conditions forming silanols and an alcohol (or enol). The substitution on both the silicon atom and the alcohol carbon can affect the rate of hydrolysis due to steric and electronic effects. This allows for the possibility of tuning the rate of hydrolysis of the silicon-oxygen-carbon linkage by changing the substitution on either the organosilane, the alcohol, or both the organosilane and alcohol to facilitate the desired affect. In addition, charged or reactive groups, such as amines or carboxylate, may be linked to the silicon atom, which confers the labile compound with charge and/or reactivity.

The present invention additionally provides for the use of polymers containing silicon-nitrogen (silazanes) linkages (either in the main chain of the polymer or in a side chain of the polymer) that are susceptible to hydrolysis. Hydrolysis of a silazane leads to the formation of a silanol and an amine. Silazanes are inherently more susceptible to hydrolysis than is the silicon-oxygen-carbon linkage, however, the rate of hydrolysis is increased under acidic conditions. The substitution on both the silicon atom and the amine can affect the rate of hydrolysis due to steric and electronic effects. This allows for the possibility of tuning the rate of hydrolysis of the silazane by changing the substitution on either the silicon or the amine to facilitate the desired affect.

The present invention additionally provides for the use of polymers containing silicon-carbon linkages (either in the main chain of the polymer or in a side chain of the polymer) that are susceptible to hydrolysis. For example, arylsilanes, vinylsilanes, and allylsilanes all posses a carbon-silicon bond that is susceptible to hydrolysis.

C) Very pH-Labile Bonds

To construct labile molecules, one may construct the molecule with bonds that are inherently labile such as disulfide bonds, diols, diazo bonds, ester bonds, sulfone bonds, acetals, ketals, enol ethers, enol esters, imines, imminiums, and enamines. In addition, one may construct a polymer in such a way as to put reactive groups, i.e. electrophiles and nucleophiles, in close proximity so that reaction between the function groups is more rapid than if the reactive groups are not in close proximity. Examples include having carboxylic acid derivatives (acids, esters, amides) and alcohols, thiols, carboxylic acids or amines in the same molecule reacting together to make esters, thiol esters, acid anhydrides or amides.

An example of the construction of labile molecules containing labile bonds is the use of the acid labile enol ether bond. The enol ether is an ether, a molecule containing a —C—O—C— linkage, in which one of the carbons bonded to oxygen is sp2 hybridized and bonded to another carbon, i.e. an enol. Enols are unstable and rapidly convert to the carbonyl, i.e. the ketone or aldehyde. Enol ethers are stable, relative to enols, but under acidic aqueous conditions convert to alcohol and ketone or aldehyde. Depending on the structures of the carbonyl compound formed and the alcohol release, enol hydrolysis can be very pH-labile. In general, hydrolysis to form ketones is much faster than the rate of conversion to aldehydes. For example the rate of hydrolysis of ethyl isopropenyl ether to form ethanol and acetone is ca. 3600 times faster than the hydrolysis of ethyl trans-propenyl ether to form ethanol and propanal.

Cleavage of an Enol Ether.

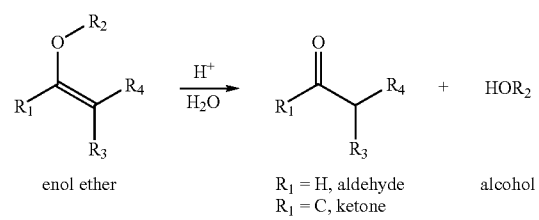

enol ether     $R_1$ = H, aldehyde     alcohol
             $R_1$ = C, ketone

There are two relatively facile methods for the synthesis of ketone-generation enol ether, although the generation of enol ethers is not limited to these methods and one skilled in the art may find more. One method, metal-liquid ammonia reduction of aromatic compounds, such as phenol ethers, results in the reduction of one carbon-carbon double bond to produce a diene (Birch A. J. *J. Chem. Soc.* 1946, 593). Another method is the elimination of β-halogen ethers (where chloride, fluoride, bromide, and iodide are halogens) under basic conditions.

Two synthetic strategies for the generation of enol ethers

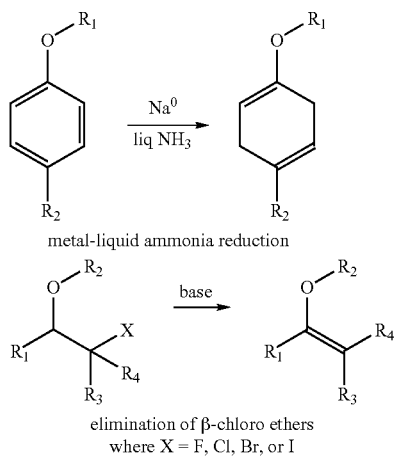

elimination of β-chloro ethers
where X = F, Cl, Br, or I

An advantage of these methods is that the labile enol ether is produced from relatively stable ethers. This stability of starting material enables one to construct the labile molecule under conditions where it is not labile and then produce the labile enol ether linkage. Using suitable β-haloethers, both methods produce enol ethers that hydrolyze into ketones, which enable one to construct very pH-labile bonds. For example analogs of ethyl isopropenyl ether, which may be synthesized from β-haloethers, have half-lives of roughly 2 minutes at pH 5 (Kresge, A. J.; Sagatys, D. S.; Chen, H. L. *J. Am. Chem. Soc.* 1977, 99, 7228). A facile method for the production of a polymer containing isoproprenyl ether is the elimination of polyepichlorohydrin under basic conditions (Nishikubo, T., Iiazawa, T., Sugarwara, Y., and Shimokawa, T. *J. Polym. Sci., Polym Chem. Ed.* 1986, 24, 1097.) It has been shown (Perez, M., Ronda, J. C., Reina, J. A., Serra, A. *Polymer* 1998, 39, 3885.) that reaction of epichlorohydrin with phenolate salts is a competition between substitution, to form the phenol ether, and elimination to form the enol ether. To, illustrate the use of elimination of β-haloethers to construct enol ether-containing polyions, we reacted poly-epichlorohydrin with the tetrabutylammonium disalt of para-hydroxyphenylacetic acid. The product was a polyanion, due to the substitution reaction, which had enol ether functional groups. This polyanion's ability to from complexes with polyallylamine was lost upon acidification. In addition this enol either is very pH-labile: measurement of the rate of hydrolysis of the enol ether group by UV spectroscopy revealed a hydrolysis with a half-life of 37 minutes at pH 5.

Analogs of ethyl cyclohexenyl ether, which may be synthesized from phenol ethers, have half-lives of roughly 14 minutes at pH 5 (Kresge, A. J.; Sagatys, D. S.; Chen, H. L. *J. Am. Chem. Soc.* 1977, 99, 7228). To illustrate this approach to construct enol ethers, we synthesized glycolic acid ethoxylate(4 units) 4-tert-buty-1,4-cyclohexadiene ether by metal-liquid ammonia reduction of glycolic acid ethoxylate(4 units) 4-tert-buty-phenyl ether, which is a phenol ether. The hydrolysis of this enol ether is very acid labile. The half-life of the hydrolysis of this enol ether -containing surfactant was 40 minutes at pH 5.

D. Extremely pH-Labile Bonds

An illustrative embodiment of the present invention, in which proximity of reactive groups confers lability, is shown by the conversion of amine to amides with anhydrides. Reaction of an amine with an anhydride results in the formation of an amide and a carboxylic acid. As is the case with all chemical reactions, this coupling of amine and anhydride is, in theory, reversible. However, as is the case for many chemical reactions, the reverse reaction (between a carboxylic acid and amide to form an anhydride and amine) is so unfavorable that the reaction between an amine and an anhydride is considered irreversible. Exceptions to this irreversibility are observed when the anhydride is a cyclic anhydride such that the formed amide and acid are in the same molecule, an amide acid. Placement of both reactive groups (amide and carboxylic acid) in the same molecule accelerates their reaction such that amine-anhydride reactivity becomes functionally reversible. For example, the product of succinic anhydride and a primary amine, a succinamic acid, reverse back to amine and anhydride 10,000 times faster than the products between non-cyclic anhydride and a primary amine. In particular, the product of primary amines with maleic anhydride and maleic anhydride derivatives, maleamic acids, revert back to amine and anhydride with amazing speed, $1 \times 10^9$ to $1 \times 10^{13}$ times faster than its noncyclic analogues (Kirby, A J. *J. Adv. Phys. Org Chem.* 1980, 17, 183)

Reaction of an Amine and an Anhydride to Form an Amide Acid.

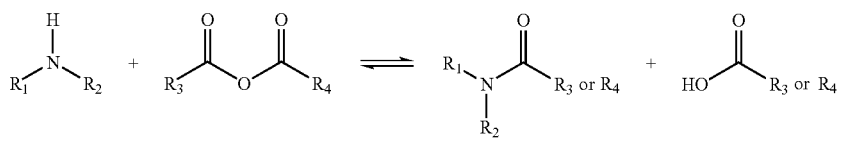

The amide acid that converts to amine and anhydride is the protonated acid, not the deprotonated carboxylate. For this reason, cleavage of the amide acid to form amine and anhydride is pH-dependent. This pH-dependent reactivity can be exploited to form reversible pH-sensitive linkers. Linkers, or spacer molecules, are used to conjugate passenger molecules and carrier molecules, which increase the transport and delivery of passenger molecules. Specifically, cis-aconitic acid is used as such a pH-sensitive linker molecule. The γ-carboxylate is first coupled to a carrier molecule, a molecule that assists in delivery such as an interaction modifier or a targeting ligand. In a second step, either the α or β carboxylate is coupled to a passenger molecule, such as a biologically active compound, to form a pH-sensitive coupling of passenger and carrier molecules.

An estimation of the kinetics of cleavage between passenger and carrier reveals that at pH 5 the half-life of cleavage is between 8 and 24 hours (Blattler, W. A.; Kuenzi, B. S.; Lambert, J. M.; Senter, P. D. *Biochemistry*, 1985, 24, 1517–1524).

Structures of Cis-Aconitic Anhydride and Maleic Anhydride.

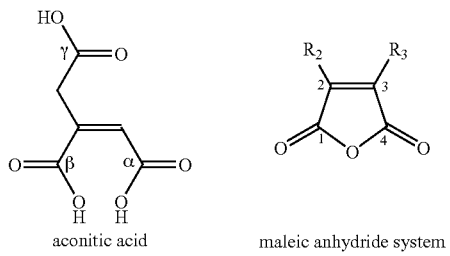

aconitic acid    maleic anhydride system

The pH at which cleavage occurs is controlled by the addition of chemical constituents to the labile moiety. The rate of conversion of maleamic acids to amines and maleic anhydrides is strongly dependent on substitution ($R_2$ and $R_3$) of the maleic anhydride system. When $R_2$ is methyl (from citraconic anhydride and similar in substitution to cis-aconitic anhydride) the rate of conversion is 50-fold higher than when $R_2$ and $R_3$ are hydrogen (derived from maleic anhydride). When there are alkyl substitutions at both $R_2$ and $R_3$ (e.g., 2,3-dimethylmaleicanhydride) the rate increase is dramatic, 10000-fold faster than maleic anhydride. Indeed, modification of the polycation poly-L-lysine with 2,3-dimethylmaleic anhydride to form the polyanionic 2,3-dimethylmaleamic poly-L-lysine, followed by incubation at acidic pH resulted in loss of 2,3-dimethylmaleic and return of the polycation poly-L-lysine. The half-life of this conversion was between 4 and 10 minutes at pH 5. This shows that conversion of 2,3-dimethylmaleamic acids (derived from the reaction between 2,3-dimethylmaleic anhydride and amines at basic pH), to amines and 2,3-dimethylmaleic anhydride at acidic pH is extremely labile. It is postulated that this increase in rate for 2,3-dimethylmaleamic acids is due to the steric interactions between the two methyl groups which increases the interaction between amide and carboxylate and thereby increases the rate of conversion to amine and anhydride. Therefore, it is anticipated that if $R_2$ and $R_3$ are groups larger than hydrogen, which includes any conceivable group, the rate of amide-acid conversion to amine and anhydride will be faster than if $R_2$ and/or $R_3$ are hydrogen. One would expect that 2,3-diethylmaleamic acids to cleave faster than ethylmaleamic acids and so forth. In addition, we synthesized 2-propionic-3-methylmaleic anhydride and found that the rate of 2-propionic-3-methylmaleamic acid cleavage was the same as that for 2,3-dimethylmaleamic acids.

Another method for the production of rapidly cleaved pH-sensitive derivatives of maleic anhydride is to react the anhydride with an alcohol or thiol to form an acid ester or acid thioester.

II. Polymers with pH-Labile Bonds

Polymers with labile bonds may have the following generalized structures: A-B-A where A is a monomer and B is a pH-labile linkage, A-B-C where A is a monomer and B is a pH-labile linkage and C is an interaction modifier. The modifying group may confer the polymer with a varieties of new characteristics such as a change in charge (e.g. cationic, anionic), cell targeting capabilities (e.g. nuclear localization signals), hydrophilicity (e.g. polyethyleneglycol, saccharides, and polysaccharides), and hydrophobicity (e.g. lipids and detergents). The labile group may be added to the polymer during polymer synthesis or the labile group may be added to the polymer after polymerization has occurred.

The present invention provides a wide variety of polymers with labile groups that find use in the delivery systems of the present invention. The labile groups are selected such that they undergo a chemical transformation (e.g., cleavage) in physiological conditions, that is, when introduced into a specific, inherent intra or extracellular environment (e.g., the lower pH conditions of an endosome, or the extracellular environment of a cancerous tumor). In addition, the chemical transformation may also be initiated by the addition of a compound. The conditions under which a labile group will undergo transformation can be controlled by altering the chemical constituents of the molecule containing the labile group. For example, addition of particular chemical moieties (e.g., electron acceptors or donors) near the labile group can effect the particular conditions (e.g., pH) under which chemical transformation will occur. The present invention provides assays for the selection of the desired properties of the labile group for any desired application. A labile group is selected based upon its half-life and is included in a polymer. The polymer is then complexed with the biologically active compounds and an in vitro or in vivo assay is used to determine whether the compound's activity is affected.

A. pH-Labile Linkages within pH-Labile Polymers

The pH-labile bond may either be in the main-chain or in the side chain. If the pH-labile bond occurs in the main chain, then cleavage of the labile bond results in a decrease in polymer length. If the pH-labile bond occurs in the side chain, then cleavage of the labile bond results in loss of side chain atoms from the polymer.

An example of a pH-labile bond in the side chain of a polymer is 2,3-dimethylmaleamic poly-L-lysine, which is formed by the reaction of poly-L-lysine with 2,3-dimethylmaleic anhydride under basic conditions. The modification of the poly-L-lysine is in the side chain and conversion of the 2,3-dimethylmaleamic poly-L-lysine to poly-L-lysine and 2,3-dimethylmaleic anhydride under acid conditions does not result in a cleavage of the polymer main, but in a cleavage of the side chain.

An example of a silicon-oxygen-carbon pH-labile bond in the side chain of the polymer is the polymer formed from the reaction of poly-L-serine and 3-aminopropyltrimethoxysilane in DMF. The ratio of 3-aminopropyl-trimethoxysilane per serine monomer units may be changed resulting in differing amounts of silylether formation. Hydrolysis of the polymer under acidic conditions regenerates the poly-L-serine and a silanol.

An example of a pH-labile bond in the main chain of the polymer is di-(2-methyl-4-hydroxymethyl(succinic semialdehyde ester)-1,3-dioxolane)-1,4-benzene:1,4-bis(3-aminopropyl)piperazine copolymer (1:1) (MC208) prepared from the reaction of di-(2-methyl-4-hydroxymethyl(succinic semialdehyde ester)-1,3-dioxolane)-1,4-benzene and: 1,4-bis(3-aminopropyl)piperazine. The resulting polymer (containing imines) can be reduced in the presence of $NaCNBH_3$ to afford the secondary amine containing copolymer (MC301) which retains the pH-lability of the parent polymer, through ketal functional groups. Both polymers contain a substituted 1,3-dioxolane ring system, ketal, which upon exposure to acidic environments hydrolyzes to a ketone and diol.

B. Polymerization Processes to Form the pH-Labile Polymers

There are a number of polymerization processes that can be utilized with the present invention. For example, the polymerization can be chain or step. This classification description is more often used that the previous terminology of addition and condensation polymer. "Most step-reaction polymerizations are condensation processes and most chain-reaction polymerizations are addition processes" (M. P. Stevens Polymer Chemistry: An Introduction New York Oxford University Press 1990). Template polymerization can be used to form polymers from daughter polymers.

1. Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields -[A-B]-Or the other approach is to have two bifunctional monomers. A—A+B—B yields -[A—A-B—B]-Generally, these reactions can involve acylation or alkylation. Acylation is defined as the introduction of an acyl group (—COR) onto a molecule. Alkylation is defined as the introduction of an alkyl group onto a molecule.

If functional group A is an amine then B can include, but is not limited to, an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate activated with a carbodiimide, alkylphosphate, arylhalides (difluoro-dinitrobenzene), anhydride, or acid halide, p-nitrophenyl ester, o-nitrophenyl ester, pentachlorophenyl ester, pentafluorophenyl ester, carbonyl imidazole, carbonyl pyridinium, or carbonyl dimethylaminopyridinium. In other terms when function A is an amine then function B can be acylating or alkylating agent or amination agent.

If functional group A is a thiol, sulfhydryl, then function B can include, but is not limited to, an iodoacetyl derivative, maleimide, aziridine derivative, acryloyl derivative, fluorobenzene derivatives, or disulfide derivative (such as a pyridyl disulfide or 5-thio-2-nitrobenzoic acid {TNB} derivatives).

If functional group A is carboxylate then function B can include, but is not limited to, a diazoacetate or an amine in which a carbodiimide is used. Other additives may be utilized such as carbonyldiimidazole, dimethylamino pyridine (DMAP), N-hydroxysuccinimide or alcohol using carbodiimide and DMAP.

If functional group A is an hydroxyl then function B can include, but is not limited to, an epoxide, oxirane, or an amine in which carbonyldiimidazole or N,N'-disuccinimidyl carbonate, or N-hydroxysuccinimidyl chloroformate or other chloroformates are used.

If functional group A is an aldehyde or ketone then function B can include, but is not limited to, an hydrazine, hydrazide derivative, amine (to form a imine or iminium that may or may not be reduced by reducing agents such as $NaCNBH_3$) or hydroxyl compound to form a ketal or acetal.

Yet another approach is to have one bifunctional monomer so that A—A plus another agent yields-[A—A]-. If function A is a thiol, sulfhydryl, group then it can be converted to disulfide bonds by oxidizing agents such as iodine ($I_2$) or $NaIO_4$ (sodium periodate), or oxygen ($O_2$).

Function A can also be an amine that is converted to a thiol, sulfhydryl, group by reaction with 2-Iminothiolate (Traut's reagent) which then undergoes oxidation and disulfide formation. Disulfide derivatives (such as a pyridyl disulfide or 5-thio-2-nitrobenzoic acid {TNB} derivatives) can also be used to catalyze disulfide bond formation.

Functional group A or B in any of the above examples could also be a photoreactive group such as aryl azide (including halogenated aryl azide), diazo, benzophenone, alkyne or diazirine derivative.

Reactions of the amine, hydroxyl, thiol, sulfhydryl, carboxylate groups yield chemical bonds that are described as amide, amidine, disulfide, ethers, esters, enamine, imine, urea, isothiourea, isourea, sulfonamide, carbamate, alkylamine bond (secondary amine), carbon-nitrogen single bonds in which the carbon contains a hydroxyl group, thioether, diol, hydrazone, diazo, or sulfone.

2. Chain Polymerization: In chain-reaction polymerization, growth of the polymer occurs by successive addition of monomer units to limited number of growing chains. The initiation and propagation mechanisms are different and there is usually a chain-terminating step. The polymerization rate remains constant until the monomer is depleted.

Monomers containing (but not limited to) vinyl, acrylate, methacrylate, acrylamide, methacrylamide groups can undergo chain reaction which can be radical, anionic, or cationic. Chain polymerization can also be accomplished by cycle or ring opening polymerization. A number of different types of free radical initiators could be used that include peroxides, hydroxy peroxides, and azo compounds such as 2,2'-Azobis(-amidinopropane)dihydrochloride (AAP).

C. Types of Monomers for Incorporation into pH-Labile Polymers and Types of pH-Labile Polymers A wide variety of monomers can be used in the polymerization processes. These include positive charged organic monomers such as amines, amine salts, imidine, guanidine, imine, hydroxylamine, hydrazine, heterocycles like imidazole, pyridine, morpholine, pyrimidine, or pyrene. Polymers from such monomers includes, but are not limited to such examples as poly-L-lysine, polyethylenimine (linear and branched), and polyallylamine. The amines could be pH-sensitive in that the pKa of the amine is within the physiologic range of 4 to 8. Specific pH-sensitive amines include spermine, spermidine, N,N'-bis(2-aminoethyl)-1,3-propanediamine (AEPD), and 3,3'-Diamino-N,N-dimethyl-dipropylammonium bromide.

In addition negatively charged monomers such as sulfates, sulfonates, carboxylates, and phosphates may be used to generated polyanionic polymers. Examples of these polyanions include, but are not limited to, nucleic acids, polysulfonylstyrene, and heparin sulfate. Also, amine-containing polycations may be converted to polyanions by reaction with cyclic anhydrides such as succinic anhydride and glutaric anhydride to form glutarylated and succinylated polymers which are polyanionic. Examples of these polyanions include, but are not limited to, succinylated and glutarylated poly-L-lysine, and succinylated and glutarylated polyallylamine.

Monomers can also be hydrophobic, hydrophilic or amphipathic.

Monomers can also be intercalating agents such as acridine, thiazole organge, or ethidium bromide. Monomers can also contain chemical moieties that can be modified before or after the polymerization including (but not limited to) amines (primary, secondary, and tertiary), amides, carboxylic acid, ester, hydroxyl, hydrazine, alkyl halide, aldehyde, and ketone.

The pH-labile polymer can be a polyion, polycation, polyanion, zwitterionic polymers, and neutral polymers. It can also contain a chelator and be a polychelator.

D. Other Components of the Monomers and Polymers

The polymers may include other groups that increase their utility. These groups can be incorporated into monomers prior to polymer formation or attached to the polymer after its formation. These groups include, but are not limited to: targeting groups and signals (e.g, cell receptor, nuclear targeting signals), membrane active compounds, reporter or marker molecules, spacers, steric stabilizers, chelators, polycations, polyanions, and polymers.

III. Polymers Containing Several Membrane Active Compounds

The present invention specifies polymers containing more than two membrane active compounds. In one embodiment, the membrane active compounds are grafted onto a preformed polymer to form a comb-type polymer. For example, both the membrane active peptides melittin and $KL_3$ contain only one carboxylate, which is at the carboxy terminus. Therefore, activation of the peptides with carboxy-activating agents such as carbodiimides will react with only one group. If this activation is done in the presence of an excess of an amine, then one may obtain selective amide formation. In particular, if the activation is done in the presence of a polyamine, one would obtain selective coupling of the peptide to the polyamine. This method of coupling of a membrane active peptide to a polyamine was accomplished for the coupling of peptides $KL_3$ and melittin to polyamines polyallylamine and poly-L-lysine. In each case, the membrane activity, as judged by hemolysis, was retained and, in case of $KL_3$, was improved after attachment to the polycation.

In another embodiment, the membrane active compounds are incorporated into the polymer by chain or step polymerization processes. For example, an acryloyl group at the N-terminus of a peptide allows one to form a polyacrylamide polymer with peptide side chains (O'Brien-Simpson, N. M., Ede, N. J., Brown, L. E., Swan, J., Jackson, D. C *J. Am. Chem. Soc.* 1997, 119, 1183). N-acryloyl KL3 was synthesized and polymerized and found to retain the activity of monomeric KL3, but was able to form particles with DNA.

IV. Membrane Active Compounds Containing Labile Bonds

The invention specifies compounds that are of the general structure: A-B-C wherein A is a membrane active compound, B is a labile linkage, and C is a compound that inhibits the membrane activity of compound A. A membrane active compound is defined within the Definitions Section and includes membrane active peptides.

The term labile linkage is defined above and includes pH-labile bonds such as, acetals, ketals, enol ethers, enol esters, enamines, and imines. It also includes extremely pH-labile bonds such as 2,3-disubstituted maleamic acids and very pH-labile bonds such as enol ethers.

Preferred embodiments include 2,3-dimethylmaleamic-mellitin, 2-propionic-3-methylmaleamic melittin, 2-propionic-3-methylmaleamic KL3, and 2,3-dimethylmaleamic-melittin, which are membrane inactive compounds that become membrane active under acidic conditions.

The disulfide linkage (RSSR') may be used within bifunctional molecules. The reversibility of disulfide bond formation makes them useful tools for the transient attachment of two molecules. Disulfides have been used to attach a bioactive compound and another compound (Thorpe, P. E. *J. Natl. Cancer Inst.* 1987, 79, 1101). The disulfide bond is reduced thereby releasing the bioactive compound. Disulfide bonds may also be used in the formation of polymers (Kishore, K., Ganesh, K. in Advances in Polymer Science, Vol. 21, Saegusa, T. Ed., 1993).

In another embodiment, the invention includes compositions containing biologically active compounds and compounds of the general structure: A-B-C wherein A is a membrane active compound, B is a labile linkage, and C is a compound that inhibits the membrane activity of compound A. The biologically active compounds include pharmaceutical drugs, nucleic acids and genes. In yet another embodiment, these compounds that are of the general structure—A-B-C wherein A is a membrane active compound, B is a labile linkage, and C is a compound that inhibits the membrane activity of compound A- are used to deliver biologically active compounds that include pharmaceutical drugs, nucleic acids and genes. In one specific embodiment, these A-B-C compounds are used to deliver nucleic acids and genes to muscle (skeletal, heart, respiratory, striated, and non-striated), liver (hepatocytes), spleen, immune cells, gastrointestinal cells, cells of the nervous system (neurons, glial, and microglial), skin cells (dermis and epidermis), joint and synovial cells, tumor cells, kidney, cells of the immune system (dendiritic, T cells, B cells, antigen-presenting cells, macrophages), exocrine cells (pancreas, salivary glands), prostate, adrenal gland, thyroid gland, eye structures (retinal cells), and respiratory cells (cells of the lung, nose, respiratory tract). Upon cleavage of B, membrane activity is restored to compound A. This cleavage occurs in certain tissue, organ, and sub-cellular locations that are controlled by the microenvironment of the location and also by the addition of exogenous agents. Delivery can be accomplished by direct intraparenchymal injections (into the parenchyma of a tissue) or by intravascular conditions. Intravascular conditions also include conditions under which the permeability of the vessel is increased and when the injection is leads to increased intravascular pressure.

V. Mixtures of Membrane Active Compounds and Labile Compounds

In addition, the invention is a composition of matter that includes a membrane active compound and a labile compound. In one embodiment, the labile compound inhibits the membrane activity of the membrane active compound. Upon chemical modification of the labile compound, membrane activity is restored to the membrane active compound. This chemical modification occurs in certain tissue, organ, and sub-cellular locations that are controlled by the microenvironment of the location and also by the addition of exogenous agents. In one embodiment the chemical modification involves the cleavage of the polymer. In one embodiment, the membrane active compound and the inhibitory labile compound are polyions and are of opposite charge. For example, the membrane active compound is a polycation and the inhibitory labile compound is a polyanion, or the membrane active compound is a polyanion and the inhibitory labile compound is a polycation.

In another embodiment, the invention includes compositions containing biologically active compounds, a membrane active compound and a labile compound. Upon chemical modification of the labile compound, membrane activity is restored to the membrane active compound. This chemical modification occurs in certain tissue, organ, and sub-cellular locations that are controlled by the microenvironment of the location and also by the addition of exogenous agents. In one embodiment the chemical modification involves the cleavage of the polymer. In one specific embodiment, these compositions containing biologically active compounds, a membrane active compound and a labile compound are used to deliver nucleic acids and genes to muscle (skeletal, heart, respiratory, striated, and non-striated), liver (hepatocytes), spleen, immune cells, gastrointestinal cells, cells of the nervous system (neurons, glial, and microglial), skin cells (dermis and epidermis), joint and synovial cells, tumor cells, kidney, cells of the immune system (dendiritic, T cells, B cells, antigen-presenting cells, macrophages), exocrine cells (pancreas, salivary glands), prostate, adrenal gland, thyroid gland, eye structures (retinal cells), respiratory cells (cells of the lung, nose, respiratory tract), and endothelial cells.

VI. Biologically Active Compounds Containing very and/or Extremely pH-Labile Bonds The invention specifies compounds of the following general structure: A-B-C wherein A is a biologically active compound such as pharmaceuticals, drugs, proteins, peptides, hormones, cytokines, enzymes and nucleic acids such as anti-sense, ribozyme, recombining nucleic acids, and expressed genes; B is a labile linkage that contains a pH-labile bond such as amides of 2,3-dimethylmaleamic acid, enol ethers, enol esters, silyl ethers, and silyl enol ethers; and C is a compound. In one embodiment C is a compound that modifies the activity, function, delivery, transport, shelf-life, pharmacokinetics, blood circulation time in vivo, tissue and organ targetting, and sub-cellular targeting of the biologically active compound A. In other embodiments, B is a labile linkage that contains acetals, ketals, enol ethers, enol esters, amides, imines, imminiums, enamines, silyl ethers, or silyl enol ethers.

The invention also specifies that the labile linkage B is attached to reactive functional groups on the biologically active compound A. In yet another embodiment, reactive functional groups are attached to nucleic acids. Specifically, aziridines, quinones, oxiranes, epoxides, nitrogen mustards, sulfur mustards, and halogen and carbon-containing compounds such as alkylhalides, halo-amines, alpha-halo amides, esters and acids, may be used to modify nucleic acids and thereby attach reactive functional groups.

VII. pH-Labile Amphipathic Compounds

In one specification of the invention, the pH-labile and very pH-labile linkages and bonds are used within amphipathic compounds and detergents. The pH-labile amphipathic compounds can be incorporated into liposomes for delivering biologically active compounds and nucleic acids to cells. The detergents can be used for cleaning purposes and for modifying the solubility of biologically active compounds such as proteins. pH-labile surfactants may be desirable for their reversible solubilization of hydrophobic compounds in water and hydrophilic compounds in organic solvents. For example, surfactants are necessary for the purification of membrane proteins; however, it is often difficult to separate membrane proteins and surfactants once the purification is complete. Labile surfactants may also be more biodegradable and may reverse the formation of unwanted emulsions or foams.

For example the surfactant glycolic acid ethoxylate(4 units) 4-tert-buty-phenyl ether was converted in the enol-ether-containing pH-labile surfactant glycolic acid ethoxylate(4 units) 4-tert-buty-1,4-cyclohexadiene ether by ammonia-metal reduction of the phenyl group. The enol-ether bond links the hyrdrophilic portion of the molecule with the hydrophobic portion of the molecule, therefore, cleavage of the enol ether bond renders the amphiphilic surfactant into two separate molecules (one hydrophilic and one hydrophobic). The half-life of enol ether cleavage was 40 minutes at pH 5. In likewise manner, similar surfactants such as Triton X-100 may be converted into pH-labile surfactants.

I) Delivery Systems

In some embodiments of the present invention, the labile group (e.g., ester, amide or thioester acid) is complexed with lipids and liposomes so that in acidic environments the lipids are modified and the liposome becomes disrupted, fusogenic or endosomolytic. For example, the lipid diacylglycerol is reacted with an anhydride to form an ester acid. After acidification in an intracellular vesicle the diacylglycerol reforms and is very lipid bilayer disruptive and fusogenic.

In preferred embodiments of the present invention the delivery systems comprise polymers.

One of the several methods of nucleic acid delivery to the cells is the use of DNA-polycation complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective.

In addition to the delivery of polynucleotides, other bioactive molecules, such as proteins and small molecule drugs, may be delivered using a labile connection. Either through a direct modification of the bioactive molecule or through the formation of a complex with the molecule, which is itself labile.

EXAMPLES

Example 1

Synthesis and Characterization of Labile Compounds

A) Synthesis of 2-propionic-3-methylmaleic anhydride (carboxydimethylmaleic anhydride or C-DM): To a suspension of sodium hydride (0.58 g, 25 mmol) in 50 mL anhydrous tetrahydrofuran was added triethyl-2-phosphonopropionate (7.1 g, 30 mmol). After bubbling of hydrogen gas stopped, dimethyl-2-oxoglutarate (3.5 g, 20 mmol) in 10 mL anhydrous tetrahydrofuran was added and stirred for 30 minutes. Water, 10 mL, was then added and the tetrahydrofuran was removed by rotary evaporation. The resulting solid and water mixture was extracted with 3×50 mL ethyl ether. The ether extractions were combined, dried with magnesium sulfate, and concentrated to a light yellow oil. The oil was purified by silica gel chromatography elution with 2:1 ether:hexane to yield 4 gm (82% yield) of pure triester. The 2-propionic-3-methylmaleic anhydride then formed by dissolving of this triester into 50 mL of a 50/50 mixture of water and ethanol containing 4.5 g (5 equivalents) of potassium hydroxide. This solution was heated to reflux for 1 hour. The ethanol was then removed by rotary evaporation and the solution was acidified to pH 2 with hydrochloric acid. This aqueous solution was then extracted with 200 mL ethyl acetate, which was isolated, dried with magnesium sulfate, and concentrated to a white solid. This solid was then recrystallized from dichloromethane and hexane to yield 2 g (80% yield) of 2-propionic-3-methyl-maleic anhydride.

B) Synthesis of 2,3-dioleoyldiaminopropionic ethylenediamine amide: 2,3-diaminopropionic acid (1.4 gm, 10 mmol) and dimethylaminopyridine (1.4 gm 11 mmol) were dissolved in 50 mL of water. To this mixture was added over 5 minutes with rapid stirring oleoyl chloride (7.7 mL, 22 mmol) of in 20 mL of tetrahydrofuran. After all of the acid chloride had been added, the solution was allowed to stir for 30 minutes. The pH of the solution was 4 at the end of the reaction. The tetrahydrofuran was removed by rotary evaporation. The mixture was then partitioned between water and ethyl acetate. The ethyl acetate was isolated, dried with magnesium sulfate, and concentrated by rotary evaporation to yield a yellow oil. The 2,3-dioleoyldiaminopropionic acid was isolated by silica gel chromatography, elution with ethyl ether to elute oleic acid, followed by 10% methanol 90% methylene chloride to elute diamide product, 1.2 g (19% yield). The diamide (1.1 gm, 1.7 mmol) was then dissolved in 25 mL of methylene chloride. To this solution was added N-hydroxysuccinimide (0.3 g. 1.5 eq) and dicyclohexylcarbodiimide (0.54 g, 1.5 eq). This mixture was allowed to stir overnight. The solution was then filtered through a cellulose plug. To this solution was added ethylene diamine (1 gm, 10 eq) and the reaction was allowed to proceed for 2 hours. The solution was then concentrated by rotary evaporation. The resulting solid was purified by silica gel chromatography elution with 10% ammonia saturated methanol and 90% methylene chloride to yield the triamide product 2,3-dioleoyldiaminopropionic ethylenediamine amide (0.1 gm, 9% yield). The triamide product was given the number MC213.

C) Synthesis of dioleylamideaspartic acid: N-(tert-butoxycarbonyl)-L-aspartic acid (0.5 gm, 2.1 mmol) was dissolved in 50 mL of acetonitrile. To this solution was added N-hydroxysuccinimide (0.54 gm, 2.2 eq) and was added dicyclohexylcarbodiimide (0.54 g, 1.5 eq). This mixture was allowed to stir overnight. The solution was then filtered through a cellulose plug. This solution was then added over 6 hours to a solution containing oleylamine (1.1 g, 2 eq) in 20 mL methylene chloride. After the addition was complete the solvents were removed by rotary evaporation. The resulting solid was partitioned between 100 mL ethyl acetate and 100 mL water. The ethyl acetate fraction was then isolated, dried by sodium sulfate, and concentrated to yield a white solid. The solid was dissolved in 10 mL of triflouroacetic acid, 0.25 mL water, and 0.25 mL triisopropylsilane. After two hours, the triflouroacetic acid was removed by rotary evaporation. The product was then isolated by silica gel chromatography using ethyl ether followed by 2% methanol 98% methylene chloride to yield 0.1 gm (10% yield) of pure dioleylamideaspartic acid, which was given the number MC303.

D) Synthesis of 2,3-dimethylmaleamic poly-L-lysine: Poly-L-lysine (10 mg 34,000 MW Sigma Chemical ) was dissolved in 1 mL of aqueous potassium carbonate (100 mM). To this solution was added 2,3-dimethylmaleic anhydride (100 mg, 1 mmol) and the solution was allowed to react for 2 hr. The solution was then dissolved in 5 mL of aqueous potassium carbonate (100 mM) and dialyzed against 3×2 L water that was at pH8 with addition of potassium carbonate. The solution was then concentrated by lyophilization to 10 mg/mL of 2,3-dimethylmaleamic poly-L-lysine.

E) Synthesis of dimethylmaleamic-melittin and dimethylmaleamic-pardaxin. Solid melittin or pardaxin (100 μg) was dissolved in 100 μL of anhydrous dimethylformamide containing 1 mg of 2,3-dimethylmaleic anhydride and 6 μL of diisopropylethylamine.

F) Synthesis of dimethylmaleamic derivatives (from alcohol-containing) and dimethylmaleamic derivatives (from amine-containing) of lipids: To a solution of 1 mg of lipid (either MC 213, MC 303, phosphatidylethanolamine dioleoyl (DOPE), or 1,2-dioleoylglycerol (DOG)) in chloroform (0.1 mL) is added 10 mg of 2,3-dimethylmaleic anhydride and 82 mg of diisopropylethyl amine. The solution is allowed to incubate at room temperature for 1 hour before testing for activity.

G) Synthesis of 2-propionic-3-methylmaleic derivatives (from alcohol-containing) and 2-propionic-3-methylmaleamic derivatives (from amine-containing) of lipids: To a solution of 1 mg of lipid (either MC 213, MC 303, phosphatidylethanolamine dioleoyl (DOPE), or 1,2-dioleoylglycerol (DOG)) in chloroform (0.1 mL) is added 10 mg of 2-propionic-3-methylmaleic anhydride and 82 mg of diisopropylethyl amine. The solution is allowed to incubate at room temperature for 1 hour before testing for activity.

H) Synthesis of adducts between peptide and poly-L-lysine adducts: To a solution of poly-L-lysine (10 mg, 0.2 μmol) and peptides $KL_3$ or melittin (2 μmol) is added 1-(3-dimethylaminopropyl)-3-ethylcarbodiimide hydrochloride (20 μmol). For the peptide $KL_3$, the reaction is performed in 2 mL of water. For the peptide melittin, the reaction is performed in a solution of 1 mL water and 1 mL triflouroethanol. The reaction is allowed to proceed overnight before placement into a 12,000 molecular weight cutoff dialysis bag and dialysis against 4×2 liters over 48 hours. The amount of coupled peptide is determined by the absorbance of the tryptophan residue at 280 nm, using an extinction coefficient of 5690 $cm^{-1}M^{-1}$ (Gill, S. C. and von Hippel, P. H. Analytical Biochemistry (1989) 182, 319–326). The conjugate of melittin and poly-L-lysine was determined to have 4 molecules of melittin per molecule of poly-L-lysine and is referred to as mel-PLL. The conjugate of $KL_3$ and poly-L-lysine was determined to have 10 molecules of $KL_3$ per molecule of poly-L-lysine and is referred to as $KL_3$-PLL.

I) Synthesis of adducts between peptide and polyallylamine adducts: To a solution of polyallylamine (10 mg, 0.2 μmol) and peptides $KL_3$ or melittin (2 μmol) is added 1-(3-dimethylaminopropyl)-3-ethylcarbodiimide hydrochloride (20 μmol). For the peptide $KL_3$, the reaction is performed in 2 mL of water. For the peptide melittin, the reaction is performed in a solution of 1 mL water and 1 mL triflouroethanol. The reaction is allowed to proceed overnight before placement into a 12,000 molecular weight cutoff dialysis bag and dialysis against 4×2 liters over 48 hours to remove uncoupled peptide. The amount of coupled peptide is determined by the absorbance of the tryptophan residue at 280 nm, using an extinction coefficient of 5690 $cm^{-1}M^{-1}$ (Gill, S. C. and von Hippel, P. H. Analytical Biochemistry (1989) 182, 319–326). The conjugate melittin and polyallylamine was determined to have 4 molecules of melittin per molecule of polyallylamine and is referred to as mel-PAA. The conjugate of $KL_3$ and polyallylamine was determined to have 10 molecules of $KL_3$ per molecule of polyallylamine and is referred to as $KL_3$-PAA.

J) Synthesis of polyethyleneglycol methyl ether 2-propionic-3-methylmaleate (CDM-PEG): To a solution of 2-propionic-3-methylmaleic anhydride (30 mg, 0.16 mmol) in 5 mL methylene chloride was added oxalyl chloride (200 mg, 10 eq) and dimethylformamide (1 μL). The reaction was allowed to proceed overnight at which time the excess oxalyl chloride and methylene chloride were removed by rotary evaporation to yield the acid chloride, a clear oil. The acid chloride was dissolved in 1 mL of methylene chloride. To this solution was added polyethyleneglycol monomethyl ether, molecular weight average of 5,000 (815 mg, 1 eq) and pyridine (20 μL, 1.5 eq) in 10 mL of methylene chloride. The solution was then stirred overnight. The solvent was then removed and the resulting solid was dissolved into 8.15 mL of water.

K) General procedure for the reaction of mel-PAA, KL$_3$-PAA, mel-PLL, and KL$_3$-PLL with dimethylmaleic anhydride and 2-propionic-3-methylmaleic anhydride: Peptide-polycation conjugates (10 mg/mL) in water were reacted with a ten-fold weight excess of dimethylmaleic anhydride and a ten-fold weight excess of potassium carbonate. Analysis of the amine content after 30 by addition of peptide solution to 0.4 mM trinitrobenzene sulfonate and 100 mM borax revealed no detectable amounts of amine.

L) Synthesis of glycolic acid ethoxylate(4 units) 4-tert-buty-1,4-cyclohexadiene ether (an enolether containing detergent): To a solution of glycolic acid ethoxylate(4 units) 4-tert-buty-phenyl ether (100 mg, 0.26 mmol), t-butylalcohol (10 mL), and tetrahydrofuran (10 mL) was condensed liquid anhydrous ammonia (20 mL) at −78° C. To this solution was added sodium metal (100 mg, 16 eq). The solution turned dark blue and was stirred for 4 hours during which time the blue color remained. The solution was then quenched by the addition of ammonium chloride (220 mg, 16 eq). The ammonia was allowed to evaporate overnight. The mixture was then partitioned between 10 mL of water and 10 mL ethyl ether. The water layer was isolated and used for kinetic studies.

M) Synthesis of poly(oxy-1-para-aceticphenoxymethyl-ethylene-co-oxy-1-methylethylene): To para-hydroxyphenylacetic acid (0.115 gm, 0.75 mmol) was added a 1 M solution of tetrabutylammonium hydroxide in methanol. The methanol was then removed by rotary evaporation to yield an oil. To this was added 5 mL of tetrahydrofuran and polyepichlorohydrin (0.046 gm, 0.6 mg). The solution was then heated to 60° C. for 16 hours. The solution was then placed into dialysis tubing (12,000 molecular weight cutoff) and dialyzed against 2×1 L of water that was pH 9 with addition of potassium carbonate. A portion of this solution was filtered through a 0.2 µm nylon syringe filter, and then lyophilized to determine its concentration. This solution was used for particle formation and hydrolysis studies.

N) Synthesis of L-cystine-1,4-bis(3-aminopropyl)piperazine copolymer: To a solution of N,N'-Bis(t-BOC)-L-cystine (85 mg, 0.15 mmol) in ethyl acetate (20 mL) was added N,N'-dicyclohexylcarbodiimide (108 mg, 0.5 mmol) and N-hydroxysuccinimide (60 mg, 0.5 mmol). After 2 hr, the solution was filtered through a cotton plug and 1,4-bis(3-aminopropyl)piperazine (54 µL, 0.25 mmol) was added. The reaction was allowed to stir at room temperature for 16 h. The ethyl acetate was then removed by rotary evaporation and the resulting solid was dissolved in trifluoroacetic acid (9.5 mL), water (0.5 mL) and triisopropylsilane (0.5 mL). After 2 h, the trifluoroacetic acid was removed by rotary evaporation and the aqueous solution was dialyzed in a 15,000 MW cutoff tubing against water (2×2l) for 24 h. The solution was then removed from dialysis tubing, filtered through 5 µM nylon syringe filter and then dried by lyophilization to yield 30 mg of polymer.

Synthesis of Acid Labile Monomers:

O) Synthesis of Di-(2-methyl-4-hydroxymethyl-1,3-dioxolane)-1,4-benzene (MC 216): To a solution of diacetylbenzene (2.00 g, 12.3 mmol, Aldrich Chemical Company) in toluene (30.0 mL), was added glycerol (5.50 g, 59.7 mmol, Acros Chemical Company) followed by p-toluenesulfonic acid monohydrate (782 mg, 4.11 mmol, Aldrich Chemical Company). The reaction mixture was heated at reflux for 5 hrs with the removal of water by azeotropic distillation in a Dean-Stark trap. The reaction mixture was concentrated under reduced pressure, and the residue was taken up in Ethyl Acetate. The solution was washed 1×10% NaHCO$_3$, 3×H$_2$O, 1× brine, and dried (MgSO$_4$). Following removal of solvent (aspirator), the residue was purified by flash chromatography on silica gel (20×150 mm, CH$_2$Cl$_2$ eluent) to afford 593 mg (16% yield) of di-(2-methyl-4-hydroxymethyl-1,3-dioxolane)-1,4-benzene. Molecular ion calculated for C$_{16}$H$_{22}$O$_6$ 310. found m+1/z 311.2. 300 MHz NMR (CDCl$_3$, ppm) δ 7.55–7.35 (4H, m) 4.45–3.55 (10H, m) 1.65 (6 H, brs).

P) Di-(2-methyl-4-hydroxymethyl(succinic semialdehyde ester)-1,3-dioxolane)-1,4-benzene (MC 211): To a solution of succinic semialdehyde (150 mg, 1.46 mmol, Aldrich Chemical Company) and di-(2-methyl-4-hydroxymethyl-1,3-dioxolane)-1,4-benzene (150 mg, 480 µmol) in CH$_2$Cl$_2$ (4 mL) was added dicyclohexylcarbodiimide (340 mg, 1.65 mmol, Aldrich Chemical Company) followed by a catalytic amount of 4-dimethylaminopyridine. The solution was stirred for 30 min and filtered. Following removal of solvent (aspirator), the residue was purified by flash chromatography on silica gel (20×150 mm, CH$_2$Cl$_2$ eluent) to afford 50 mg (22%) of di-(2-methyl-4-hydroxymethyl(succinic semialdehyde ester)-1,3-dioxolane)-1,4-benzene. Molecular ion calculated for C$_{24}$H$_{30}$O$_{10}$ 478.0. found m+1/z 479.4.

Q) Di-(2-methyl-4-hydroxymethyl(glyoxilic acid ester)-1,3-dioxolane)-1,4-benzene (MC225): To a solution of glyoxylic acid monohydrate (371 mg, 403 µmol, Aldrich Chemical Company) and di-(2-methyl-4-hydroxymethyl-1,3-dioxolane)-1,4-benzene (500 mg, 161 µmol) in dimethylformamide (8 mL) was added dicyclohexylcarbodiimide (863 mg, 419 µmol, Aldrich Chemical Company). The solution was stirred for 30 min and filtered. Following removal of solvent (aspirator), the residue was purified by flash chromatography on silica gel (20×150 mm, ethylacetate/Hexanes (1:2.3 eluent) to afford 58 mg (10%) of di-(2-methyl-4-hydroxymethyl(glyoxylic acid ester)-1,3-dioxolane)-1,4-benzene.

R) Di-(2-methyl-4-aminomethyl-1,3-dioxolane)-1,4-benzene (MC372). To a solution of 1,4-diacetylbenzene (235 mg, 1.45 mmol, Aldrich Chemical Company) in toluene (15.0 mL) was added 3-amino-1,2-propanediol protected as the FMOC carbamide (1.0 g, 3.2 mmol), followed by a catalytic amount of p-toluenesulfonic acid monohydrate (Aldrich Chemical Company). The reaction mixture was heated at reflux for 16 hrs with the removal of water by azeotropic distillation in a Dean-Stark trap. The reaction mixture was cooled to room temperature, partitioned in toluene/H$_2$O, washed 1×10% NaHCO$_3$, 3×H$_2$O, 1× brine, and dried (MgSO$_4$). The extract was concentrated under reduced pressure and crystallized (methanol/H$_2$O). The protected amine ketal was identified in the supernatant, which was concentrated to afford 156 mg product. The free amine was generated by treating the ketal with piperidine in dichloromethane for 1 hr.

S) Di-(2-methyl-4-hydroxymethyl(glycine ester)-1,3-dioxolane)-1,4-benzene (MC373): To a solution of FMOC-Glycine (690 mg, 2.3 mmol, NovaBiochem) in dichloromethane (4.0 mL) was added dicyclohexylcarbodiimide (540 mg, 2.6 mmol, Aldrich Chemical Company). After 5 minutes, di-(2-methyl-4-hydroxymethyl-1,3-dioxolane)-1,4-benzene (240 mg, 770 µmol) was added followed by a catalytic amount of 4-dimethylaminopyridine. After 20 min, the reaction mixture was filtered and concentrated (aspirator) to afford 670 mg of oil. The residue was taken in tetrahydrofuran (4.0 mL) and piperidine (144 mg, 1.7 mmol) was added. The reaction was stirred at room temperature for 1 hr and added to cold diethyl ether. The resulting solid was washed 3× diethyl ether to afford di-(2-methy-4-hydroxymethyl(glycine ester)-1,3-dioxolane)-1,4,benzene. Molecular ion calculated for $C_{20}H_{28}N_2O_8$ 424. found m+1/z 425.2.

Synthesis of Polymers Containing Acid Labile Moieties:

T) Di-(2-methyl-4-hydroxymethyl(glyoxilic acid ester)-1,3-dioxolane)-1,4-benzene:1,4-Bis(3-aminopropyl)piperazine Copolymer (1:1) (MC228): To a solution of di-(2-methyl-4-hydroxymethyl(glyoxylic acid ester)-1,3-dioxolane) 1,4-benzene (100 mg, 0.273 mmol) in dimethylformamide was added 1,4-bis(3-aminopropyl)-piperazine (23 µL, 0.273 mmol, Aldrich Chemical Company) and the solution was heated to 80° C. After 16 hrs the solution was cooled to room temperature and precipitated with diethyl ether. The solution was decanted and the residue washed with diethyl ether (2×) and dried under vacuum to afford di-(2-methyl-4-hydroxymethyl(glyoxylic acid ester)-1,3-dioxolane) 1,4-benzene: 1,4-bis(3-aminopropyl)-piperazine copolymer (1:1).

By similar methods, the following polymers were constructed:

Di-(2-methyl-4-hydroxymethyl(succinic semialdehyde ester)-1,3-dioxolane)-1,4-benzene:
   1,4-Bis(3-aminopropyl)piperazine Copolymer (1:1) (MC208).

Di-(2-methyl-4-hydroxymethyl(succinic semialdehyde ester)-1,3-dioxolane)-1,4-benzene:
   1,4-Bis(3-aminopropyl)piperazine Copolymer (1:1) Reduced with NaCNBH$_3$ (MC301).

Di-(2-methyl-4-hydroxymethyl(succinic semialdehyde ester)-1,3-dioxolane)-1,4-benzene:
   1,3-Diaminopropane Copolymer (1:1) (MC300).

Di-(2-methyl-4-hydroxymethyl(succinic semialdehyde ester)-1,3-dioxolane)-1,4-benzene:
   3,3'-Diamino-N-methyldipropylamine Copolymer (1:1) (MC218).

Di-(2-methyl-4-hydroxymethyl(succinic semialdehyde ester)-1,3-dioxolane)-1,4-benzene:
   Tetraethylenepentamine Copolymer (1:1) (MC217).

Di-(2-methyl-4-hydroxymethyl(glyoxilic acid ester)-1,3-dioxolane)-1,4-benzene: 1,3-Diaminopropane Copolymer (1:1) (MC226).

Di-(2-methyl-4-hydroxymethyl(glyoxilic acid ester)-1,3-dioxolane)-1,4-benzene: 3,3'-Diamino-N-methyldipropylamine Copolymer (1:1) (MC227).

U) Synthesis of 1,4-Bis(3-aminopropyl)piperazine—Glutaric Dialdehyde Copolymer (MC140): 1,4-Bis(3-aminopropyl)piperazine (206 µL, 0.998 mmol, Aldrich Chemical Company) was taken up in 5.0 mL H$_2$O. Glutaric dialdehyde (206 µL, 0.998 mmol, Aldrich Chemical Company) was added and the solution was stirred at room temperature. After 30 min, an additional portion of H$_2$O was added (20 mL), and the mixture neutralized with 6 N HCl to pH 7, resulting in a red solution. Dialysis against H$_2$O (3×3 L, 12,000–14,000 MWCO) and lyophilization afforded 38 mg (14%) of the copolymer.

By similar methods, the following polymers were constructed:

Diacetylbenzene-1,3-Diaminopropane Copolymer (1:1) (MC321)

Diacetylbenzene-Diamino-N-methyldipropylamine Copolymer (1:1) (MC322).

Diacetylbenzene-1,4-Bis(3-aminopropyl)piperazine Copolymer (1:1) (MC229)

Diacetylbenzene-Tetraethylenepentamine Copolymer (1:1) (MC323).

Glutaric Dialdehyde-1,3-Diaminopropane Copolymer (1:1) (MC324)

Glutaric Dialdehyde-Diamino-N-methyldipropylamine Copolymer (1:1) (MC325).

Glutaric Dialdehyde-Tetraethylenepentamine Copolymer (1:1) (MC326).

1,4-Cyclohexanone-1,3-Diaminopropane Copolymer (1:1) (MC330)

1,4-Cyclohexanone-Diamino-N-methyldipropylamine Copolymer (1:1) (MC33 1).

1,4-Cyclohexanone-1,4-Bis(3-aminopropyl)piperazine Copolymer (1:1) (MC312)

1,4-Cyclohexanone-Tetraethylenepentamine Copolymer (1:1) (MC332).

2,4-Pentanone-1,4-Bis(3-aminopropyl)piperazine Copolymer (1:1) (MC340)

2,4-Pentanone-Tetraethylenepentamine Copolymer (1:1) (MC347).

1,5-Hexafluoro-2,4-Pentanone-1,4-Bis(3-aminopropyl)piperazine Copolymer (1:1) (MC339)

1,5-Hexafluoro-2,4-Pentanone-Tetraethylenepentamine Copolymer (1:1) (MC346).

V) Synthesis of Poly-L-Glutamic acid (octamer)—Glutaric Dialdehyde Copolymer (MC151): H$_2$N-SEQ ID NO: 11-NHCH$_2$CH$_2$NH$_2$ (; 5.5 mg, 0.0057 mmol, Genosis) was taken up in 0.4 mL H$_2$O. Glutaric dialdehyde (0.52 µL, 0.0057 mmol, Aldrich Chemical Company) was added and the mixture was stirred at room temperature. After 10 min the solution was heated to 70° C. After 15 hrs, the solution was cooled to room temperature and dialyzed against H$_2$O (2×2 L, 3500 MWCO). Lyophilization afforded 4.3 mg (73%) poly-glutamic acid (octamer)—glutaric dialdehyde copolymer.

W) Synthesis of Di-(2-methyl-4-aminomethyl-1,3-dioxolane)-1,4-benzene—Glutaric Dialdehyde Copolymer (MC352): To a solution of di-(2-methyl-4-aminomethyl-1,3-dioxolane)-1,4-benzene (23 mg, 75 µmol) in dimethylformamide (200 µL) was added glutaric dialdehyde (7.5 mg, 75 µmol, Aldrich Chemical Company). The reaction mixture was heated at 80° C. for 6 hrs under nitrogen. The solution was cooled to room temperature and used without further purification.

X) Synthesis of Di-(2-methy-4-hydroxymethyl(glycine ester)-1,3-dioxolane)-1,4,benzene—Glutaric Dialdehyde Copolymer (MC357): To a solution of di-(2-methy-4-hydroxymethyl(glycine ester)-1,3-dioxolane)-1,4,benzene (35 mg, 82 µmol) in dimethylformamide (250 µL) was added glutaric dialdehyde (8.2 mg, 82 µmol, Aldrich Chemical Company). The reaction mixture was heated at 80° C. for 12 hrs. The solution was cooled to room temperature and used without further purification.

Y) Synthesis of Polyvinyl(2-phenyl-4-hydroxymethyl-1,3-dioxolane) from the reaction of Polyvinylphenyl Ketone and Glycerol: Polyvinyl phenyl ketone (500 mg, 3.78 mmol, Aldrich Chemical Company) was taken up in 20 mL dichloromethane. Glycerol (304 µL, 4.16 mmol, Acros Chemical Company) was added followed by p-toluenesulfonic acid monohydrate (108 mg, 0.57 mmol, Aldrich Chemical Company). Dioxane (10 mL) was added and the solution was stirred at room temperature overnight. After 16 hrs, TLC indicated the presence of ketone. The solution was concentrated under reduced pressure, and the residue dissolved in dimethylformamide (7 mL). The solution was heated to 60° C. for 16 hrs. After 16 hrs, TLC indicated the ketone had been consumed. Dialysis against H$_2$O (1×3 L, 3500 MWCO), followed by lyophilization resulted in 606 mg (78%) of the ketal. Ketone was not observed in the sample by TLC analysis, however, upon treatment with acid, the ketone was again detected.

Z) Synthesis of Polyvinyl(2-methyl-4-hydroxymethyl (succinic anhydride ester)-1,3-dioxolane: To a solution of polyvinyl(2-methyl-4-hydroxymethyl-1,3-dioxolane) (220 mg, 1.07 mmol) in dichloromethane (5 mL) was added succinic anhydride (161 mg, 1.6 mmol, Sigma Chemical Company), followed by diisopropylethyl amine (0.37 mL, 2.1 mmol, Aldrich Chemical Company) and the solution was heated at reflux. After 16 hrs, the solution was concentrated, dialyzed against $H_2O$ (1×3 L, 3500 MWCO), and lyophilized to afford 250 mg (75%) of the ketal acid polyvinyl (2-methyl-4-hydroxymethyl(succinic anhydride ester)-1,3-dioxolane.

AA) Synthesis of Ketal from Polyvinyl Alcohol and 4-Acetylbutyric Acid: Polyvinylalcohol (200 mg, 4.54 mmol, 30,000–60,000 MW, Aldrich Chemical Company) was taken up in dioxane (10 mL). 4-acetylbutyric acid (271 µL, 2.27 mmol, Aldrich Chemical Company) was added followed by p-toluenesulfonic acid monohydrate (86 mg, 0.45 mmol, Aldrich Chemical Company). After 16 hrs, TLC indicated the presence of ketone. The solution was concentrated under reduced pressure, and the residue dissolved in dimethylformamide (7 mL). The solution was heated to 60° C. for 16 hrs. After 16 hrs, TLC indicated the loss of ketone in the reaction mixture. Dialysis against $H_2O$ (1×4 L, 3500 MWCO), followed by lyophilization resulted in 145 mg (32%) of the ketal. Ketone was not observed in the sample by TLC analysis, however, upon treatment with acid, the ketone was again detected.

AB) Partial Esterification of Poly-Glutamic Acid with Di-(2-methyl-4-hydroxymethyl-1,3-dioxolane)-1,4-benzene (MC 196): To a solution of poly-L-glutamic acid (103 mg, 792 µmol, 32,000 MW, Sigma Chemical Company) in sodium phosphate buffer (30 mM) was added 1-(3-dimethylaminopropyl)-3-ethylcarbodiimide hydrochloride (129 mg, 673 µmol, Aldrich Chemical Company), followed by di-(2-methyl-4-hydroxymethyl-1,3-dioxolane)-1,4-benzene (25.0 mg, 80.5 µmol), and a catalytic amount of 4-dimethylaminopyridine. After 12 hrs, the reaction mixture was dialyzed against water (2×1 L, 12,000–14,000 MWCO) and lyophilized to afford 32 mg of poly-glutamic acid partially esterified with di-(2-methyl-4-hydroxymethyl-1,3-dioxolane)-1,4-benzene.

AC) Aldehyde Derivatization of the Poly-Glutamic Acid Partially Esterified with Di-(2-methyl-4-hydroxymethyl-1, 3-dioxolane)-1,4-benzene: To a solution of succinic semialdehyde (2.4 mg, 23 µmol, Aldrich Chemical Company) in water (100 µL) was added 1-(3-dimethylaminopropyl)-3-ethylcarbodiimide hydrochloride (4.7 mg, 2.4 µmol, Aldrich Chemical Company) followed by N-hydroxysuccinimide (2.8 mg, 24 µmol, Aldrich Chemical Company). The reaction was stirred at room temperature for 20 min. Formation of the N-hydroxysuccinic ester of succinic semialdehyde was confirmed by mass spectrometry.

Poly-glutamic acid partially esterified with di-(2-methyl-4-hydroxymethyl-1,3-dioxolane)-1,4-benzene (15.0 mg, 115 µmol) was taken up in water (100 µL) and added to the N-hydroxysuccinic ester of succinic semialdehyde, followed by a crystal of 4-dimethylaminopyridine. The reaction mixture was stirred overnight at room temperature. After 12 hrs the reaction mixture was dialyzed against water (2×1 L, 12,000–14,000 MWCO) and lyophilized to afford 3.0 mg. After dialysis the product tested positive for aldehyde content with 2,4-di-nitrophenylhydrazine.

AD) Synthesis of a Silyl Ether from Polyvinylalcohol and 3-Aminopropyl-trimethoxysilane (MC221): To a solution of polyvinylalcohol (520 mg, 11.8 mmol (OH), 30,000–70,000 MW, Sigma Chemical Company) in dimethylformamide (4 mL) was added 3-aminopropyltrimethoxysilane (1.03 mL, 5.9 mmol, Aldrich Chemical Company) and the solution was stirred at room temperature. After 2.5 hrs, a 20 µL aliquot of the reaction mixture was removed and added to pDNA (pCI Luc) (100 µg) in 25 mM HEPES buffer at pH 7.5 (500 µL) to test for polyamine formation (pDNA:amine 1:3). Particle sizing (Brookhaven Instruments Coporation, ZetaPlus Particle Sizer, I90, 532 nm) indicated an effective diameter of 3000 nm (1.3 mcps) indicating pDNA condensation and particle formation. An aliquot of 1 N HCl (40 µL) was added to the sample, and the particle size was again measured. After 1 min of exposure to the acidic conditions, the particle size was 67,000 nm (600 kcps). After 10 min, particles were no longer present within the sample. The sample was dried under high vacuum to afford 1.0 g (83%) white solid.

By similar methods, the following polymers were constructed:

Silyl Ether from Poly-L-Arginine/-L-Serine(3:1) and 3-Aminopropyltrimethoxysilane (2:1) (MC358): Poly-L-Arginine/-L-Serine(3:1) (20,000–50,000 MW, Sigma Chemical Company), 3-Aminopropyltrimethoxysilane (Aldrich Chemical Company)

Silyl Ether from Poly-DL-Serine and 3-Aminopropyltrimethoxysilane (3:1) (MC366): Poly-DL-Serine (5,000–15,000 MW, Sigma Chemical Company), 3-Aminopropyl-trimethoxysilane (Aldrich Chemical Company)

Silyl Ether from Poly-DL-Serine and 3-Aminopropyltrimethoxysilane (2:1) (MC367). Poly-DL-Serine (5,000–15,000 MW, Sigma Chemical Company), 3-Aminopropyl-trimethoxysilane (Aldrich Chemical Company)

Silyl Ether from Poly-DL-Serine and N-[3-(Triethoxysilyl) propyl]-4,5-dihydroimidizole (3:1) (MC369): Poly-DL-Serine (5,000–15,000 MW, Sigma Chemical Company)

N-[3-(Triethoxysilyl)propyl]-4,5-dihydroimidizole (United Chemical Technologies, Incorporated)

Silyl Ether from Poly-DL-Serine and N-Trimethoxysilylpropyl-N,N,N-trimethylammonium chloride (3:1) (MC370): Poly-DL-Serine (5,000–15,000 MW, Sigma Chemical Company)

N-Trimethoxysilylpropyl-N,N,N-trimethylammonium chloride (United Chemical Technologies, Incorporated)

Silazane from Poly-L-Lysine and 3-Aminopropyltrimethoxysilane (2:1) (MC360). Poly(1,1-Dimethylsilazane) Tolemer (MC222): Sample was obtained from United Chemical Technologies, Incorporated.

Example 2

Transfection with pH-Sensitive Compounds and/or Membrane Active Agents

A) In Vitro Transfection with DNA-PLL-KL$_3$ and dimethylmaleamic KL$_3$: To a complex of plasmid DNA pCIluc (10 µg/mL, 0.075 mM in phosphate, 2.6 µg/µL pCIluc; prepared according to Danko, I., Williams, P., Herweijer, H. Zhang, G., Latendresse, J. S., Bock, I., Wolff, J. A. *Hum. Mol. Genetics* 1997, 6, 1435.) and poly-L-lysine (40 µg/mL) in 0.5 mL of 5 mM HEPES pH 7.5 was added succinylated poly-L-lysine (34,000 MW, Aldrich Chemical), 2,3-dimethylmaleamic melittin and 2,3-dimethylmaleamic KL$_3$. The DNA-poly-L-lysine-2,3-dimethylmaleamic peptide complexes were then added (200 µL) to wells containing 3T3 mouse embryonic fibroblast cells in 290 mM glucose and 5 mM HEPES buffer pH 7.5. After 1.5 h, the glucose media was replaced with Dubelco's modified Eagle Media and the cells were allowed to incubate for 48 h. The cells were then harvested and then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| Peptide | Relative Light Units (Relative to Succinylated poly-L-lysine) |
|---|---|
| Succinylated poly-L-lysine | 6410 (1) |
| $KL_3$ | 261 (0.04) |
| 2,3-dimethylmaleamic $KL_3$ | 49535 (7.7) |

B) In Vitro Transfection with DNA-PLL complexes with dimethylmaleamic $KL_3$ and dimethylmaleamic $KL_3$-PLL: To a complex of plasmid DNA pCIluc (10 µg/mL, prepared according to Danko, I., Williams, P., Herweijer, H. Zhang, G., Latendresse, J. S., Bock, I., Wolff, J. A. Hum. Mol. Genetics 1997, 6, 1435.) and poly-L-lysine (40 µg/mL) in 0.5 mL water was added 10 mg of 2,3-dimethylmaleamic -$KL_3$-PLL or 2,3-dimethylmaleamic -$KL_3$. The DNA-poly-L-lysine-2,3-dimethylmaleamic peptide complexes were then added (200 µL) to a well containing 3T3 mouse embryonic fibroblast cells in opti-MEM. After 4 h, the media was replaced with 90% Dubelco's modified Eagle Media and 10% fetal bovine serum the cells were then allowed to incubate for 48 h. The cells were then harvested and then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| 2,3-dimethylmaleamic peptide | Relative Light Units |
|---|---|
| 2,3-dimethylmaleamic $KL_3$ | 20927 |
| 2,3-dimethylmaleamic $KL_3$-PLL | 130478 |

C) In Vitro Transfection with DNA-PLL complexes with dimethylmaleamic $KL_3$-PLL, 2-propionic-3-methylmaleamic $KL_3$-PLL, and succinimic $KL_3$-PLL: To a complex of plasmid DNA pCIluc (10 µg/mL, prepared according to Danko, I., Williams, P., Herweijer, H. Zhang, G., Latendresse, J. S., Bock, I., Wolff, J. A. Hum. Mol. Genetics 1997, 6, 1435.) and poly-L-lysine (40 µg/mL) in 0.5 mL water was added 25 µg of 2,3-dimethylmaleamic -$KL_3$-PLL, 2-propionic-3-methylmaleamic $KL_3$-PLL, and succinimic $KL_3$-PLL. The DNA-poly-L-lysine-peptide complexes were then added (200 µL) to a well containing 3T3 mouse embryonic fibroblast cells in opti-MEM media. After 4 h, the media was replaced with 90% Dubelco's modified Eagle Media and 10% fetal bovine serum the cells were then allowed to incubate for 48 h. The cells were then harvested and then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| Modified peptide | Relative Light Units |
|---|---|
| 2,3-dimethylmaleamic $KL_3$-PLL | 96221 |
| 2-propionic-3-methylmaleamic $KL_3$-PLL | 102002 |
| succinimic $KL_3$-PLL | 21206 |

D) In Vitro Transfection with DNA-PLL with 2,3-dimethylmaleamic-modified lipids: To a complex of plasmid DNA pCIluc (10 µg/mL, 2.2 µg/µL pCIluc; prepared according to Danko, I., Williams, P., Herweijer, H. Zhang, G., Latendresse, J. S., Bock, I., Wolff, J. A. Hum. Mol. Genetics 1997, 6, 1435.) and poly-L-lysine (40 µg/mL) in 0.5 mL of deionized water was added 800 µg glycine followed by 40 µg 2,3-dimethylmaleic DOG, 2,3-dimethylmaleamicMC213, 2,3-dimethylmaleamicMC303, or 2,3-dimethylmaleamic-DOPE. The DNA-poly-L-lysine-2,3-dimethylmaleamic-modified lipids were then added (200 µL) to a well containing opti-MEM media. After 4 h, the media was replaced with 90% Dubelco's modified Eagle Media and 10% fetal bovine serum the cells were then allowed to incubate for 48 h. The cells were then harvested and then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| 2,3-dimethylmaleamic-modified lipids | Relative Light Units (Relative topoly-L-lysine) |
|---|---|
| No lipid | 6000 (1) |
| MC213 | 91356 (15) |
| MC303 | 469756 (78) |
| DOPE | 243359 (40) |
| DOG | 193624 (32) |

E) Transfection of HELA Cells with Histone H1 and the Membrane Active peptide melittin, dimethylmaleic modified melittin or succinic anhydride modifed melittin:

Three Complexes were Formed:

Complex I) To 300 µL Opti-MEM was added Histone H1(12 µg, Sigma Corporation) followed by the peptide Melittin (20 µg) followed by pDNA (pCI Luc, 4 µg).

Complex II) To 300 µL Opti-MEM was added Histone H1(12 µg, Sigma Corporation) followed by the 2,3-dimethylmaleic modified peptide Melittin (20 µg) followed by pDNA (pCI Luc, 4 µg).

Complex III) To 300 µL Opti-MEM was added Histone H1(12 µg, Sigma Corporation) followed by the succinic anhydride modified peptide Melittin (20 µg) followed by pDNA (pCI Luc, 4 µg).

Transfections were carried out in 35 mm wells. At the time of transfection, HELA cells, at approximately 60% confluency, stored in complete growth media, DMEM with 10% fetal bovine serum (Sigma). 150 µL of complex was added to each After an incubation of 48 hours, the cells were harvested and the lysate was assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

Results:
Complex I: RLU=2,161
Complex II: RLU=105,909
Complex III: RLU=1,056

The 2,3-dimethylmaleic modification of the peptide melittin allows the peptide to complex with the cationic protein Histone H1 and then cleave to release and reactivate in the lowered pH encountered by the complex in the cellular endosomal compartment. This caused a significant increase in luciferase expression over either unmodified melittin peptide or melittin peptide modified with succinic anhydride which allows complexing with Histone H1 but will not cleave in lowered pH.

F) Transfection of 3T3 Cells with Dioleoyl 1,2-Diacyl-3-Trimethylammonium-Propane (DOTAP) and the membrane active peptide KL3 conjugated to dimethylmaleic modified Polyallylamine (DM-PAA-KL3) and poly-L-lysine or L-cystine-1,4-bis(3-aminopropyl)piperazine copolymer.

Three Complexes were Formed:
Complex I) To 250 µL 25 mM HEPES pH8.0 was added DOTAP 300 µg, Avanti Polar Lipids Inc)
Complex II) To 250 µL 25 mM HEPES pH8.0 was added DOTAP(300 µg, Avanti Polar Lipids Inc) followed by DM-PAA-KL$_3$ (10 µg) followed by poly-L-lysine (10 µg, Sigma).
Complex III) To 250 µL 25 mM HEPES pH8.0 was added DOTAP(300 µg, Avanti Polar Lipids Inc) followed by DM-PAA-KL$_3$ (10 µg) followed by L-cystine-1,4-bis(3-aminopropyl)piperazine copolymer (10 µg).

Liposomes for each complex were formed by 5 minutes of bath sonication then purified in batch by addition of 250 ul of DEAE sephadex A-25. DNA (25 ug, pCILuc)was then added to the supernatant containing the purified liposomes of each complex.

Transfections were carried out in 35 mm wells. At the time of transfection, 3T3 cells,at approximately 60% confluency, stored in complete growth media, DMEM with 10% fetal bovine serum (Sigma). 50 µL of complex was added to each well. After an incubation of 48 hours, the cells were harvested and the lysate was assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

Results:
Complex I: RLU=167
Complex II: RLU=60,092
Complex III: RLU=243,986

The 2,3-dimethylmaleic modification of DM-PAA-KL3 allows the polymer to complex with the cationic polymer L-cystine-1,4-bis(3-aminopropyl)piperazine copolymer and then cleavage of the 2,3-dimethylmaleamic group to release and reactivate in the disulfide reducing environment encountered by the complex in the cell. This caused a significant increase in luciferase expression over either DOTAP complexes alone or DM-PAA-KL3 complexed with poly-L-lysine that will not cleave in the reducing environment encountered by the complex in the cell.

G) Transfection of3T3 Cells with Complexes of pCI Luc pDNA/Cationic Polymers Caged with Compounds Containing Acid Labile Moieties.

Several Complexes were Formed:
Complex I: To a solution of pDNA (pCI Luc, 20 µg) in H$_2$O (400 µL) was added LT-1® (60 µg, Mirus Corporation).
Complex II: To a solution of pDNA (pCI Luc, 20 µg) in H$_2$O (400 µL) was added PLL (36 µg in 3.6 µL H$_2$O, 32,000 MW, Sigma Chemical Company).
Complex III: To a solution of pDNA (pCI Luc, 20 µg) in H$_2$O (400 µL) was added PLL (36 µg in 3.6 µL H$_2$O, 32,000 MW, Sigma Chemical Company) followed by DTBP (60 µg in 6 µL H$_2$O, Pierce Chemical Company).
Complex IV: To a solution of pDNA (pCI Luc, 20 µg) in H$_2$O (400 µL) was added PLL (36 µg in 3.6 µL H$_2$O, 32,000 MW, Sigma Chemical Company) followed by DTBP (60 µg in 6 µL H$_2$O, Pierce Chemical Company) followed by N,N'-dioleoyl-1,4-bis(3-aminopropyl)piperazine (10 µg, 2 µg/µL in EtOH).
Complex V: To a solution of pDNA (pCI Luc, 20 µg) in H$_2$O (400 µL) was added PLL (36 µg in 3.6 µL H$_2$O, 32,000 MW, Sigma Chemical Company) followed by MC211 (87 µg in 8.7 µL dimethylformamide).
Complex VI: To a solution of pDNA (pCI Luc, 20 µg) in H$_2$O (400 µL) was added PLL (36 µg in 3.6 µL H$_2$O, 32,000 MW, Sigma Chemical Company) followed by MC211 (87 µg in 8.7 µL dimethylformamide) followed by N,N'-dioleoyl-1,4-bis(3-aminopropyl)piperazine (10 µg, 2 µg/µL in EtOH).
Complex VII: To a solution of pDNA (pCI Luc, 20 µg) in H$_2$O (400 µL) was added Histone H1 (120 µg in 12 µL H$_2$O, Sigma Chemical Company).
Complex VIII: To a solution of pDNA (pCI Luc, 20 µg) in H$_2$O (400 µL) was added Histone H1 (120 µg in 12 µL H$_2$O, Sigma Chemical Company) followed by DTBP (100 µg in 10 µL H$_2$O, Pierce Chemical Company).
Complex IX: To a solution of pDNA (pCI Luc, 20 µg) in H$_2$O (400 µL) was added Histone H1 (120 µg in 12 µL H$_2$O, Sigma Chemical Company) followed by DTBP (100 µg in 10 µL H$_2$O, Pierce Chemical Company) followed by N,N'-dioleoyl-1,4-bis(3-aminopropyl)piperazine (10 µg, 2 µg/µL in EtOH).
Complex X: To a solution of pDNA (pCI Luc, 20 µg) in H$_2$O (400 µL) was added Histone H1 (120 µg in 12 µL H$_2$O, Sigma Chemical Company) followed by MC211 (145 µg in 14.5 µL dimethylformamide).
Complex XI: To a solution of pDNA (pCI Luc, 20 µg) in H$_2$O (400 µL) was added Histone H1 (120 µg in 12 µL H$_2$O, Sigma Chemical Company) followed by MC211 (145 µg in 14.5 µL dimethylformamide) followed by N,N'-dioleoyl-1,4-bis(3-aminopropyl)piperazine (10 µg, 2 µg/µL in EtOH).

Transfections were carried out in 35 mm wells. At the time of transfection, 3T3 cells, at approximately 50% confluency, were washed once with PBS (phosphate buffered saline), and subsequently stored in serum-free media (2.0 mL, Opti-MEM, Gibco-BRL). 100 µL of complex was added to each well. After a 3.25 h incubation period at 37° C., the media containing the complexes was aspirated from the cells, and replaced with complete growth media, DMEM with 10% fetal bovine serum (Sigma). After an additional incubation of 48 hours, the cells were harvested and the lysate was assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| Results: | |
|---|---|
| Complex I: | 2,467,529 RLU |
| Complex II: | 10,748 RLU |
| Complex III: | 377 RLU |
| Complex IV: | 273 RLU |
| Complex V: | 7,174 RLU |
| Complex VI: | 71,338 RLU |
| Complex VII: | 162,166 RLU |
| Complex VIII: | 1,336 RLU |
| Complex IX: | 162,166 RLU |
| Complex X: | 51,003 RLU |
| Complex XI: | 3,949,177 RLU |

The transfection results indicate that caging cationic pDNA complexes (PLL or Histone H1) with DTBP reduce the amount of expressed luciferine. Caging of the cationic pDNA complexes with MC211 results in an increased amount of expressed luciferine relative to the DTBP examples.

In Vivo Transfections

H) Mouse Tail Vein Injections of Complexes of pDNA (pCI Luc)/Polymer Containing Acid Labile Moieties:

H1) Mouse Tail Vein Injections of Complexes of pDNA (pCI Luc)/1,4-Bis(3-aminopropyl)piperazine Glutaric Dialdehyde Copolymer (MC 140).

Three Complexes were Prepared as Follows:
Complex I: pDNA (pCI Luc, 50 µg) in 12.5 mL Ringers.
Complex II: pDNA (pCI Luc, 50 µg) was mixed with 1,4-bis(3-aminopropyl)piperazine glutaric dialdehyde copolymer (50 µg) in 1.25 mL HEPES 25 mM, pH 8. This solution was then added to 11.25 mL Ringers.
Complex III: pDNA (pCI Luc, 50 µg) was mixed with poly-L-lysine (94.5 µg, MW 42,000, Sigma Chemical Company) in 12.5 mL Ringers.

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used.

| Results: 2.5 mL injections | |
|---|---|
| Complex I: | 3,692,000 RLU |
| Complex II: | 1,047,000 RLU |
| Complex III: | 4,379 RLU |

Results indicate an increased level of pCI Luc DNA expression in pDNA/1,4-bis(3-aminopropyl)piperazine glutaric dialdehyde copolymer complexes over pCI Luc DNA/poly-L-lysine complexes. These results also indicate that the pDNA is being released from the pDNA/1,4-Bis(3-aminopropyl)piperazine-glutaric dialdehyde copolymer complexes, and is accessible for transcription.

H2A) Mouse Tail Vein Injections of Complexes of pDNA (pCI Luc)/Imine Containing Copolymer's: By similar methods described above, several additional complexes were prepared from imine containing polymers at a 3:1 charge ratio of polycation to pDNA.

| Complex I: | pDNA (pCI Luc, 50 µg) |
|---|---|
| Complex II: | pDNA (pCI Luc, 50 µg)/MC229 |

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for n separate animals.

| Results: 2.5 mL injections | | |
|---|---|---|
| Complex I: | n = 3 | 3,430,000 RLU |
| Complex II: | n = 3 | 21,400,000 RLU |

The results indicate that the pDNA is being released from the pDNA/imine containing copolymer complexes, and is accessible for transcription.

H2B) Mouse Tail Vein Injections of Complexes of pDNA (pCI Luc)/Imine Containing Copolymer's. By similar methods described above, several additional complexes were prepared from imine containing polymers at a 3:1 charge ratio of polycation to pDNA.

| Complex I: | pDNA (pCI Luc, 50 µg) |
|---|---|
| Complex II: | pDNA (pCI Luc, 50 µg)/MC140-2 |
| Complex III: | pDNA (pCI Luc, 50 µg)/MC312 |

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for n separate animals.

| Results: 2.5 mL injections | | |
|---|---|---|
| Complex I: | n = 1 | 9,460,000 RLU |
| Complex II: | n = 3 | 7,730,000 RLU |
| Complex III: | n = 3 | 16,300,000 RLU |

The results indicate that the pDNA is being released from the pDNA/imine containing copolymer complexes, and is accessible for transcription.

H3A) Mouse Tail Vein Injections of Complexes of pDNA (pCI Luc)/Ketal Containing Copolymers. By similar methods described above, several complexes were prepared at a 3:1 charge ratio of polycation to pDNA:

| | |
|---|---|
| Complex I: | pDNA (pCI Luc, 50 µg) |
| Complex II: | pDNA (pCI Luc, 50 µg)/PLL-DTBP(Pierce Chemical Co., 50%) |
| Complex III: | pDNA (pCI Luc, 50 µg)/PLL-MC211(50%) |
| Complex IV: | pDNA (pCI Luc, 50 µg)/MC228 |
| Complex V: | pDNA (pCI Luc, 50 µg)/MC208 |

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for n separate animals.

| Results: 2.5 mL injections | | |
|---|---|---|
| Complex I: | n = 3 | 2,440,000 RLU |
| Complex II: | n = 3 | 110,000 RLU |
| Complex III: | n = 3 | 292,000 RLU |
| Complex IV: | n = 3 | 119,000 RLU |
| Complex V: | n = 3 | 3,590,000 RLU |

H3B) Mouse Tail Vein Injections of Complexes of pDNA (pCI Luc)/Ketal Containing Copolymers. By similar methods described above, several complexes were prepared at a 3:1 charge ratio of polycation to pDNA:

| | |
|---|---|
| Complex I: | pDNA (pCI Luc, 50 µg) |
| Complex II: | pDNA (pCI Luc, 50 µg)/PLL-MC225(50%) |
| Complex III: | pDNA (pCI Luc, 50 µg)/MC217 |
| Complex IV: | pDNA (pCI Luc, 50 µg)/MC218 |

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for n separate animals.

| Results: 2.5 mL injections | | |
|---|---|---|
| Complex I: | n = 3 | 5,940,000 RLU |
| Complex II: | n = 3 | 611,000 RLU |
| Complex III: | n = 3 | 5,220,000 RLU |
| Complex IV: | n = 3 | 7,570,000 RLU |

H3C) Mouse Tail Vein Injections of Complexes of pDNA (pCI Luc)/Ketal Containing Copolymers. By similar methods described above, several complexes were prepared at a 3:1 charge ratio of polycation to pDNA:

| | |
|---|---|
| Complex I: | pDNA (pCI Luc, 50 µg) |
| Complex II: | pDNA (pCI Luc, 50 µg)/MC208 |
| Complex III: | pDNA (pCI Luc, 50 µg)/MC301 |

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for n separate animals.

| Results: 2.5 mL injections | | |
|---|---|---|
| Complex I: | n = 3 | 3,430,000 RLU |
| Complex II: | n = 2 | 9,110,000 RLU |
| Complex III: | n = 3 | 8,570,000 RLU |

Results indicate an increased level of pCI Luc DNA expression in Complex III and Complex VII relative to Complex II indicating that when the acid labile homobifunctional amine reactive system (MC211, MC225) is used, more pDNA is accessible for transcription relative to the non-labile homobifunctional amine reactive system (DTBP). These results also indicate that the pDNA is being released from the pDNA/ketal containing copolymer complexes, and is accessible for transcription.

H4) Mouse Tail Vein Injections of Complexes of pDNA (pCI Luc)/Silicon Containing Polymers. By similar methods described above, several complexes were prepared at a 3:1 charge ratio of polycation to pDNA:

| | |
|---|---|
| Complex I: | pDNA (pCI Luc, 50 µg) |
| Complex II: | pDNA (pCI Luc, 50 µg)/MC221 |
| Complex III: | pDNA (pCI Luc, 50 µg)/MC222 |
| Complex IV: | pDNA (pCI Luc, 50 µg)/MC223 |
| Complex V: | pDNA (pCI Luc, 50 µg)/MC358 |
| Complex VI: | pDNA (pCI Luc, 50 µg)/MC358 recharged with SPLL (MC359) |
| Complex VII: | pDNA (pCI Luc, 50 µg)/MC360 |
| Complex VIII: | pDNA (pCI Luc, 50 µg)/Poly-L-Arginine/-L-Serine(3:1) |
| Complex IX: | pDNA (pCI Luc, 50 µg)/MC366 |
| Complex X: | pDNA (pCI Luc, 50 µg)/MC367 |
| Complex XI: | pDNA (pCI Luc, 50 µg)/MC369 |
| Complex XII: | pDNA (pCI Luc, 50 µg)/MC370 |

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for n separate animals.

| Results: 2.5 mL injections | | |
|---|---|---|
| Complex I: | n = 14 | 14,564,000 RLU |
| Complex II: | n = 14 | 14,264,000 RLU |
| Complex III: | n = 9 | 13,449,000 RLU |
| Complex IV: | n = 3 | 6,927,000 RLU |
| Complex V: | n = 3 | 10,049,000 RLU |
| Complex VI: | n = 3 | 13,879,000 RLU |
| Complex VII: | n = 3 | 10,599,000 RLU |
| Complex VIII: | n = 3 | 638,000 RLU |
| Complex IX: | n = 3 | 12,597,000 RLU |
| Complex X: | n = 3 | 13,093,000 RLU |
| Complex XI: | n = 3 | 25,129,000 RLU |
| Complex XII: | n = 3 | 15,857,000 RLU |

The results indicate that the pDNA is being released from the pDNA/Silicon containing polycation complexes, and is accessible for transcription. Additionally, the results indicate that complex VIII (does not contain the silicon) is much less effective in the assay than is complex V. Additionally, the results indicate that upon the addition of a third layer, a polyanion (complex VI), the complex containing the silicon polymer allows for pDNA transcription.

G) Mouse Intramuscular Injections of Complexes of pDNA (pCI Luc)/Polymer Containing Acid Labile Moiety(s): Complexes were prepared as follows:

| Complex I: | pDNA. pDNA (pCI Luc, 60 µg, 27 µl) was added to 0.9% saline (1173 µL). |
|---|---|
| Complex II: | pDNA/MC208 (1:0.5). To a solution of pDNA (pCI Luc, 60 µg, 27 µL) in 0.9% saline (1173 µL) was added MC208 (0.19 µL, in dimethylformamide). |
| Complex III: | pDNA/MC208 (1:3). To a solution of pDNA (pCI Luc, 60 µg) in 0.9% saline (1161 µL) was added MC208 (12 µL, in dimethylformamide). |
| Complex IV: | pDNA/MC301 (1:0.5). To a solution of pDNA (pCI Luc, 60 µg, 27 µL) in 0.9% saline (1173 µL) was added MC301 (0.15 µL, in dimethylformamide). |
| Complex V: | pDNA/MC301 (1:3). To a solution of pDNA (pCI Luc, 60 µg, 27 µL) in 0.9% saline (1172 µL) was added MC301 (0.88 µL, in dimethylformamide). |
| Complex VI: | pDNA/MC229 (1:0.5). To a solution of pDNA (pCI Luc, 60 µg, 27 µL) in 0.9% saline (1173 µL) was added MC229 (0.09 µL, in dimethylformamide). |
| Complex VII: | pDNA/MC229 (1:3). To a solution of pDNA (pCI Luc, 60 µg, 27 µL) in 0.9% saline (1172 µL) was added MC229 (0.59 µL, in dimethylformamide). |
| Complex VIII: | pDNA/MC140 (1:0.5). To a solution of pDNA (pCI Luc, 60 µg, 27 µL) in 0.9% saline (1173 µL) was added MC140 (0.08 µL, in dimethylformamide). |
| Complex IX: | pDNA/MC140 (1:3). To a solution of pDNA (pCI Luc, 60 µg, 27 µL) in 0.9% saline (1173 µL) was added MC140 (0.48 µL, in dimethylformamide). |
| Complex X: | pDNA/MC312 (1:0.5). To a solution of pDNA (pCI Luc, 60 µg, 27 µL) in 0.9% saline (1173 µL) was added MC312 (0.08 µL, in dimethylformamide). |
| Complex XI: | pDNA/MC312 (1:3). To a solution of pDNA (pCI Luc, 60 µg, 27 µL) in 0.9% saline (1173 µL) was added MC312 (0.50 µL, in dimethylformamide). |
| Complex XII: | pDNA/MC217 (1:0.5). To a solution of pDNA (pCI Luc, 60 µg, 27 µL) in 0.9% saline (1173 µL) was added MC217 (0.11 µL, in dimethylformamide). |
| Complex XIII: | pDNA/MC217 (1:3). To a solution of pDNA (pCI Luc, 60 µg, 27 µL) in 0.9% saline (1172 µL) was added MC217 (0.69 µL, in dimethylformamide). |
| Complex XIV: | pDNA/MC221 (1:3). To a solution of pDNA (pCI Luc, 40 µg, 18 µL) in 0.9% saline (781 µL) was added MC221 (1.1 µL, in H₂O). |
| Complex XV: | pDNA/MC222 (1:3). To a solution of pDNA (pCI Luc, 40 µg, 18 µL) in 0.9% saline (782 µL) was added MC222 (0.40 µL, in H₂O). |
| Complex XVI: | pDNA. pDNA (pCI Luc, 100 µg, 45 µL) was added to 0.9% saline (1955 µL). |
| Complex XVII: | pDNA/PLL (1:3). To a solution of pDNA (pCI Luc, 100 µg, 45 µL) in 0.9% saline (1943 µL) was added PLL (32,000 MW, Sigma Chemical Company, 12 µL, in H₂O). |
| Complex XVIII: | pDNA/PEI (1:3). To a solution of pDNA (pCI Luc, 100 µg, 45 µL) in 0.9% saline (1,945 µL) was added PEI (25,000 MW, Sigma Chemical Company, 10 µL (10 mg/mL), in H₂O). |
| Complex XIX: | pDNA/HistoneH1 (1:3). To a solution of pDNA (pCI Luc, 100 µg, 45 µL) in 0.9% saline (1.889 µL) was added Histone H1 (Sigma Chemical Company, 66 µL (10 mg/mL), in H₂O). |

Direct muscle injections of 200 µL of the complex were preformed as previously described (See Budker, V., Zhang, G., Danko, I., Williams, P., and Wolff, J., "The Efficient Expression Of Intravascularly Delivered DNA In Rat Muscle," Gene Therapy 5, 272–6(1998); Wolff, J. A., Malone, R. W., Williams, P., Chong, W., Acsadi, G., Jani, A. and Felgner, P. L. Direct gene transfer into mouse muscle in vivo. Science, 1465–1468, 1990. Seven days post injection, the animals were sacrificed, and the muscle harvested. Samples were homogenized in lux buffer (1 mL), and centrifuged for 15 minutes at 4000 RPM. Luciferase expression was determined as previously reported. Results reported are for the average expression for the quadracep muscle (left and right quadracep muscle/2) per number of animals (n).

| Results: | | |
|---|---|---|
| Complex I: | n = 3 | 473,148 RLU |
| Complex II: | n = 3 | 328,054 RLU |
| Complex III: | n = 3 | 104,348 RLU |
| Complex IV: | n = 3 | 228,582 RLU |
| Complex V: | n = 3 | 259,007 RLU |
| Complex VI: | n = 3 | 989,905 RLU |
| Complex VII: | n = 3 | 286,118 RLU |
| Complex VIII: | n = 3 | 433,177 RLU |
| Complex IX: | n = 3 | 46,727 RLU |
| Complex X: | n = 3 | 365,440 RLU |
| Complex XI: | n = 3 | 454 RLU |
| Complex XII: | n = 3 | 1,386,208 RLU |
| Complex XIII: | n = 3 | 295 RLU |
| Complex XIV: | n = 2 | 352,639 RLU |
| Complex XV: | n = 2 | 459,695 RLU |
| Complex XVI: | n = 10 | 1,281,401 RLU |
| Complex XVII: | n = 10 | 2,789 RLU |
| Complex XVIII: | n = 10 | 340 RLU |
| Complex XIX: | n = 10 | 357 RLU |

The complexes prepared from pCI Luc DNA and polymers containing acid labile moities are effective in direct muscle injections. The luciferase expression indicates that the pDNA is being released from the complex and is accessible for transcription.

Example 3

Synthesis of Peptides and Polyions

A) Peptide synthesis. Peptide synthesis were performed using standard solid phase peptide techniques using FMOC chemistry. N-terminal acryloyl 6-aminohexanoyl-SEQ ID NO: 10-CO$_2$ (AcKL$_3$) was synthesized according to published procedure (O'Brien-Simpson, N. M., Ede, N. J., Brown, L. E., Swan, J., Jackson, D. C *J. Am. Chem. Soc.* 1997, 119, 1183).

B) Coupling KL$_3$ to poly(allylamine). To a solution of poly(allylamine) (2 mg) in water (0.2 mL) was added KL3 (0.2 mg, 2.5 eq) and 1-(3-dimethylaminopropyl)-3-ethylcarbodiimide hydrochloride (1 mg, 150 eq). The reaction was allowed to react for 16 h and then the mixture was placed into dialysis tubing and dialyzed against 3×1 L for 48 h. The solution was then concentrated by lyophilization to 0.2 mL.

C) Synthesis of L-cystine-1,4-bis(3-aminopropyl)piperazine copolymer. To a solution of N,N'-Bis(t-BOC)-L-cystine (85 mg, 0.15 mmol) in ethyl acetate (20 mL) was added N,N'-dicyclohexylcarbodiimide (108 mg, 0.5 mmol) and N-hydroxysuccinimide (60 mg, 0.5 mmol). After 2 hr, the solution was filtered through a cotton plug and 1,4-bis(3-aminopropyl)piperazine (54 mL, 0.25 mmol) was added. The reaction was allowed to stir at room temperature for 16 h. The ethyl acetate was then removed by rotary evaporation and the resulting solid was dissolved in trifluoroacetic acid (9.5 mL), water (0.5 mL) and triisopropylsilane (0.5 mL). After 2 h, the trifluoroacetic acid was removed by rotary evaporation and the aqueous solution was dialyzed in a 15,000 MW cutoff tubing against water (2×2 l) for 24 h. The solution was then removed from dialysis tubing, filtered through 5 μM nylon syringe filter and then dried by lyophilization to yield 30 mg of polymer.

D) Synthesis of 5,5'-Dithiobis(2-nitrobenzoic acid)-1,4-Bis(3-aminopropyl)piperazine Copolymer. 1,4-Bis(3-aminopropyl)piperazine (10 mL, 0.050 mmol, Aldrich Chemical Company) was taken up in 1.0 mL methanol and HCl (2 mL, 1 M in Et2O, Aldrich Chemical Company) was added. Et2O was added and the resulting HCl salt was collected by filtration. The salt was taken up in 1 mL DMF and 5,5'-dithiobis[succinimidyl(2-nitrobenzoate)] (30 mg, 0.050 mmol) was added. The resulting solution was heated to 80° C. and diisopropylethylamine (35 mL, 0.20 mmol, Aldrich Chemical Company) was added by drops. After 16 hr. the solution was cooled, diluted with 3 mL H2O, and dialyzed in 12,000–14,000 MW cutoff tubing against water (2×2 L) for 24 h. The solution was then removed from dialysis tubing and dried by lyophilization to yield 23 mg (82%) of 5,5'-dithiobis(2-nitrobenzoic acid)-1,4-bis(3-aminopropyl)piperazine copolymer.

E) Synthesis of polypropylacrylic acid. To a solution of diethylpropylmalonate (2 g, 10 mmol) in 50 mL ethanol was added potassium hydroxide (0.55 g, 1 eq) and the mixture was stirred at room temperature for 16 hours. The ethanol was then removed by rotary evaporation. The reaction mixture was partitioned between 50 mL ethyl acetate and 50 mL of water. The aqueous solution was isolated, and acidified with hydrochloric acid. The solution was again partitioned between ethyl acetate and water. The ethyl acetate layer was isolated, dried with sodium sulfate, and concentrated to yield a clear oil. To this oil was added 20 mL of pyridine, paraformaldehyde (0.3 g, 10 mmol), and 1 mL piperidine. The mixture was refluxed at 130° C. until the evolution of gas was observed, ca. 2 hours. The ester product was then dissolved into 100 mL ethyl ether, which was washed with 100 mL 1M hydrochloric acid, 100 mL water, and 100 mL saturated sodium bicarbonate. The ether layer was isolated, dried with magnesium sulfate, and concentrated by rotary evaporation to yield a yellow oil. The ester was then hydrolyzed by dissolving in 50 mL ethanol with addition of potassium hydroxide (0.55 gm, 10 mmol). After 16 hours, the reaction mixture was acidified by the addition of hydrochloric acid. The propylacrylic acid was purified by vacuum distillation (0.9 g, 80% yield), boiling point of product is 60° C. at 1 torr. The propylacrylic acid was polymerized by addition of 1 mole percent of azobisisobutyonitrile and heating to 60° C. for 16 hours. The polypropylacrylic acid was isolated by precipitation with ethyl ether.

F) Synthesis of poly N-terminal acryloyl 6-aminohexanoyl-SEQ ID NO: 10-CO$_2$ (pAcKL$_3$). A solution of AcKL3 (20 mg, 7.7 μmol) in 0.5 mL of 6 M guanidinium hydrochloride, 2 mM EDTA, and 0.5 M Tris pH 8.3 was degassed by placing under a 2 torr vacuum for 5 minutes. Polymerization of the acrylamide was initiated by the addition of ammonium persulfate (35 μg, 0.02 eq.) and N,N,N,N-tetramethylethylenediamine (1 μL). The polymerization was allowed to proceed overnight. The solution was then placed into dialysis tubing (12,000 molecular weight cutoff) and dialyzed against 3×2 L over 48 hours. The amount of polymerized peptide (6 mg, 30% yield) was determined by measuring the absorbance of the tryptophan residue at 280 nm, using an extinction coefficient of 5690 cm$^{-1}$M$^{-1}$ (Gill, S. C. and von Hippel, P. H. Analytical Biochemistry (1989) 182, 319–326)

Example 4

Kinetic Analysis

A) Kinetics of conversion of dimethyl maleamic modified poly-L-lysine to poly-L-lysine. Dimethyl maleamic modified poly-L-lysine (10 mg/mL) was incubated in 10 mM sodium acetate buffer pH 5. At various times, aliquots (10 μg) were removed and added to 0.5 mL of 100 mM borax solution containing 0.4 mM trinitrobenzenesulfonate. A half an hour later, the absorbance of the solution at 420 nm was measured. To determine the concentration of amines at each time point, the extinction coefficient was determine for the product of trinitrobenzenesulfonate and poly-L-lysine. Using this extinction coefficient we were able to calculate the amount of amines and maleamic groups at each time point. A plot of ln ($A_t/A_0$) as a function of time was a straight line whose slope is the negative of the rate constant for the conversion of maleamic acid to amine and anhydride, where $A_t$ is the concentration of maleamic acid at a time t and $A_0$ is the initial concentration of maleamic acid. For two separate experiments we calculated rate constants of 0.066 sec$^{-1}$ and 0.157 sec$^{-1}$ which correspond to half lives of roughly 10 and 4 minutes respectively.

B) Kinetics of conversion of dimethylmaleamic modified KL$_3$ (DM-KL$_3$) to KL$_3$. Dimethyl maleamic modified KL$_3$ (0.1 mg/mL) was incubated in 40 mM sodium acetate buffer pH 5 and 1 mM cetyltrimetylammonium bromide. At various times, aliquots (10 μg) were removed and added to 0.05 mL of 1 M borax solution containing 4 mM trinitrobenzenesulfonate. A half an hour later, the absorbance of the solution at 420 nm was measured. To determine the concentration of amines at each time point, the extinction coefficient was determine for the product of trinitrobenzenesulfonate and poly-L-lysine. Using this extinction coefficient we were able to calculate the amount of amines and maleamic groups at each time point. A plot of ln ($A_t/A_0$) as a function of time was a straight line whose slope is the negative of the rate constant for the conversion of maleamic acid to amine and anhydride, where $A_t$ is the concentration of maleamic acid at a time t and $A_0$ is the intial concentration of maleamic acid. We calculated a rate constant of 0.087 sec$^{-1}$ that corresponds to a half-life of roughly 8 minutes.

C) Kinetics of hydrolysis of glycolic acid ethoxylate(4 units) 4-tert-buty-1,4-cyclohexadiene. Glycolic acid ethoxylate(4 units) 4-tert-buty-1,4-cyclohexadiene (1 mg) was dissolved in placed into 1 mL of 15 mM sodium acetate pH 5 buffer. The absorbance of the solution at 225 nm, which is the wavelength at which enol ethers absorb (Kresge, A. J.; Sagatys, D. S.; Chen, H. L. J. Am. Chem. Soc. 1977, 99, 7228) was measured over time. A fit of the decrease of absorbance as a function of time by an exponential decay function had a rate constant of 0.0159 min$^{-1}$, which corresponds to a half-life of 40 minutes.

D) Kinetics of hydrolysis of poly(oxy-1-para-aceticphenoxymethylethylene-co-oxy-1-methylethylene). Poly(oxy-1-para-aceticphenoxymethylethylene-co-oxy-1-methylethylene) (0.16 mg/mL) was placed into 1 mL of 5 mM sodium acetate buffer pH 5. The absorbance of the solution at 225 nm was measured as a function of time. The amount of time it took for the absorbance to decrease half of maximum was 37 minutes, i.e. the half-life of hydrolysis is 37 minutes.

E) Particle Formation of poly(oxy-1-para-aceticphenoxymethylethylene-co-oxy-1-methylethylene) as a Function of Acidification and Time. To a solution (0.5 mL) of 5 mM HEPES pH 8 was added poly(oxy-1-para-aceticphenoxymethylethylene-co-oxy-1-methylethylene) (54 µg/mL) which had been incubated for various times in the presence of 1 mM acetic acid (pH4–5), followed by the addition of polyallylamine. The intensity of the scattered light and the size of the particle were measured (using a Brookhaven ZetaPlus Particle Sizer) as a function of the amount of time the polymer was incubated under acidic conditions.

| Time at pH 4–5 (minutes) | Size (nm) | Scattered light intensity (kilocounts per second) |
|---|---|---|
| 0 | 231 | 390 |
| 1 | 195 | 474 |
| 2 | 208 | 460 |
| 5 | 224 | 450 |
| 15 | 124 | 92 |
| 39 | 132 | 250 |

F) Kinetics of Cleavage of Ketal. Synthesis of Microspheres Containing Acid Labile Ketal Moieties:

F1) Esterification of Carboxylic Acid Modified Microspheres with Di-(2-methyl-4-hydroxymethyl-1,3-dioxolane)-1,4-benzene. To a suspension of carboxylic acid modified microspheres (1000 µL, 2% solids, Molecular Probes) in H$_2$O (500 µL) was added 1-(3-dimethylaminopropyl)-3-ethylcarbodiimide hydrochloride (7.0 mg, 36 µmol, Aldrich Chemical Company), followed by di-(2-methyl-4-hydroxymethyl-1,3-dioxolane)-1,4-benzene (23 mg, 73 µmol), and the suspension was stirred at room temperature. After 16 hrs, the microspheres were removed by centrifugation. The supernatant was removed and the pellet was resuspended in 1.5 mL H$_2$O to wash. The microspheres were washed an additional 2×1.5 mL H$_2$O and suspended in 1 mL H$_2$O.

F2) Aldehyde Derivatization of Esterified Carboxylic Acid Modified Microspheres with Di-(2-methyl-4-hydroxymethyl-1,3-dioxolane)-1,4-benzene. To a solution of succinic semialdehyde (3.7 mg, 36 µmol, Aldrich Chemical Company) in H$_2$O was added 1-(3-dimethylaminopropyl)-3-ethylcarbodiimide hydrochloride (8.7 mg, 46 µmol, Aldrich Chemical Company) followed by N-hydroxysuccinimide (5.3 mg, 46 µmol, Aldrich Chemical Company). The solution was stirred for 20 min at which time carboxylic acid modified microspheres esterified with di-(2-methyl-4-hydroxymethyl-1,3-dioxolane)-1,4-benzene (500 µL) were added. After 16 hrs, the microspheres were removed by centrifugation. The supernatant was removed and the pellet was resuspended in 1 mL H$_2$O to wash. The microspheres were washed an additional 2×1 mL H$_2$O and suspended in 1 mL H$_2$O. The aldehyde content of the microspheres was determined on a 50 µL sample of the suspension with 2,4-dinitrophenylhydrazine and NaBH$_3$CN. The absorbance measured at 349 nm and fitted against a standard curve indicated 18 µmol of aldehyde present in the reaction sample.

Attachment of Membrane Active Peptide to Acid Labile Moieties and Lability Studies of these Systems:

F3) Attachment of a Peptide (Melittin) to the Aldehyde Derived from Carboxylic Acid Modified Microspheres Esterified with Di-(2-methyl-4-hydroxymethyl-1,3-dioxolane)-1,4-benzene. To 100 µL of the aldehyde derivatized microshpere suspension was added 400 µL H$_2$O and melittin (1 mg, 0.4 µmol, Mirus Corporation). After 12 hrs, NaBH$_3$CN (0.6 mg, 9 µmol, Aldrich Chemical Company) was added. After 1 hr, the suspension was centrifugated to pellatize the microspheres. The supernatant was removed and the pellet was resuspended in 1 mL H$_2$O to wash. The microspheres were washed an additional 3×1 mL H$_2$O and suspended in 1 mL H$_2$O. The last wash indicated the presence of active peptide based on red blood cell lysis activity. The sample was washed 1×25 mM HEPES, and 1×H$_2$O. The final wash was free of peptide based on red blood cell lysis assay.

F4) Blood Lysis Experiment on Melittin Conjugated to Microspheres via the Di-(2-methyl-4-hydroxymethyl-1,3-dioxolane)-1,4-benzene. The microspheres were taken up in H$_2$O (500 µL) and partitioned into five 100 µL samples. Four of the samples were diluted to 1000 µL with sodium phosphate buffer (100 mM) at pH 7.5, 6.0, 5.5, and 5.0. Samples were held at 37° C., spun down, and 150 µL aliquots taken at 30 min, 60 min, 90 min, and 16 hrs. A portion of each sample (100 µL) was diluted with sodium phosphate buffer (400 µL, pH 7.5) and added to red blood cells (100 µL, pH 7.5). Red blood cell lysis was measured after 10 min by measuring the absorbance at 541 nm.

A control sample was also measured in which 100% of the red blood cells had been lysed with melittin alone.

| Sample | A$_{541}$ |
|---|---|
| Blood | 0.026 |
| 100% lysis | 1.881 |
| 30 min pH 7.5 | 0.026 |
| 30 min pH 6.0 | 0.326 |
| 30 min pH 5.5 | 0.609 |
| 30 min pH 5.0 | 0.659 |
| 60 min pH 7.5 | 0.027 |
| 60 min pH 6.0 | 0.212 |
| 60 min pH 5.5 | 0.526 |
| 60 min pH 5.0 | 0.730 |
| 90 min pH 7.5 | 0.036 |
| 90 min pH 6.0 | 0.390 |
| 90 min pH 5.5 | 0.640 |
| 90 min pH 5.0 | 0.892 |
| 16 hrs pH 7.5 | 0.065 |
| 16 hrs pH 6.0 | 0.354 |
| 16 hrs pH 5.5 | 0.796 |
| 16 hrs pH 5.0 | 1.163 |

The fifth 100 µL sample was further divided into 25 µL samples, three of which were diluted to 250 µL with sodium phosphate buffer (100 mM) at pH 7.5, 6.0, and 5.0. The samples were held at 37° C. for 30 min, spun down and the supernatant removed, and resuspended in 2.5 M NaCl solution (50 μL) and mixed. After 10 min the microspheres were spun down and the supernatant removed. The samples were added to red blood cells (500 μL, 100 mM) and the absorbance was measured at 541 nm.

| Sample | $A_{541}$ |
|---|---|
| Blood (NaCl wash) | 0.041 |
| pH 7.5 | 0.053 |
| pH 7.5 (NaCl wash) | 0.087 |
| pH 6.0 | 0.213 |
| pH 6.0 (NaCl wash) | 0.162 |
| pH 5.0 | 0.685 |
| pH 5.0 (NaCl wash) | 0.101 |

The results indicate that under acidic conditions, the modified peptide is released from the microsphere and is available to interact with the cell membrane as indicated by the red blood cell lysis. The results indicate that the modified peptide is not released at pH 7.5. Additionally, the lysis activity results indicate the release of modified peptide is rapid at all acidic pH levels tested (t<30 min) with slow continual release thereafter, and that more modified peptide is released at lower pH (larger red blood cell lysis). The results also indicate that more modified peptide is released upon washing the microsphere with a salt solution.

F5) Attachment of a Peptide (Melittin) to the Aldehyde Derived from Poly-Glutamic Acid Partially Esterified with Di-(2-methyl-4-hydroxymethyl-1,3-dioxolane)-1,4-benzene. To a solution of the aldehyde-poly-glutamic acid compound (1.0 mg, 7.7 μmol) in water (200 μL) was added melittin (4.0 mg, 1.4 μmol) and the reaction mixture was stirred at room temperature. After 12 hrs the reaction mixture was divided into two equal portions. One sample (100 μL) was dialyzed against 1% ethanol in water (2×1 L, 12,000–14,000 MWCO) and tested utilizing a theoretical yield of 1.7 mg. To the second portion (100 μL) was added sodium cyanoborohydride (1.0 mg, 16 μmol, Aldrich Chemical Company). The solution was stirred at room temperature for 1 hr and then dialyzed against water (2×1 L, 12,000–14,000 MWCO). The resulting material was utilized assuming a theoretical yield of 1.7 mg of conjugate.

Lability of Polymers Containing Acid Labile Moieties:

F6) Particle Sizing and Acid Lability of Poly-L-Lysine/Ketal Acid of Polyvinylphenyl Ketone and Glycerol Ketal Complexes. Particle sizing (Brookhaven Instruments Corporation, ZetaPlus Particle Sizer, I90, 532 nm) indicated an effective diameter of 172 nm (40 μg) for the ketal acid. Addition of acetic acid to a pH of 5 followed by particle sizing indicated a increase in particle size to 84000 nm. A poly-L-lysine/ketal acid (40 μg, 1:3 charge ratio) sample indicated a particle size of 142 nm. Addition of acetic acid (5 μL, 6 N) followed by mixing and particle sizing indicated an effective diameter of 1970 nm. This solution was heated at 40° C. Particle sizing (by a Brookhaven ZetaPlus Particle Sizer) indicated an effective diameter of 74000 nm and a decrease in particle counts.

Results: The particle sizer data indicates the loss of particles upon the addition of acetic acid to the mixture.

F7) Particle Sizing and Acid Lability of Poly-L-Lysine/Ketal from Polyvinyl Alcohol and 4-Acetylbutyric Acid Complexes. Particle sizing (Brookhaven Instruments Coporation, ZetaPlus Particle Sizer, I90, 532 nm) indicated an effective diameter of 280 nm (743 kcps) for poly-L-lysine/ketal from polyvinyl alcohol and 4-acetylbutyric acid complexes (1:3 charge ratio). A poly-L-lysine sample indicated no particle formation. Similarly, a ketal from polyvinyl alcohol and 4-acetylbutyric acid sample indicated no particle formation. Acetic acid was added to the poly-L-lysine/ketal from polyvinyl alcohol and 4-acetylbutyric acid complex to a pH of 4.5. Particle sizing (by a Brookhaven ZetaPlus Particle Sizer) indicated particles of 100 nm, but at a low count rate (9.2 kcps). Results: The particle size data indicates the loss of particles upon the addition of acetic acid to the mixture.

F8) Size Exclusion Chromatography and Acid Lability of MC228. MC208 (1.5 mg) was taken up in 50 mM HEPES (0.3 mL, pH 8.5) and passed through a Sephadex G50 column (8 cm column, 50 mM HEPES (pH 8.5) eluent) and 0.5 mL fractions were collected. The absorbance of the fractions was determined at 300 nm. Two additional samples (1.5 mg) were prepared in 50 mM Citrate buffer at pH 2 and pH 5 (0.3 mL) and allowed to sit a room temperature for 45 min prior to running on the Sephadex G50 column (8 cm column, 50 mM HEPES (pH 8.5) eluent). The absorbance of the fractions was determined at 300 nm.

| Fraction number | pH 8.5 | pH 5 | pH 2 |
|---|---|---|---|
| 1 | 0.018 | 0.040 | 0.022 |
| 2 | 0.024 | 0.019 | 0.013 |
| 3 | 0.019 | 0.015 | 0.008 |
| 4 | 0.028 | 0.118 | 0.024 |
| 5 | 0.287 | 0.527 | 0.293 |
| 6 | 1.091 | 0.693 | 0.604 |
| 7 | 0.976 | 0.818 | 0.715 |
| 8 | 0.888 | 1.071 | 0.895 |
| 9 | 0.907 | 1.178 | 1.082 |
| 10 | 0.944 | 1.289 | 1.298 |
| 11 | 0.972 | 1.296 | 1.423 |
| 12 | 0.941 | 1.212 | 1.326 |
| 13 | 0.913 | 0.924 | 1.140 |
| 14 | 0.764 | 0.640 | 1.012 |
| 15 | 0.589 | 0.457 | 0.841 |
| 16 | 0.415 | 0.264 | 0.655 |

Results: The column demonstrates that upon incubating the sample under acidic conditions, the molecular weight of the polymer is decreased indicating the polymer is labile under acidic conditions.

F9) Acid Lability of MC208. A sample of MC208 in dimethylformamide (20 μL) was divided into four equal samples. To each sample was added citrate buffer (100 μL, pH 4) and the resulting samples (final pH of 5) were incubated at 37° C. for 2, 4, 8, and 24 hrs. The samples were then analyzed by thin layer chromatography against a sample not exposed to acidic conditions.

The results indicated increasing amounts of higher Rf material with increasing time, indicated degradation of the polymer.

F10) Particle Sizing and Acid Lability of pDNA (pCI Luc)/MC208 Complexes. Particle sizing (Brookhaven Instruments Coporation, ZetaPlus Particle Sizer, I90, 532 nm) indicated an effective diameter of 293 nm (687 kcps) for pDNA (25 μg pDNA)/di-(2-methyl-4-hydroxymethyl(succinic semialdehyde ester)-1,3-dioxolane)-1,4-benzene: 1,4-bis(3-aminopropyl)-piperazine copolymer complexes (1:3 charge ratio). HCl was added to the complex to approximately pH 5 and the particle size was measured. The reading indicated particles with an effective diameter of 11349 nm (120 kcps).

Results: The particle size data indicates MC208 compacts pDNA into small particles. The results also indicate the loss of particles upon the addition of HCl to the mixture by flocculation.

G) Kinetics of Cleavage of Imine: Particle Sizing and Acid Lability of pDNA (pCI Luc)/1,4-Bis(3-aminopropyl) piperazine Glutaric Dialdehyde Copolymer Complexes. To 50 μg pDNA in 2 mL HEPES (25 mM, pH 7.8) was added 135 μg 1,4-bis(3-aminopropyl)piperazine glutaric dialdehyde copolymer. Particle sizing (Brookhaven Instruments Coporation, ZetaPlus Particle Sizer, I90, 532 nm) indicated an effective diameter of 110 nm for the complex. A 50 μg pDNA in 2 mL HEPES (25 mM, pH 7.8) sample indicated no particle formation. Similarly, a 135 μg 1,4-bis(3-aminopropyl)piperazine glutaric dialdehyde copolymer in 2 mL HEPES (25 mM, pH 7.8) sample indicated no particle formation. Acetic acid was added to the pDNA (pCI Luc)/ 1,4-bis(3-aminopropyl)piperazine glutaric dialdehyde copolymer complex to a pH of 4.5. Particle sizing indicated particles of 2888 nm, and aggregation was observed.

Results: 1,4-Bis(3-aminopropyl)piperazine-glutaric dialdehyde copolymer condenses pDNA, forming small particles. Upon acidification, the particle size increases, and aggregation occurs, indicating cleavage of the polymeric imine.

Example 5

Hemolysis Assay

A) Lysis of Erythrocytes by the peptides Melittin and $KL_3$ and their dimethylmaleamic acid derivatives as a function of pH. The membrane-disruptive activity of the peptide melittin and subsequent blocking of activity by anionic polymers was measured using a red blood cell (RBC) hemolysis assay. RBCs were harvested by centrifuging whole blood for 4 min. They were washed three times with 100 mM dibasic sodium phosphate at the desired pH, and resuspended in the same buffer to yield the initial volume. They were diluted 10 times in the same buffer, and 200 uL of this suspension was used for each tube. This yields 10^8 RBCs per tube. Each tube contained 800 uL of buffer, 200 uL of the RBC suspension, and the peptide with or without polymer. Each sample was then repeated to verify reproducibility. The tubes were incubated for 30 minutes in a 37° C. water bath. They were spun for 5 min at full speed in the microcentifuge. Lysis was determined by measuring the absorbance of the supernatant at 541 nm, reflecting the amount of hemoglobin that had been released into the supernatant. Percent hemolysis was calculated assuming 100% lysis to be measured by the hemoglobin released by the red blood cells in water; controls of RBCs in buffer with no peptide were also run.

|  | Percent Hemolysis | |
| --- | --- | --- |
| Peptide | pH 5.4 | pH 7.5 |
| Unmodified Peptides | | |
| $KL_3$ | 86, 77, 86 | 54, 77, 54 |
| Melittin | 85 | 92 |
| Dimethylmaleamic Derivatives | | |
| $KL_3$ | 30, 55, 26 | 8, 3, 2 |

-continued

|  | Percent Hemolysis | |
| --- | --- | --- |
| Peptide | pH 5.4 | pH 7.5 |
| Melittin Succinyl Derivatives | 100 | 1 |
| $KL_3$ Melittin | 2, 2, 2 5 | 1, 1, 2 2 |

B) Lysis of Erythrocytes by Poly Propacrylic Acid and subsequent blocking of activity by cationic polymers with reversible blocking of activity with cleavable disulfide cations in the presence of Glutathione. The pH-dependent membrane-disruptive activity of the PPAAc and subsequent blocking of activity by cationic polymers was measured using a red blood cell (RBC) hemolysis assay. RBCs were harvested by centrifuging whole blood for 4 min. They were washed three times with 100 mM dibasic sodium phosphate at the desired pH, and resuspended in the same buffer to yield the initial volume. They were diluted 10 times in the same buffer, and 200 L of this suspension was used for each tube. This yields 10^8 RBCs per tube. Each tube contained 800 L of buffer, 200 L of the RBC suspension, and the polymer. Each sample was done in triplicate, and was then repeated to verify reproducibility. The tubes were incubated for an hour and a half in a 37° C. water bath. They were spun for 5 min at full speed in the microcentifuge. Lysis was determined by measuring the absorbance of the supernatant at 541 nm, reflecting the amount of hemoglobin which had been released into the supernatant. Percent hemolysis was calculated assuming 100% lysis to be measured by the hemoglobin released by the red blood cells in water; controls of RBCs in buffer with no polymer were also run.

| Results at pH 6.0: | |
| --- | --- |
| Mock: | 3% |
| PPAAc: | 98% |
| PPAAc + p-L-Lysine | 3% |
| PPAAc + p-L-Lysine w/1 mM Glutathione | 2% |
| PPAAc + 5,5'-Dithiobis(2-nitrobenzoic acid)-1,4-Bis(3-aminopropyl)piperazine Copolymer | 12% |
| PPAAc + 5,5'-Dithiobis(2-nitrobenzoic acid)-1,4-Bis(3-aminopropyl)piperazine Copolymer w/1 mM Glutathione | 98% |
| PPAAc + L-cystine – 1,4-bis(3-aminopropyl)piperazine copolymer | 2% |
| PPAAc + L-cystine – 1,4-bis(3-aminopropyl)piperazine copolymer w/1 mM Glutathione | 20% |

C) Lysis of Erythrocytes by the peptide Melittin or KL3 and subsequent blocking of activity by anionic polymers or modification with dimethylmaleic anhydride. The membrane-disruptive activity of the peptide melittin and subsequent blocking of activity by anionic polymers was measured using a red blood cell (RBC) hemolysis assay. RBCs were harvested by centrifuging whole blood for 4 min. They were washed three times with 100 mM dibasic sodium phosphate at the desired pH, and resuspended in the same buffer to yield the initial volume. They were diluted 10 times in the same buffer, and 200 uL of this suspension was used for each tube. This yields 10^8 RBCs per tube. Each tube contained 800 uL of buffer, 200 uL of the RBC suspension, and the peptide with or without polymer. Each sample was then repeated to verify reproducibility. The tubes were incubated for 30 minutes in a 37° C. water bath. They were spun for 5 min at full speed in the microcentifuge. Lysis was determined by measuring the absorbance of the supernatant at 541 nm, reflecting the amount of hemoglobin that had been released into the supernatant. Percent hemolysis was calculated assuming 100% lysis to be measured by the hemoglobin released by the red blood cells in water; controls of RBCs in buffer with no peptide were also run.

| Results at pH 7.5: | |
|---|---|
| Mock: | 1% |
| Melittin | 100% |
| Melittin + pAcrylic Acid | 9% |
| DM-Melittin | 1% |
| DM-Melittin post incubation at pH 4 30 seconds | 100% |
| KL3 | 86% |
| DM-KL3 | 4% |
| DM-KL3 post incubation at pH 5.4 30 seconds | 85% |

Example 6

Endosome Lysis

Endosome Disruption Assay: with Dimethylmaleamic-modified melittin. HeLa cells were plated in 6-well tissue culture dishes containing microscope slide coverslips and grown in Delbecco's Modified Eagle's Medium (DMEM)+ 10% fetal calf serum+penn/strep for 24–48 hours until 30–60% confluent. Growth media was aspirated and 1 ml pre-heated (37° C.) serum-free DMEM+2 mg/ml fluorescein isothiocyanate (FITC) labeled dextran(10 kDa)±50 μg DM-melittin or 50 μg melittin was added to the cells and incubated at 37° C. in a humidified $CO_2$ incubator. After 25 min, media containing FITC-dextran±melittin was removed, the cells were washed twice with 1 ml 37° C. DMEM lacking FITC-dextran and melittin, and cells were incubated for an additional 35 min at 37° C. in 1 ml fresh DMEM. In order to assess possible cell lysis caused by melittin, propidium iodide was added for the final 5 min of incubation. Propidium iodide is impermeable to the cell plasma membrane and thus does not stain live cells. However, if the plasma membrane has been damaged, propidium iodide enters the cell where it will brightly stain the nucleus. To process slides for analysis, cells were washed 3 times with cold phosphate buffered saline (PBS), fixed in PBS+4% formaldehyde for 20–30 min at 4° C., and washed again 3 times with cold PBS. Excess liquid was drained from coverslips which were then mounted onto glass slides. Fluorescence was then analyzed on a Zeiss LSM510 confocal microscope. FITC was excited by a 488 nm argon laser and fluorescence emission was detected by a long pass 505 nm filter. FITC-dextran that had been internalized but not released from internal vesicles/endosomes appeared as a punctate cytoplasmic signal. In the presence of DM-melittin, a loss of punctate cytoplasmic signal was observed with a concomitant appearance of a diffuse cytoplasmic signal, indicative of release of dextran from endosomes. For cells incubated with unmodified melittin near 100% cell death was observed as determined by propidium iodide staining of nuclei and loss of cells from the sample.

Example 7

In Vivo Circulation Studies. General procedure for the reaction of poly-L-Lysine compacted DNA particles polyethylene glycol methyl ether 2-propionic-3-methylmaleate (CDM-PEG). Plasmid DNA (200 μg/ml) in 290 mM Glucose/5 mM Hepes pH8 was compacted with poly-L-Lysine (mw: 52,000) (144 μg/ml). This particle is then reacted with 0.5, 1, 2 or 5-fold weight excess of CDM-PEG to amines on the poly-L-lysine.

Effect of CDM-PEG modified poly-L-lysine:DNA particles in vivo. Plasmid DNA labeled with Cy3 Label IT(Mirus Corporation, Madison, Wis.) was compacted into a particle with a 1.2 fold charge excess of poly-L-lysine (mw: 52,000). The particles were then reacted with either a non-reactive Polyethylene Glycol (mw: 5000) or with amine-reactive CDM-PEG at a 0.5 molar equivalent to amines on the poly-L-lysine. 50 μg aliquots of DNA were injected into the tail vein of male ICR mice of approximately 20 grams in weight. Blood was taken at one hour and the smears were inspected for Cy3 fluorescence still in circulation. The animals were then sacrificed and the liver, lung, kidney and spleen were harvested and snap frozen for cryosectioning and the resulting slices were inspected for Cy3 fluorescence.

Results:

The animal injected with the fluorescent particles treated with non-reactive Polyethylene Glycol showed no fluorescence in circulation in the blood at one hour and very little fluorescence in the liver, kidney or spleen, leaving the significant portion of fluorescence in the lung. The animal injected with the fluorescent particles treated with CDM-PEG showed a high level of fluorescence still in circulation in the blood at one hour and also had a high level of fluorescence evenly spread throughout the liver, some spread in the kidney and spleen, with little fluorescence in the lung.

Various Compounds which may be Utilized in the System Provided:

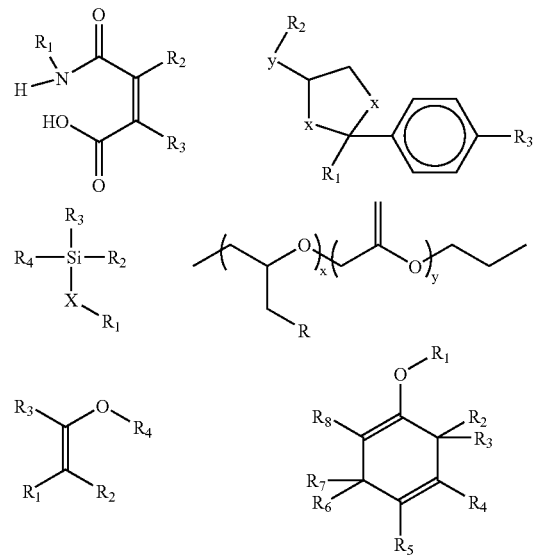

-continued

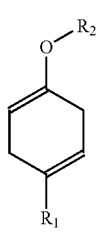 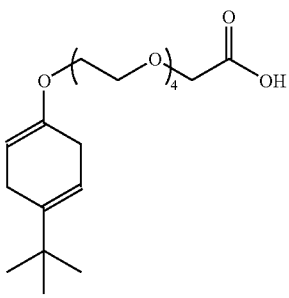

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology, chemistry, molecular biology, biochemistry or related fields are intended to be within the scope of the following claims.

We claim:

1. A process for transfecting a nucleic acid into a cell in vivo, comprising:
   a) attaching a membrane activity inhibitor to a membrane active peptide via a labile linkage, wherein the inhibitor is detached within the cell;
   b) adding the peptide to a solution containing the nucleic acid;
   c) delivering the peptide and nucleic acid to the cell, wherein the peptide and the nucleic acid are endocytosed; and,
   d) transfecting the cell.

2. The process of claim 1 wherein the peptide consists of pardaxin.

3. The process of claim 1 wherein the peptide consists of KL3.

4. The process of claim 1 wherein the peptide consists of magainin.

5. The process of claim 1 wherein the labile linkage is selected from the group consisting of pH-labile, very pH labile, and extremely pH-labile.

6. The process of claim 1 wherein the labile linkage is selected from the group consisting of disulfide, acetal, ketal, enol ether, enol esters amide, imine, imminium, enamine, allyl ether, silazane, and silyl enol ether bonds.

7. The process of claim 1 wherein the labile linkage is selected from the group consisting of dials, diazo, ester, sulfone, and silicon-carbon bonds.

8. A process for transfecting a nucleic acid into a cell in vivo, comprising:
   a) attaching a reversible labile membrane activity inhibitor to a melittin peptide wherein the inhibitor is detached upon association with the cell;
   b) adding the peptide to a solution containing the nucleic acid;
   c) contacting the peptide and nucleic acid with the cell, wherein the peptide and nucleic acid are endocytosed; and,
   d) transfecting to cell.

9. A process for transfecting a nucleic acid into a cell in vivo, comprising:
   a) attaching a membrane activity inhibitor to a membrane active polymer via a labile linkage wherein the inhibitor is detached upon association with the cell;
   b) adding the membrane active polymer to a solution containing the nucleic acid;
   c) contacting the membrane active polymer and nucleic acid with the cell wherein the membrane active polymer and the nucleic acid are endocytosed; and,
   d) transfecting the cell.

10. The process of claim 9 wherein the labile linkage is selected from the group consisting of pH-labile, very pH labile, and extremely pH-labile.

11. The process of claim 9 wherein the labile linkage is selected from the group consisting of disulfide, acetal, ketal, enol ether, enol ester, amide, imine, imminium, enamine, silyl ether, silazane, and silyl enol ether bonds.

12. The process of claim 9 wherein to labile linkage is selected from the group consisting of diols, diazo, ester, sulfone, and silicon-carbon bonds.

* * * * *